US006987214B1

(12) United States Patent
Yanofsky

(10) Patent No.: US 6,987,214 B1
(45) Date of Patent: Jan. 17, 2006

(54) METHODS OF SUPPRESSING FLOWERING IN TRANSGENIC PLANTS

(75) Inventor: Martin F. Yanofsky, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/869,582

(22) PCT Filed: Oct. 15, 1999

(86) PCT No.: PCT/US99/24407

§ 371 (c)(1),
(2), (4) Date: Feb. 28, 2002

(87) PCT Pub. No.: WO00/23578

PCT Pub. Date: Apr. 27, 2000

Related U.S. Application Data

(60) Provisional application No. 60/104,604, filed on Oct. 16, 1998.

(51) Int. Cl.
| | |
|---|---|
| C12N 15/29 | (2006.01) |
| C12N 15/82 | (2006.01) |
| C12N 15/84 | (2006.01) |
| C12N 15/56 | (2006.01) |
| A01H 5/00 | (2006.01) |

(52) U.S. Cl. ........................ 800/287; 800/298; 800/278; 800/290; 800/294; 800/288; 536/24.1; 435/468; 435/199

(58) Field of Classification Search ................ 800/290, 800/298, 278, 287, 294, 288; 536/24.1; 435/468, 435/419, 320.1, 199
See application file for complete search history.

(56) References Cited

U.S. PATENT DOCUMENTS 5,554,798 A    9/1996  Lundquist et al.

FOREIGN PATENT DOCUMENTS

| WO | 97/27287 | 7/1997 |
| WO | 98/13503 | 4/1998 |

OTHER PUBLICATIONS

Izawa et al (1993, J. Mol. Biol. 230 :1131-1144).*
Hao, et al (1998, The J. of Biological Chemistry 273 (41): 26857-26861).*
Busch et al (1999, Science 285:585-587).*
Lohmann et al (2001, Cell 105 :793-803).*
Benfey et al (1990, Science 250:959-966).*
Benfey et al (1989, EMBO J, 8(8):2195-2202).*
Day et al (1995, Development 121:2887-2895).*
Ma, et al., "AGL1-AGL8, an *Arabidopsis* gene family with similarity to floral homeotic and transcription factor genes": *Genes & Development* vol. 5, No. 3, pp. 484-495 (Mar. 1991).
Palmiter, et al. "Cell Lineage Ablation in Transgenic Mice by Cell-specific Expression of a Toxin Gene"; *Cell*, vol. 50 pp 435-443 (Jul. 1987).
Federspiel, et al. "*Arabidopsis thaliana* chromosome I BAC F316 genomic sequence, complete sequence" EMBL Sequence Database, (Aug., 1997) Heidelberg DE.
Mandel, et al. "*Arabidopsis thaliana* MADS-box (AGL9) mRNA, complet cds." EMBL Sequence Database (Aug. 1997) Heidelberg DE.
Rounsley, et al. "T33C10TF TAMU *Arabidopsis thaliana* genomic clone T33C10, genomic survey sequence" EMBL Sequence Database, (Apr. 1998) Heidelberg DE.
Hempel, Frederick D. et al.; "Floral determination and expression of floral regulatory genes in *Arabidopsis*"; 1997, *Development*, vol. 124, pp. 3845-3853.
Nilsson, Ove et al.; "Genetic ablation of flowers in transgenic *Arabidopsis*"; 1998, *The Plant Journal*, vol. 15, No. 6, pp. 799-804.

* cited by examiner

*Primary Examiner*—David T. Fox
*Assistant Examiner*—Stuart F. Baum
(74) *Attorney, Agent, or Firm*—Townsend and Townsend and Crew LLP

(57) ABSTRACT

The present invention provides a transgenic plant characterized by suppressed flowering. The transgenic plant contains a nucleic acid molecule including a floral organ selective regulatory element operatively linked to a nucleotide sequence encoding a cytotoxic gene product, wherein the nucleic acid molecule is heritable by progeny thereof.

20 Claims, 43 Drawing Sheets

Sequence Range: 1 to 4512

```
                                                    50
          AGATCTCTAT GAAAAATGGC AAAATCAACA ATAATCCCTT GGCTATATGG TGGTATTTCT
          TCTAGAGATA CTTTTTACCG TTTTAGTTGT TATTAGGGAA CCGATATACC ACCATAAAGA

100
          GTTAAAAGTG ACTTATGGGT AGATTTTTTA GCTTCATAGA TTCTTTGTCG AAAAAAAATT
          CAATTTTCAC TGAATACCCA TCTAAAAAAT CGAAGTATCT AAGAAACAGC TTTTTTTTAA

150
          ACTTTGTACA TTTTAGTGGA GTTATTTAAA TTTCCCAATT GAACAAAACC ATATATTGAT
          TGAAACATGT AAAATCACCT CAATAAATTT AAAGGGTTAA CTTGTTTTGG TATATAACTA

200
          GAAATTCGCA AATGCAATCC AAAAATAAAT ATGTTCCACT CTTTTGGTTA GCTTTTAACT
          CTTTAAGCGT TTACGTTAGG TTTTTATTTA TACAAGGTGA GAAAACCAAT CGAAAATTGA 250                                        300
          AAACATGCGT TTT------- TTCCAGCTAG TACGAGTCTC TATATATAAA CTTTCTTAAT
          TTTGTACGCA AAA------- AAGGTCGATC ATGCTCAGAG ATATATATTT GAAAGAATTA

350
          ATCGCTAACA ATTTACTTCA AGTTTGTAAT GTGATAAGTG AAAGACCGTA TATACATACA
          TAGCGATTGT TAAATGAAGT TCAAACATTA CACTATTCAC TTTCTGGCAT ATATGTATGT

400
          CATGTTAATC AACTGATAAC CTTTGTGCCT CGTGTGTCTA GTTACTAGTC AACCATCAAA
          GTACAATTAG TTGACTATTG GAAACACGGA GCACACAGAT CAATGATCAG TTGGTAGTTT

450
          CGTGCATGAT GCTGTTTTTC TTAGAGTACT ATTGTTGTGT TATATATAAC TAAACATAAA
          GCACGTACTA CGACAAAAAG AATCTCATGA TAACAACACA ATATATATTG ATTTGTATTT

500
          CAATTTGCTA TTATGATATA AACATAGAAT TTTCAAGCAA TGATATGTTT AGATGTTTTG
          GTTAAACGAT AATACTATAT TTGTATCTTA AAAGTTCGTT ACTATACAAA TCTACAAAAC 550                                        600
          TATAAATATT CCATAAATAG TAGACACCCA TATATACACA AACATGAATT CTACCTGAGG
          ATATTTATAA GGTATTTATC ATCTGTGGGT ATATATGTGT TTGTACTTAA GATGGACTCC

650
          AGAAACACAT AGATGTTCAA ATTAAATAAT AACCCTATAA TGAAAACTCT AAAGTAAGTA
          TCTTTGTGTA TCTACAAGTT TAATTTATTA TTGGGATATT ACTTTTGAGA TTTCATTCAT

700
          ATACGAAATA AAAATTTATC CTTTAAATAA CATATAACAT ATATATCAAC TTTAATTGGT
          TATGCTTTAT TTTTAAATAG GAAATTTATT GTATATTGTA TATATAGTTG AAATTAACCA

750
          AATTGTATCA CAAGAGCCAA TTATTTGGTG ACTGTATCAC ACGTGCTTAA AGAGAGCGTG
          TTAACATAGT GTTCTCGGTT AATAAACCAC TGACATAGTG TGCACGAATT TCTCTCGCAC

800
          GGAATGAAAG TAAAGAAGAA TAAAGAAGCA GAGAGATGGG CTAGAAATGA GAAAACACAC
          CCTTACTTTC ATTCTTCTT ATTTCTTCGT CTCTCTACCC GATCTTTACT CTTTTGTGTG 850                                        900
          CAAACCCTAA CCTCACCCTC ACACATTTCT TATCTTTTGC TCTCAATAGA TTCCATTGAT
          GTTTGGGATT GGAGTGGGAG TGTGTAAAGA ATAGAAAACG AGAGTTATCT AAGGTAACTA
```

Fig. 1a

```
                                                      950
TCAAAACAAA ATTTTCATTA AGATTTCACA ACCTCCACAC ACTTCCAAAC ACAATTAAAG
AGTTTTGTTT TAAAAGTAAT TCTAAAGTGT TGGAGGTGTG TGAAGGTTTG TGTTAATTTC

1000
AGAGGAAAAA GAATCAATAA CCCTATAAAT AAAAAATCAG ACAAACAGAA GTTTCCTCTT
TCTCCTTTTT CTTAGTTATT GGGATATTTA TTTTTAGTC TGTTTGTCTT CAAAGGAGAA

1050
CTTCTTCCTT AAGCTAGTAC CTTTTGTTCT TGAAATTAGG GTTAATTTCT TTTTTCCAAA
GAAGAAGGAA TTCGATCATG GAAAACAAGA ACTTTAATCC CAATTAAAGA AAAAAGGTTT

1100
TACCATCAAT TCTCCAGACC ATAAAAACTC AAAAAGATCA GATCTTTCCT CTGAAAAAGA
ATGGTAGTTA AGAGGTCTGG TATTTTTGAG TTTTTCTAGT CTAGAAAGGA GACTTTTTCT 1150                                        1200
GATACCCAAC TTATGTTTTT GTGTGTCTGT ATATAGATAA ACATTACATA CCCATATTTG
CTATGGGTTG AATACAAAAA CACACAGACA TATATCTATT TGTAATGTAT GGGTATAAAC

1250
TGTATAGACA TAAAAAGTGG AAATTAAGGT AACAAAAGA AATGGGAAGA GGAAGAGTAG
ACATATCTGT ATTTTTCACC TTTAATTCCA TTGTTTTTCT TTACCCTTCT CCTTCTCATC

1300
AGCTGAAGAG GATAGAGAAC AAAATCAACA GACAAGTAAC GTTTGCAAAG CGTAGGAACG
TCGACTTCTC CTATCTCTTG TTTTAGTTGT CTGTTCATTG CAAACGTTTC GCATCCTTGC

1350
GTTTGTTGAA GAAAGCTTAT GAATTGTCTG TTCTCTGTGA TGCTGAAGTT GCTCTCATCA
CAAACAACTT CTTTCGAATA CTTAACAGAC AAGAGACACT ACGACTTCAA CGAGAGTAGT

1400
TCTTCTCCAA CCGTGGAAAG CTCTATGAGT TTTGCAGCTC CTCAAAGTAA ACAACTCTCT
AGAAGAGGTT GGCACCTTTC GAGATACTCA AAACGTCGAG GAGTTTCATT TGTTGAGAGA 1450                                       1500
CACTCTTTAT CAGTTCTTG ATTGAGTTTT TGCTAGATCT GAGCTTAGAT CTTTGTCTCA
GTGAGAAATA GTCAAGAAC TAACTCAAAA ACGATCTAGA CTCGAATCTA GAAACAGAGT

1550
AGGACTTGTT ATATATAGAT CACACGATCT TGATTTCTAC GAAGTTGAGT TAATTAGATT
TCCTGAACAA TATATATCTA GTGTGCTAGA ACTAAAGATG CTTCAACTCA ATTAATCTAA

1600
TCTTGATTTC ATTTTCTAGG GTTTTTTTCC AATTCTTGAA ATTTAAGATC TGGTTTTTTT
AGAACTAAAG TAAAAGATCC CAAAAAAGG TTAAGAACTT TAAATTCTAG ACCAAAAAAA

1650
GTTGTCAATG ATTTAGAACT GTGAATTTTG TAATCGAATA GATTCCAAAT CCTGATATGC
CAACAGTTAC TAAATCTTGA CACTTAAAAC ATTAGCTTAT CTAAGGTTTA GGACTATACG

1700
AATCTGAAAA GTTTTATATA ATTAATATAT GTCTGTGTGA TTGGAAACTT AAAAGTTGGA
TTAGACTTTT CAAAATATAT TAATTATATA CAGACACACT AACCTTTGAA TTTTCAACCT 1750                                            1800
ATCACAGATT TCTATGAAAA TTACAAGTAT CCAACGTAGA ATTGATAATA TATGGTTACA
TAGTGTCTAA AGATACTTTT AATGTTCATA GGTTGCATCT TAACTATTAT ATACCAATGT

1850
TGCATTAACC ATTTGTTAGT TCATCATACT TTATGGTGGT TAAAACTTCA AACGCGTGTA
```

Fig. 1b

```
ACGTAATTGG TAAACAATCA AGTAGTATGA AATACCACCA ATTTTGAAGT TTGCGCACAT
                       1900
TATCTATGAA GGCAAAGATT GTTTGTTTTT TCTTAAAAAC AATGTTTAAT AGATTTTTAA
ATAGATACTT CCGTTTCTAA CAAACAAAAA AGAATTTTTG TTACAAATTA TCTAAAAATT
                       1950
TTATATGTTA AAATAGTTTT GCTTACATGC ATTCAAGAAA ATATAGCGAT TAATTCCTTT
AATATACAAT TTTATCAAAA CGAATGTACG TAAGTTCTTT TATATCGCTA ATTAAGGAAA
            2000
TTTCAAATCA CAATTTGTGA ATCAAACGAA AACGTAAGAT ATTGCTTGCA AATGATAGGA
AAAGTTTAGT GTTAAACACT TAGTTTGCTT TTGCATTCTA TAACGAACGT TTACTATCCT
   2050                                                2100
TTGAACTATT GATATTTGTA AATATAAATA CGAAACTTTA CGTTTGAAAG TTGAAACAAT
AACTTGATAA CTATAAACAT TTATATTTAT GCTTTGAAAT GCAAACTTTC AACTTTGTTA
                                      2150
CAAATCCAAA TCAACTCGTA TATAATCAGA TAAATAATGG AAACAATCTT CAATTTTGAT
GTTTAGGTTT AGTTGAGCAT ATATTAGTCT ATTTATTACC TTTGTTAGAA GTTAAAACTA
                       2200
GGAAGAATAC TTTAAAACTT GAAGAGCTTT TTTTTTTTAT GGTGATTTAT AGGTTTAGAT
CCTTCTTATG AAATTTTGAA CTTCTCGAAA AAAAAAAATA CCACTAAATA TCCAAATCTA
                2250
CTCCAAAGTC AAGTATGATC TTTTTAATAA ACTCTTATTC TCTCTTTTTG AGTTATTTTC
GAGGTTTCAG TTCATACTAG AAAAATTATT TGAGAATAAG AGAGAAAAAC TCAATAAAAG
            2300
AGCATGCTCA AGACACTTGA TCGGTACCAG AAATGCAGCT ATGGATCCAT TGAAGTCAAC
TCGTACGAGT TCTGTGAACT AGCCATGGTC TTTACGTCGA TACCTAGGTA ACTTCAGTTG
   2350                                      2400
AACAAACCTG CCAAAGAACT TGAGGTGTTC TTAATTCAAA TACTATTTTG AGTTCCTATC
TTGTTTGGAC GGTTTCTTGA ACTCCACAAG AATTAAGTTT ATGATAAAAC TCAAGGATAG
                                2450
ATATCATTTC AAGAAAGATC TTTTTTTTTA AAAGTTTGTT TTCGTGAAAT ATTTCAGAAC
TATAGTAAAG TTCTTTCTAG AAAAAAAAAT TTTCAAACAA AAGCACTTTA TAAAGTCTTG
                          2500
AGCTACAGAG AATATCTGAA GCTTAAGGGT AGATATGAGA ACCTTCAACG TCAACAGAGG
TCGATGTCTC TTATAGACTT CGAATTCCCA TCTATACTCT TGGAAGTTGC AGTTGTCTCC
                2550
TACATATCTA TCTATACCTC CATATATTTA CTCAATTCTG TATCCATGTA GATTCATATT
ATGTATAGAT AGATATGGAG GTATATAAAT GAGTTAAGAC ATAGGTACAT CTAAGTATAA
         2600
TGTAGGTGTG TGTGGCTTTT GTTGGTGCAG AAATCTTCTT GGGGAGGATT TAGGACCTTT
ACATCCACAC ACACCGAAAA CAACCACGTC TTTAGAAGAA CCCCTCCTAA ATCCTGGAAA
   2650                                      2700
GAATTCAAAG GAGTTAGAGC AGCTTGAGCG TCAACTGGAC GGCTCTCTCA AGCAAGTTCG
CTTAAGTTTC CTCAATCTCG TCGAACTCGC AGTTGACCTG CCGAGAGAGT TCGTTCAAGC
                                   2750
GTCCATCAAG GTATCTTTAT GCATGGAATC AATGATTCAA ATGAGATTAA TTTGTGTTGT
CAGGTAGTTC CATAGAAATA CGTACCTTAG TTACTAAGTT TACTCTAATT AAACACAACA
```

Fig. 1c

```
                                         2800
TTAATTATAC TACTATGGTG GTATGATGAT TGTTTGCAGA CACAGTACAT GCTTGACCAG
AATTAATATG ATGATACCAC CATACTACTA ACAAACGTCT GTGTCATGTA CGAACTGGTC

2850
CTCTCGGATC TTCAAAATAA AGAGCAAATG TTGCTTGAAA CCAATAGAGC TTTGGCAATG
GAGAGCCTAG AAGTTTTATT TCTCGTTTAC AACGAACTTT GGTTATCTCG AAACCGTTAC

2900
AAGGTATAAT TACAGAATAA ATGCATTTGG TGACTTGCGA TCAATCTCTT TCACAGAGTT
TTCCATATTA ATGTCTTATT TACGTAAACC ACTGAACGCT AGTTAGAGAA AGTGTCTCAA 2950                                                    3000
TAAGTTTCTA AAATATGTTTT GAAACATCTC TAGTTTTCTT GTTTCTGATT ATAGTCTTTT
ATTCAAAGAT TTATACAAAA CTTTGTAGAG ATCAAAAGAA CAAAGACTAA TATCAGAAAA

3050
GGTGAAATGT AAATGTTTAG CTGGATGATA TGATTGGTGT GAGAAGTCAT CATATGGGAG
CCACTTTACA TTTACAAATC GACCTACTAT ACTAACCACA CTCTTCAGTA GTATACCCTC

3100
GATGGGAAGG CGGTGAACAG AATGTTACCT ACGCGCATCA TCAAGCTCAG TCTCAGGGAC
CTACCCTTCC GCCACTTGTC TTACAATGGA TGCGCGTAGT AGTTCGAGTC AGAGTCCCTG

3150
TATACCAGCC TCTTGAATGC AATCCAACTC TGCAAATGGG GTAAATCTGC CTTGAAAAAT
ATATGGTCGG AGAACTTACG TTAGGTTGAG ACGTTTACCC CATTTAGACG GAACTTTTA

3200
CATCTGCAAA TCAGTTTGTG TACTTAACTA CTAAGATTGT CCTTATTTAA GGTTCTTTAG
GTAGACGTTT AGTCAAACAC ATGAATTGAT GATTCTAACA GGAATAAATT CCAAGAAATC 3250                                                    3300
TTGCTTGGTG TAAAGAGGAT CATCAATGTG TGTGAACCTT CTAAGTTGAT GTTTTGGCGA
AACGAACCAC ATTTCTCCTA GTAGTTACAC ACACTTGGAA GATTCAACTA CAAAACCGCT

3350
TGATGATGAT GATGCAGGTA TGATAATCCA GTATGCTCTG AGCAAATCAC TGCGACAACA
ACTACTACTA CTACGTCCAT ACTATTAGGT CATACGAGAC TCGTTTAGTG ACGCTGTTGT

3400
CAAGCTCAGG CGCAGCCGGG AAACGGTTAC ATTCCAGGAT GGATGCTCTG AGAATCATGT
GTTCGAGTCC GCGTCGGCCC TTTGCCAATG TAAGGTCCTA CCTACGAGAC TCTTAGTACA

3450
ACTGTGATGA AGCTCACCCA CAAAAGACCT TATATATATA TAAAGTATAG ATACAAGACT
TGACACTACT TCGAGTGGGT GTTTTCTGGA ATATATATAT ATTTCATATC TATGTTCTGA

3500
TGGATTTGTA GACATAAGTG GCTAATATAA TGGTCCTGAG GATCTTCTAG ACATTTGTAT
ACCTAAACAT CTGTATTCAC CGATTATATT ACCAGGACTC CTAGAAGATC TGTAAACATA 3550                                                   3600
CTTTTGGGAA TCCTTGCTTA TATTAAGAAT TCAAATGTGT GGAACTTGTT TTAACACTGA
GAAAACCCTT AGGAACGAAT ATAATTCTTA AGTTTACACA CCTTGAACAA AATTGTGACT

3650
ACCATGACAC TGGTTTATTA TCATGTAATG AGAGAAACAT TTGGGTTACA ATGTGATCTC
TGGTACTGTG ACCAAATAAT AGTACATTAC TCTCTTTGTA AACCCAATGT TACACTAGAG

3700
TCCTTGACCC AAATACACAA TATAAACCCT ATGCCAAAAT ACAAGCATCA CATATATATA
```

Fig. 1d

```
                                                                 3750
AGGAACTGGG TTTATGTGTT ATATTTGGGA TACGGTTTTA TGTTCGTAGT GTATATATAT
TTCATAAAAG GTTTAAGTAA TCATACAAAT GATGTAAAAA GTTTCATGCC TTGAACAAAA
AAGTATTTTC CAAATTCATT AGTATGTTTA CTACATTTTT CAAAGTACGG AACTTGTTTT
                      3800
CACTGCGCCA AAGGCAAATG GTAAGAAACA TGTCAGATTC CTGTGTGCAT CTGTTTTGCT
GTGACGCGGT TTCCGTTTAC CATTCTTTGT ACAGTCTAAG GACACACGTA GACAAAACGA
           3850                                                  3900
GCTGCTGCTG TTGTTATCTC TCAAGAGGGT TTCCTCAGAA CTCCATAAGC CAAACGTGCA
CGACGACGAC AACAATAGAG AGTTCTCCCA AAGGAGTCTT GAGGTATTCG GTTTGCACGT

3950
GAGAGACGTT TCCTCATTCC CCCATCGTAT ACAATACCAT ATATTGTTAA AAAAAAGATA
CTCTCTGCAA AGGAGTAAGG GGGTAGCATA TGTTATGGTA TATAACAATT TTTTTTCTAT
                                 4000
TCACAGATCA AATCAATTTG CACATCTCTC TGCTGCCTTG TCAATCTCCT CAGGTCCGGT
AGTGTCTAGT TTAGTTAAAC GTGTAGAGAG ACGACGGAAC AGTTAGAGGA GTCCAGGCCA
                       4050
CAAGGCAGAT CAAGACAGGA TCAATGGCAA CAAGTTACGG TGTTTCGTTG AACTCCATCA
GTTCCGTCTA GTTCTGTCCT AGTTACCGTT GTTCAATGCC ACAAAGCAAC TTGAGGTAGT
             4100
CCTGCAAATG AGACGAATTC ACAGCAGAGA AAAAAATATT CTTTAGTCAA CATGAATGAG
GGACGTTTAC TCTGCTTAAG TGTCGTCTCT TTTTTTATAA GAAATCAGTT GTACTTACTC
   4150                                                  4200
AAATAATTCA AATGTTCTGA GTTTCAGGAA GAATGATTAG CCATATTTGT ACTAGACAAG
TTTATTAAGT TTACAAGACT CAAAGTCCTT CTTACTAATC GGTATAAACA TGATCTGTTC
                                  4250
ACAAGTAAAG ATTTTACGCA TGTGCTTCTA GGGTTGTTGT ACATCTTTCA TTCTATTGAT
TGTTCATTTC TAAAATGCGT ACACGAAGAT CCCAACAACA TGTAGAAAGT AAGATAACTA
                                       4300
CTCTGGATCA CTCGTCTATT TATGCGTGAT GGTGTCTGAG TCTGACTCTG AAACACTAGT
GAGACCTAGT GAGCAGATAA ATACGCACTA CCACAGACTC AGACTGAGAC TTTGTGATCA
                  4350
AAATGAGAAG CCGAAAACTG GCTTGGAAGA ACATGAAAAG TGTTTACCTT TCCACAAACA
TTTACTCTTC GGCTTTTGAC CGAACCTTCT TGTACTTTTC ACAAATGGAA AGGTGTTTGT
          4400
GGGCAGTTTT CACTTCTCTC CATCCATTCA TAAATGCAAC TAAGGTGGAA ATGGTGAGAA
CCCGTCAAAA GTGAAGAGAG GTAGGTAAGT ATTTACGTTG ATTCCACCTT TACCACTCTT
     4450                                                4500
CACTTTGTAA CAATCTTCGG GTTCTCTGAT ATGTATTCTA CAAAACACAC GAAATAATCT
GTGAAACATT GTTAGAAGCC CAAGAGACTA TACATAAGAT GTTTTGTGTG CTTTATTAGA

GATACTAAGC TT
CTATGATTCG AA
```

Fig. 1e

```
                                                                -1104
TGATAGCGCT  TCGTTCATCA  TGCAGAAGAA  ACCAATGTTT  CCCCAATCTC
ACTATCGCGA  AGCAAGTAGT  ACGTCTTCTT  TGGTTACAAA  GGGGTTAGAG

-1054
ACGCGCCTCC  TCCTATCTAC  CACCACTTGG  ACAAATCCCC  TTTGCAGTAT
TGCGCGGAGG  AGGATAGATG  GTGGTGAACC  TGTTTAGGGG  AAACGTCATA

-1004
TCGTTTTTTT  TTCCGGACAT  TGTACATTCA  AAAGCATTCC  AAGTGTCTAA
AGCAAAAAAA  AAGGCCTGTA  ACATGTAAGT  TTTCGTAAGG  TTCACAGATT

-954
TAAACATAAC  TAACCACTCC  AAGATGCAAA  ATCTAGCTAC  GACGAACAAA
ATTTGTATTG  ATTGGTGAGG  TTCTACGTTT  TAGATCGATG  CTGCTTGTTT

-904
TTTTAAACTA  TAGAGATGAA  CTTTAAATTC  GGGCATTAAT  TAGTGGAACT
AAAATTTGAT  ATCTCTACTT  GAAATTTAAG  CCCGTAATTA  ATCACCTTGA

-854
TGAGCTATTG  ATGATCGAGT  TTTCTGACTT  TTTGAAGCTT  AAGCTTAATT
ACTCGATAAC  TACTAGCTCA  AAAGACTGAA  AAACTTCGAA  TTCGAATTAA

-804
GAGTTTTATA  TACACTATAT  AGGCTTGTAA  TAATATGGAT  CAAACAAGAA
CTCAAAATAT  ATGTGATATA  TCCGAACATT  ATTATACCTA  GTTTGTTCTT

-754
AAATACAAAC  TACAAATTGG  GAATTGGGTT  TTAAAACGTT  ATCGTTCTAT
TTTATGTTTG  ATGTTTAACC  CTTAACCCAA  AATTTTGCAA  TAGCAAGATA

-704
TTTAATTCAG  GCACGTACCT  TTAGAATATC  AAGATCCATG  TTTCAATATT
AAATTAAGTC  CGTGCATGGA  AATCTTATAG  TTCTAGGTAC  AAAGTTATAA

-654
TCTGTTGACA  AATAAATAAA  GATGTCTCAA  ATATAAGTTG  GGCAACGTAC
AGACAACTGT  TTATTTATTT  CTACAGAGTT  TATATTCAAC  CCGTTGCATG

-604
GTGTAGACCT  AAAAGAGTCG  AAACATTGGT  ATCTAAGTTA  TATATCTACA
CACATCTGGA  TTTTCTCAGC  TTTGTAACCA  TAGATTCAAT  ATATAGATGT

-554
TGGATTATAT  AACAAGACAA  CGTTTGTTTT  AAAAACTTCA  TTGATTTTTC
ACCTAATATA  TTGTTCTGTT  GCAAACAAAA  TTTTTGAAGT  AACTAAAAAG

-504
TTAATTAGTA  GCAACTAGCA  ACTAACTACT  CATGGCAAAT  AATGGCGTCT
AATTAATCAT  CGTTGATCGT  TGATTGATGA  GTACCGTTTA  TTACCGCAGA

-454
GCGTGGCACG  CGACTTGGGA  GAGAAGGTGT  GAGAATGTTT  TTACTTTCTG
CGCACCGTGC  GCTGAACCCT  CTCTTCCACA  CTCTTACAAA  AATGAAAGAC

```
TGTAAAAGAT GGAAGAGAGA GAAAGAGTAA AGAAGTAGAG AGAGAGATAT
ACATTTTCTA CCTTCTCTCT CTTTCTCATT TCTTCATCTC TCTCTCTATA

-354
TGTATCACCA AACCCTAATG ATCTCTCACC CTCACAAATT TTCTTATCTT
ACATAGTGGT TTGGGATTAC TAGAGAGTGG GAGTGTTTAA AAGAATAGAA

-304
TATAGCTTTT ATAGATTCAC AAAAACTTTT CTTCAGATTC ACAATCTCAT
ATATCGAAAA TATCTAAGTG TTTTTGAAAA GAAGTCTAAG TGTTAGAGTA

-254
CACAACCCTT CAAAAAGAGA AAAGATCTAA AGAATAAACA AGAGCCCTAA
GTGTTGGGAA GTTTTTCTCT TTTCTAGATT TCTTATTTGT TCTCGGGATT

-204
TATCAAATCA CAACCAAAAA AACCAAAGAA AGCTAATTAA AGTTTTCTCT
ATAGTTTAGT GTTGGTTTTT TTGGTTTCTT TCGATTAATT TCAAAAGAGA

-154
CTAGCTATTC CTCTTCTTTT CTTGTTCTTG AAAACTAGGG TTTACTTCAC
GATCGATAAG GAGAAGAAAA GAACAAGAAC TTTTGATCCC AAATGAAGTG

-104
CAAAAAGATA AGATCTTTCC CCAGAAAAAG CAATACCCAA GTCATGTTTC
GTTTTTCTAT TCTAGAAAGG GGTCTTTTTC GTTATGGGTT CAGTACAAAG

-54
TGTGTGTCTG TATATAGATA AAACATTACA TACCCTAATA AGGTTACACA
ACACACAGAC ATATATCTAT TTTGTAATGT ATGGGATTAT TCCAATGTGT

-4
AATAGCTATA AAAGAGGGAA AATAAGATAG GGATTTTTTG GGGTGAGGAA
TTATCGATAT TTTCTCCCTT TTATTCTATC CCTAAAAAAC CCCACTCCTT

47
AGATGGGAAG AGGAAGAGTA GAGCTCAAGA GGATAGAGAA CAAAATCAAC
TCTACCCTTC TCCTTCTCAT CTCGAGTTCT CCTATCTCTT GTTTTAGTTG

97
AGACAAGTGA CGTTTGCTAA ACGTAGAAAT GGTTTCGTGA AAAAAGCTTA
TCTGTTCACT GCAAACGATT TGCATCTTTA CCAAAGCACT TTTTTCGAAT

147
TGAGCTTTCT GTTCTCTGCG ATGCTGAAGT CTCTCTCATC GTCTTCTCCA
ACTCGAAAGA CAAGAGACGC TACGACTTCA GAGAGAGTAG CAGAAGAGGT

197
ACCGTGGCAA GCTCTACGAG TTCTGCAGCA CCTCCAAGTA CTTCTCTTTC
TGGCACCGTT CGAGATGCTC AAGACGTCGT GGAGGTTCAT GAAGAGAAAG

247
TTTATACACT TATTAGATCT GTGTGTAGAT CTTTCATTTT TTCTAGTCTT
AAATATGTGA ATAATCTAGA CACACATCTA GAAAGTAAAA AAGATCAGAA

297
GTGATGAGTT TTATCTTTCT TGATTGCTTT TTAACAAAAT ACTTGATATA
```

Fig. 2b

```
CACTACTCAA AATAGAAAGA ACTAACGAAA AATTGTTTTA TGAACTATAT

347
TTTTCAGTTT CTTAATCTGA CTCTAATTAG GTTTTGATTA ATAGGAAGGA
AAAAGTCAAA GAATTAGACT GAGATTAATC CAAAACTAAT TATCCTTCCT

397
AATAAATCCA GGTACCTTTC AAGGTGAATT G------GAG ATCTGATCTT
TTATTTAGGT CCATGGAAAG TTCCACTTAA C------CTC TAGACTAGAA

447
AATTTAATCA TCATGTCAAA TTCTTAGGGA TTTAATTGCA ATCTATTTTT
TTAAATTAGT AGTACAGTTT AAGAATCCCT AAATTAACGT TAGATAAAAA

497
AGATTTATCG GAGCTAGGAA AGTATCATAA TGATATACTA TTATTATCAT
TCTAAATAGC CTCGATCCTT TCATAGTATT ACTATATGAT AATAATAGTA

547
GTAATTTCAT TGTCTCTACA CGGATATATA TGTGATTAGA ACTTGGTAAA
CATTAAAGTA ACAGAGATGT GCCTATATAT ACACTAATCT TGAACCATTT

597
GTAAACTAAA GATTCACAGT CTTCAATGAA ATTGAAAAGA TCCAACGTAG
CATTTGATTT CTAAGTGTCA GAAGTTACTT TAACTTTTCT AGGTTGCATC

647
AATAATTAGT GGTTCCATGC ATTAACCAGT CTAATTAAAG CTCATGCAGA
TTATTAATCA CCAAGGTACG TAATTGGTCA GATTAATTTC GAGTACGTCT

697
CATTTAAGCA CCACATGAAT TTAATATCTT TTTAATTAAG GGATCTTCTT
GTAAATTCGT GGTGTACTTA AATTATAGAA AAATTAATTC CCTAGAAGAA

747
TTTATAAATT TTCTTTTGTT AGCTTTTAAA ATTTTAGTTT GTTCATTAAA
AAATATTTAA AAGAAAACAA TCGAAAATTT TAAAATCAAA CAAGTAATTT

797
ATTTATAGAT CCTCCTCTCC TGATTTGTGT TTTCCGATCC TTTCCAGCAT
TAAATATCTA GGAGGAGAGG ACTAAACACA AAAGGCTAGG AAAGGTCGTA

847
GCTCAAGACA CTGGAAAGGT ATCAGAAGTG TAGCTATGGC TCCATTGAAG
CGAGTTCTGT GACCTTTCCA TAGTCTTCAC ATCGATACCG AGGTAACTTC

897
TCAACAACAA ACCTGCTAAA CAGCTTGAGG TTTAATCTCC AACATCTCTT
AGTTGTTGTT TGGACGATTT GTCGAACTCC AAATTAGAGG TTGTAGAGAA

947
CGATCTTAAT TATTTATCCT TTTTTAATTT TATCTAAAGA AAATGTTTGA
GCTAGAATTA ATAAATAGGA AAAAATTAAA ATAGATTTCT TTTACAAACT

997
TTTTGAGACA AAAGCCCTTC AAAGTTTCTT ACATAGATAT TCAATTGTCT
AAAACTCTGT TTTCGGGAAG TTTCAAAGAA TGTATCTATA AGTTAACAGA
```

Fig. 2c

```
                                                                    1047
ATTATCTTCG CAATTTTCAG AACAGCTACA GAGAGTACTT GAAGCTGAAA
TAATAGAAGC GTTAAAAGTC TTGTCGATGT CTCTCATGAA CTTCGACTTT

1097
GGTAGATATG AAAATCTGCA ACGTCAGCAG AGGTATATAC ATTAATGTGG
CCATCTATAC TTTTAGACGT TGCAGTCGTC TCCATATATG TAATTACACC

1147
ATGATGATCA TTTATAAACA GCATATATAT ATATATATAT ATATATATAT
TACTACTAGT AAATATTTGT CGTATATATA TATATATATA TATATATATA

1197
ATATAGAAAG TATTGATCAT GAAAGTGTGT TGCAGCAGAA ATCTTCTTGG
TATATCTTTC ATAACTAGTA CTTTCACACA ACGTCGTCTT TAGAAGAACC

1247
AGAGGATCTT GGACCTCTGA ATTCAAAGGA GCTAGAGCAG CTTGAGCGTC
TCTCCTAGAA CCTGGAGACT TAAGTTTCCT CGATCTCGTC GAACTCGCAG

1297
AACTAGACGG CTCTCTGAAG CAAGTTCGCT GCATCAAGGT GATTTACTTC
TTGATCTGCC GAGAGACTTC GTTCAAGCGA CGTAGTTCCA CTAAATGAAG

1347
TGTACATACA CTGAAAGATT CACACAAATC TTTCTCTATA TATAGACTGA
ACATGTATGT GACTTTCTAA GTGTGTTTAG AAAGAGATAT ATATCTGACT

1397
GACACATGCA TGAAATGTTT TTGATGCGTG AGGTTATCTG AAAATGCCTC
CTGTGTACGT ACTTTACAAA AACTACGCAC TCCAATAGAC TTTTACGGAG

1447
TTCTTTTTTG CAGACACAGT ATATGCTTGA CCAGCTCTCT GATCTTCAAG
AAGAAAAAAC GTCTGTGTCA TATACGAACT GGTCGAGAGA CTAGAAGTTC

1497
GTAAGGAGCA TATCTTGCTT GATGCCAACA GAGCTTTGTC AATGAAGGTA
CATTCCTCGT ATAGAACGAA CTACGGTTGT CTCGAAACAG TTACTTCCAT

1547
TATGATGATG TTTCTCTCTC TCTCCTCCAG TTTCTATTTA TAGATGGAAA
ATACTACTAC AAAGAGAGAG AGAGGAGGTC AAAGATAAAT ATCTACCTTT

1597
CTTTAAATAG TCCAATTTAT ATATATGAGT CTAAATTTCA CATTCTTCAA
GAAATTTATC AGGTTAAATA TATATACTCA GATTTAAAGT GTAAGAAGTT

1647
CTGCTACATG TTTCTTTTGT ATTATTTCTA TGATATCTTC AGGAAAGTTT
GACGATGTAC AAAGAAAACA TAATAAAGAT ACTATAGAAG TCCTTTCAAA

1697
GAAAAATATT GTGTTTTGTT TAGCTGGAAG ATATGATCGG CGTGAGACAT
CTTTTTATAA CACAAAACAA ATCGACCTTC TATACTAGCC GCACTCTGTA
```

Fig. 2d

```
                                                                1747
CACCATATAG GAGGAGGATG GGAAGGTGGT GATCAACAGA ATATTGCCTA
GTGGTATATC CTCCTCCTAC CCTTCCACCA CTAGTTGTCT TATAACGGAT

1797
TGGACATCCT CAGGCTCATT CTCAGGGACT ATACCAATCT CTTGAATGTG
ACCTGTAGGA GTCCGAGTAA GAGTCCCTGA TATGGTTAGA GAACTTACAC

1847
ATCCCACTTT GCAAATTGGG TAAATCAAAC AACTTTTCTT GCTTTAAGAC
TAGGGTGAAA CGTTTAACCC ATTTAGTTTG TTGAAAAGAA CGAAATTCTG

1897
ATCAACTTAG GTTATAAACA GTTAGCAGTT TGCTTTAAGC CCAACATTGT
TAGTTGAATC CAATATTTGT CAATCGTCAA ACGAAATTCG GGTTGTAACA

1947
CTTTGTTTCA TAGAGGCTTT GGTTAAAACT CGTGTTGTTT AGTCTAAGGA
GAAACAAAGT ATCTCCGAAA CCAATTTTGA GCACAACAAA TCAGATTCCT

1997
TTCAGCACTT TGATGTCTGA AGTATGGAAA ATCAATCTCT CAGACTTGAA
AAGTCGTGAA ACTACAGACT TCATACCTTT TAGTTAGAGA GTCTGAACTT

2047
AATGTGGGTT TCTATTGTTG ACTTCGAAAC TATGTTGTTG TGGTGTTGCA
TTACACCCAA AGATAACAAC TGAAGCTTTG ATACAACAAC ACCACAACGT

2097
AACAGATATA GCCATCCAGT GTGCTCAGAG CAAATGGCTG TGACGGTGCA
TTGTCTATAT CGGTAGGTCA CACGAGTCTC GTTTACCGAC ACTGCCACGT

2147
AGGTCAGTCC CAACAAGGAA ACGGCTACAT CCCTGGCTGG ATGCTGTGAG
TCCAGTCAGG GTTGTTCCTT TGCCGATGTA GGGACCGACC TACGACACTC

2197
CGATACTTCT TCCCCCAATA AAGATCTTAA GCAAGTACTG GTGGGGTCTT
GCTATGAAGA AGGGGGTTAT TTCTAGAATT CGTTCATGAC CACCCCAGAA

2247
CGTGGTGTGA TCTTAGATCT TATGCATATG AATAATAATG TTATTGCACA
GCACCACACT AGAATCTAGA ATACGTATAC TTATTATTAC AATAACGTGT

2297
AGACTTTTGC TTTTGTAGAC ACAAGTGGCT ATAGCTGTAA TAGCCTTCAA
TCTGAAAACG AAAACATCTG TGTTCACCGA TATCGACATT ATCGGAAGTT

2347
CATCTCTCTT CTGTTTCAGG ATTTGTTTGT GCCTATTGTA ATTGCTTATA
GTAGAGAGAA GACAAAGTCC TAAACAAACA CGGATAACAT TAACGAATAT

2397
TATGTATGGT TTGTATAATG TGTGAAATGT TAACATCGAC CATGTCTCAT
ATACATACCA AACATATTAC ACACTTTACA ATTGTAGCTG GTACAGAGTA

CTGGTGAAGA TCTTATCCTG TCTATGCATG ATACCAAAA
```

Fig. 2e

GACCACTTCT AGAATAGGAC AGATACGTAC TATGGTTTT

Fig. 2f

Sequence Range: 1 to 14940

```
                                                   50
TAAAATCTGG AAGTTTCCAG CCCTGATAAT GTTGCAGAAT AAATTAGTGC GCAGTAAGTC
ATTTTAGACC TTCAAAGGTC GGGACTATTA CAACGTCTTA TTTAATCACG CGTCATTCAG

100
TCCAAAAAGA GAGAAACTAC AAATAAATAA ACCAAGTCAA ATTCATTAAC AAGGAGAACA
AGGTTTTTCT CTCTTTGATG TTTATTTATT TGGTTCAGTT TAAGTAATTG TTCCTCTTGT

150
GCATGAAATG TTTCCCAAAC ACACAAAATC TTGACTAGCC AACAGCGCTT CAAATGAGGA
CGTACTTTAC AAAGGGTTTG TGTGTTTTAG AACTGATCGG TTGTCGCGAA GTTTACTCCT

200
AGTAACTAAT TTCAGTAGCT TGGGTATGGT GAAGTATAAT TACCTTCCAC CACACATATC
TCATTGATTA AAGTCATCGA ACCCATACCA CTTCATATTA ATGGAAGGTG GTGTGTATAG 250                                                 300
CGTAGCCTAT CACCCCAACG ATAATGATCA AACCATAGTT TCTACCACCT GTACATTGAA
GCATCGGATA GTGGGGTTGC TATTACTAGT TTGGTATCAA AGATGGTGGA CATGTAACTT

350
GGAAAGTGTT AACTGTTTTC TTCCGAATTT AGATCAACAG TAAACAAAGA ATGGTGTTAC
CCTTTCACAA TTGACAAAAG AAGGCTTAAA TCTAGTTGTC ATTTGTTTCT TACCACAATG

400
TCTAAGTCTC TAATGTAATG CCTTCCTAAA TGCTACAAAG AAAAGCCACT TATCAGAACA
AGATTCAGAG ATTACATTAC GGAAGGATTT ACGATGTTTC TTTTCGGTGA ATAGTCTTGT

450
AAGTATGTCT TGTTTGATGC GAGAAAAGTA GCAAAAGAGA ATAAAACCTG AAATATAATT
TTCATACAGA ACAAACTACG CTCTTTTCAT CGTTTTCTCT TATTTGGAC TTTATATTAA

500
TCAAAATACA ATGTCTAGAA ATCTAAGTGT GCAAATCCTT TATTCAAGTT TCATATCAAA
AGTTTTATGT TACAGATCTT TAGATTCACA CGTTTAGGAA ATAAGTTCAA AGTATAGTTT 550                                                  600
CCAATTTTGA CATTTCTAGT GCAGAACAGA AAACAAAACT TCAATATAAA AAAATATAAA
GGTTAAAACT GTAAAGATCA CGTCTTGTCT TTTGTTTTGA AGTTATATTT TTTTATATTT

650
AACTCCAGAG GACCTGATCC TGAAGGTGAA ACAATGGTGA TAGGTCTGTT TGACCCCAGC
TTGAGGTCTC CTGGACTAGG ACTTCCACTT TGTTACCACT ATCCAGACAA ACTGGGGTCG

700
AACTGTATCT CATGCCTAAG ACTGTTAACC TACAAAAATA AATAGAGCTC AGGCAAGAAA
TTGACATAGA GTACGGATTC TGACAATTGG ATGTTTTTAT TTATCTCGAG TCCGTTCTTT

750
CTATTGATTC ACGATAAATC TATGTCCTCA GCAAGTCTAT ATTATCCAGC TCCATCCGAT
GATAACTAAG TGCTATTTAG ATACAGGAGT CGTTCAGATA TAATAGGTCG AGGTAGGCTA

800
AGCTTATCAT CGCCAATAGA TTAATGTGAA ACTTACCTGG GCCACAAGTA CATCATCGTG
TCGAATAGTA GCGGTTATCT AATTACACTT TGAATGGACC CGGTGTTCAT GTAGTAGCAC 850                                              900
GGGTTTGCTA GCTGATTTGC TAGGTTCGTC TTGTTTCAGT TGCCTGAATA CCATCTGTCC
CCCAAACGAT CGACTAAACG ATCCAAGCAG AACAAAGTCA ACGGACTTAT GGTAGACAGG
```

Fig. 3a

```
                                                   950
ACATAAACAA AACCCATTGC CTCATTTTGC CAAACCGCAT CATACACATG TGAAGTCGCC
TGTATTTGTT TTGGGTAACG GAGTAAAACG GTTTGGCGTA GTATGTGTAC ACTTCAGCGG

1000
AAAGCTTTTG CACAATATAG AAATTAGAAT ACCTTAAAAG CACCAGAAAC CAAATTGGAG
TTTCGAAAAC GTGTTATATC TTTAATCTTA TGGAATTTTC GTGGTCTTTG GTTTAACCTC

1050
ACATCTGGTA AGCCCCCTTC TTTAGAAAAT GCTGATCCAA TAAGACCTTA AAGTAACATT
TGTAGACCAT TCGGGGAAG AAATCTTTTA CGACTAGGTT ATTCTGGAAT TTCATTGTAA

1100
TGCAAAAATC ACAGTATAGT TAGTAATTGC AGTAACTTGG ACGAACATTA AGCATGTACA
ACGTTTTTAG TGTCATATCA ATCATTAACG TCATTGAACC TGCTTGTAAT TCGTACATGT 1150                                                  1200
CGAAATCAAT CGACTCAGCA AGTTCACAAT AATTGTACTA GTAGGTGCAT TCACAGAGAA
GCTTTAGTTA GCTGAGTCGT TCAAGTGTTA TTAACATGAT CATCCACGTA AGTGTCTCTT

1250
ACTAAACATA AACTTCTCCT CAGATGTATT CAGAGAATAG CTATACTCCA ATAAAGTCTT
TGATTTGTAT TTGAAGAGGA GTCTACATAA GTCTCTTATC GATATGAGGT TATTTCAGAA

1300
AAACTTTGAG CCAGTCAAGT ACACTGATCA AAGGGTTTAT GAAAAACACT AACTTCTTAT
TTTGAAACTC GGTCAGTTCA TGTGACTAGT TTCCCAAATA CTTTTGTGA TTGAAGAATA

1350
CCTCTAATTG CGATTACCCA TAGACGAAAC CAATAAAAAA GCAATGGAGA ACTAGAGCAC
GGAGATTAAC GCTAATGGGT ATCTGCTTTG GTTATTTTT CGTTACCTCT TGATCTCGTG

1400
AGTCACTACA AGAAATACCC TATAAAGTA CCGACCTGCA CCGATGAGGA TGGTGAGCTT
TCAGTGATGT TCTTTATGGG ATATTTCAT GGCTGGACGT GGCTACTCCT ACCACTCGAA 1450                                          1500
CCCGAGCGGA AGAGCCATGG CTAGAGACGA GCTTATACGG CGAAGAACTA AGATGGCAAA
GGGCTCGCCT TCTCGGTACC GATCTCTGCT CGAATATGCC GCTTCTTGAT TCTACCGTTT

1550
CGAATCCGCG TGAGAATATC TAAGAGAGTA TTGGTAAGAG AGAGCTGCAG GAACGTACCG
GCTTAGGCGC ACTCTTATAG ATTCTCTCAT AACCATTCTC TCTCGACGTC CTTGCATGGC

1600
GTGAAACAGA GGCGTTTTTT GGGACGATGA AGTGAGGCAG CGAGAGAGAT ACGACGTGCG
CACTTTGTCT CCGCAAAAAA CCCTGCTACT TCACTCCGTC GCTCTCTA TGCTGCACGC

1650
ACTATATTGT TCGCTTGTTG AGGCAACAAA ACAGAGTTGC TTCTAAAACC CGAACCGAAA
TGATATAACA AGCGAACAAC TCCGTTGTTT TGTCTCAACG AAGATTTTGG GCTTGGCTTT

1700
TGTCCGGTCT GATTCGGTCT AAATCACGAT TAGGTTCGTT TTAAAACCTA GGAGGCAATA
ACAGGCCAGA CTAAGCCAGA TTTAGTGCTA ATCCAAGCAA AATTTTGGAT CCTCCGTTAT 1750                                          1800
ACCGGACGGA TCATAAATTC ATAATAGAGA CAGACAAATT GGTCCATTAT TAAAATCACT
TGGCCTGCCT AGTATTTAAG TATTATCTCT GTCTGTTTAA CCAGGTAATA ATTTTAGTGA

1850
TGGGCATTTG GGGATGATTC AAATGCCCAA GTTTTCTCAA ATTTGGACGA TTCATTCACC
```

Fig. 3b

```
ACCCGTAAAC CCCTACTAAG TTTACGGGTT CAAAAGAGTT TAAACCTGCT AAGTAAGTGG
                              1900
TAAGACATAC TTGAGCAACA ACAAAGTGAA GTCCACTGTC ATATCTTATG TCTCAAAAAG
ATTCTGTATG AACTCGTTGT TGTTTCACTT CAGGTGACAG TATAGAATAC AGAGTTTTTC
                              1950
TATTGAAATG TGTCAATTGA TATTGGAGAG GCACACTAGC TAAGGGATTA TTCAATCAAT
ATAACTTTAC ACAGTTAACT ATAACCTCTC CGTGTGATCG ATTCCCTAAT AAGTTAGTTA
                              2000
TTCCAGCAAT TTAATTAAAC TTATTTGTAG TGAAAGTGGG AAGATAAAAG ATCTCACCCT
AAGGTCGTTA AATTAATTTG AATAAACATC ACTTTCACCC TTCTATTTTC TAGAGTGGGA
                  2050                                        2100
CACATGTTCA AAAAAAAAAG TTGAAAATGG AAGTAATTCA ACATGTAGCA TAGAGCCCAA
GTGTACAAGT TTTTTTTTTC AACTTTTACC TTCATTAAGT TGTACATCGT ATCTCGGGTT
                                        2150
ATATGTCTCA TTTTTTTAAT CCATATAATC TCAAATCCTC TTACTTACTT CTAAACATAT
TATACAGAGT AAAAAAATTA GGTATATTAG AGTTTAGGAG AATGAATGAA GATTTGTATA
                              2200
GGTTCCCATA ATCATAACAA TGCTATGTTA ACATGGCCGG TTCTAAAGGA AGCCAAGTGC
CCAAGGGTAT TAGTATTGTT ACGATACAAT TGTACCGGCC AAGATTTCCT TCGGTTCACG
                              2250
AGCAACTGCC TTACGCCTCT ACGTGTTAAA ATGAAAATGA AGACCACTGA CCACTTCTAT
TCGTTGACGG AATGCGGAGA TGCACAATTT TACTTTTACT TCTGGTGACT GGTGAAGATA
                  2300
TAAAGCTTCA TTCACTAGTG TATAATTACA CATTTTTTTA AGGATTTATG AGTAGTGATT
ATTTCGAAGT AAGTGATCAC ATATTAATGT GTAAAAAAAT TCCTAAATAC TCATCACTAA
                        2350                                  2400
GAGGCCCATA TGTTTGTATG TTTGTTTTTC TTACTATATC ATTACTTGAC TATAAGAGTT
CTCCGGGTAT ACAAACATAC AAACAAAAAG AATGATATAG TAATGAACTG ATATTCTCAA
                              2450
GGTTTCCTAT TCCATTCTCT TTTCTAACAG CCTATATATG TAAAAATCTA AGCAAAATTT
CCAAGGATA AGGTAAGAGA AAAGATTGTC GGATATATAC ATTTTTAGAT TCGTTTTAAA
                              2500
CTTGTCAAGA GGATGATTGT ACATTTGTAC TTGGTTATCT CGCCCCGGCC CAAAACATAC
GAACAGTTCT CCTACTAACA TGTAAACATG AACCAATAGA GCGGGGCCGG GTTTTGTATG
                        2550
CTAAGGCCAG GTGCTATATC CTCAACCTGC TTTGGCATTC ATCAATCTAC GAACTTTGGC
GATTCCGGTC CACGATATAG GAGTTGGACG AAACCGTAAG TAGTTAGATG CTTGAAACCG
                  2600
GTGAAACGGT GACAAGATTA ACAAGATTCA CTCTCAACTA CGATGTTCTA CTATCTCAAA
CACTTTGCCA CTGTTCTAAT TGTTCTAAGT GAGAGTTGAT GCTACAAGAT GATAGAGTTT
                        2650                                  2700
TCTTTAAAAA AGTGGATCAA ACTGTCAAAA GTCTAGTTCG ATGGACTAGC TTCAACACTC
AGAAATTTTT TCACCTAGTT TGACAGTTTT CAGATCAAGC TACCTGATCG AAGTTGTGAG
                              2750
CTCCAAATCT AGTTCGATGG ACTATATATT CTCTTCTGAT GCTATCCTTA TCTTGGATTA
GAGGTTTAGA TCAAGCTACC TGATATATAA GAGAAGACTA CGATAGGAAT AGAACCTAAT
```

Fig 3c

```
                                          2800
GGCATCTAAA CTATGGTTTT AATGGTGTCA TGAGGTTTTA CAACTTACAA GGATGAAAGT
CCGTAGATTT GATACCAAAA TTACCACAGT ACTCCAAAAT GTTGAATGTT CCTACTTTCA
                    2850
TATTTACTCC CAGTCACTAT CTTAATCAAA TGACAAAATG TTAACTAGTT TGAGTGCTTA
ATAAATGAGG GTCAGTGATA GAATTAGTTT ACTGTTTTAC AATTGATCAA ACTCACGAAT
                    2900
TATATTAGTT ATGAATCTGA AATTTATTAG TGTGTACATA AGTGATACAA CACTTAAATA
ATATAATCAA TACTTAGACT TTAAATAATC ACACATGTAT TCACTATGTT GTGAATTTAT
          2950                                                   3000
ACATCTACAT GAGTTTTTAA ATAACATAAT AATCCATTAT AGTAGTTTAC GGCATAAGGT
TGTAGATGTA CTCAAAAATT TATTGTATTA TTAGGTAATA TCATCAAATG CCGTATTCCA
                                         3050
ATGAACCAAA TTTTTCATTG CACGCTGAAA AGTGAAAACC TTTAAAATGC ATAATGACTA
TACTTGGTTT AAAAAGTAAC GTGCGACTTT TCACTTTTGG AAATTTTACG TATTACTGAT
                              3100
AGAGTCTATG ACAACAGTAA CTTACTATAT ATTAGAGGAG GGGTGAAAAA AAAAGTAGAG
TCTCAGATAC TGTTGTCATT GAATGATATA TAATCTCCTC CCCACTTTTT TTTTCATCTC
                    3150
AGACTGGTCC AAAAACTTAA CCCCACTCAA TAAACCCAGA CGTGACTTGT TTGACGATAA
TCTGACCAGG TTTTTGAATT GGGGTGAGTT ATTTGGGTCT GCACTGAACA AACTGCTATT
          3200
CTCCATCTTT CTATTTTGGG TAACGAGGTC CCCTTCCCAT TACGTCTTGA CGTGGACCCT
GAGGTAGAAA GATAAAACCC ATTGCTCCAG GGGAAGGGTA ATGCAGAACT GCACCTGGGA
          3250                                         3300
GTCCGTCTAT TTTTAGCAGA TTAATCCAAC GGTTCTTATT CTTTCTTCGA CCCTTCACGA
CAGGCAGATA AAAATCGTCT AATTAGGTTG CCAAGAATAA GAAAGAAGCT GGGAAGTGCT
                              3350
CATTGCCTCA AAGCCGTCCG ATTCTCATCT CACGCCCAAT GGACCACATA TATCACCAGT
GTAACGGAGT TTCGGCAGGC TAAGAGTAGA GTGCGGGTTA CCTGGTGTAT ATAGTGGTCA
                              3400
ACTCCGCAAC TTAGCTGTCG TGTAGGATTT CACGTGGCAT TTATTTGTTC TAGTTTGTAG
TGAGGCGTTG AATCGACAGC ACATCCTAAA GTGCACCGTA AATAAACAAG ATCAAACATC
                    3450
TGCAAACATT GCAAGTTGAT ATGGTCCCCT ATCGATCACC GTCGTCTCTT TAGCTTCACA
ACGTTTGTAA CGTTCAACTA TACCAGGGGA TAGCTAGTGG CAGCAGAGAA ATCGAAGTGT
          3500
TCGAGATTCT TCTTTCTTTC CTACGTGTAA TAGCATTTTT GATTTTGAGA ATTTCTTTAG
AGCTCTAAGA AGAAAGAAAG GATGCACATT ATCGTAAAAA CTAAAACTCT TAAAGAAATC
          3550                                         3600
AACCGTTGGA TCTCTCATCG TTGGTTGATC CATCCATCCA AATGGGACCT GTGTGTGCTC
TTGGCAACCT AGAGAGTAGC AACCAACTAG GTAGGTAGGT TTACCCTGGA CACACACGAG
                              3650
CATCCAGGGC ATATGATCCC AAAGCCAAAA GAGTATTTCC AAGTGCTTTC TTTCTTTCTT
GTAGGTCCCG TATACTAGGG TTTCGGTTTT CTCATAAAGG TTCACGAAAG AAAGAAAGAA
                    3700
TCTTTCTTTC TTACTAACCT TTTTTTTTCT TATGCTTTAG ACTAAGAAAT TTATTCGGCC
```

Fig. 3d

```
                AGAAAGAAAG AATGATTGGA AAAAAAAAGA ATACGAAATC TGATTCTTTA AATAAGCCGG

3750
ATATCCACTT TTACGAATAT ACTTCTTACA AGATCTAGAT TTTTTTGAGT TAATTCGGTG
TATAGGTGAA AATGCTTATA TGAAGAATGT TCTAGATCTA AAAAAACTCA ATTAAGCCAC

3800
TATATAACAT TGGCATGGAC TGCAATTAAG TAATGGTAAT GTGATCATGA TGCGATGTGT
ATATATTGTA ACCGTACCTG ACGTTAATTC ATTACCATTA CACTAGTACT ACGCTACACA 3850                                                 3900
CGTTATCAGT AGTATAATAT TGATGGGCTA CCCTGGAAAA CAAAATTACG TGTTATATGT
GCAATAGTCA TCATATTATA ACTACCCGAT GGGACCTTTT GTTTTAATGC ACAATATACA

3950
ACACAATTTG GTAGAACCGT AGAAATTAAA CTGAATAAAA CCTTCTATAA TGTTCAAAAT
TGTGTTAAAC CATCTTGGCA TCTTTAATTT GACTTATTTT GGAAGATATT ACAAGTTTTA

4000
TATATGGTAC AGATTAATAC GGAAAAACAT TCACGCTTTA CGTAACAATT AAGTGGAAAG
ATATACCATG TCTAATTATG CCTTTTTGTA AGTGCGAAAT GCATTGTTAA TTCACCTTTC

4050
TAAAATTATC CCAAAAATAT TTATATCACA TCATTGTTAT ATTTCTAAGT TTTTTTATAT
ATTTTAATAG GGTTTTTATA AATATAGTGT AGTAACAATA TAAAGATTCA AAAAAATATA

4100
CTCTAATGGT ATATGTTTTA CAGATTGTTT TTTGGGAAAA TTCTTAAAGA GACTTGAAGA
GAGATTACCA TATACAAAAT GTCTAACAAA AAACCCTTTT AAGAATTTCT CTGAACTTCT 4150                                                 4200
ATGTTTTTTT TTTATTTTCT TGAAATGTTT GACACTTGAA ACCGTTTAAA AACTCAAATA
TACAAAAAAA AAATAAAAGA ACTTTACAAA CTGTGAACTT TGGCAAATTT TTGAGTTTAT

4250
TAGTATATAT CATTGTTGGT CTCATACCTT GTAATTCACC ACATATATTA TCAATGGGGA
ATCATATATA GTAACAACCA GAGTATGGAA CATTAAGTGG TGTATATAAT AGTTACCCCT

4300
AGATTTGAAA ATTTTTGGGG GATCACAAAA CGAAGGAAAG AGTACAAAAA GAGAAGGAAA
TCTAAACTTT TAAAAACCCC CTAGTGTTTT GCTTCCTTTC TCATGTTTTT CTCTTCCTTT

4350
AGATAGAAGA TATATGTTTT TAACTTCATT GGTATGACAT CAATAAATAA ATAGTTGAAT
TCTATCTTCT ATATACAAAA ATTGAAGTAA CCATACTGTA GTTATTTATT TATCAACTTA

4400
GTACTTTAGT TTCTCTTTTG GTTTAATGCA CATCATCTCG ATCAATTGTC ATCATCTTAC
CATGAAATCA AAGAGAAAAC CAAATTACGT GTAGTAGAGC TAGTTAACAG TAGTAGAATG 4450                                                 4500
ATTGAATTAT ACGACCAGAT CTGATAACAA GTGAATTCGT ACTTGCCCTT CCCTTTCTTC
TAACTTAATA TGCTGGTCTA GACTATTGTT CACTTAAGCA TGAACGGGAA GGGAAAGAAG

4550
TCATACGTCC TTCTAACTAA TTTTGATTGT AACTTATAAT TATATAACCA TATTTAATTT
AGTATGCAGG AAGATTGATT AAAACTAACA TTGAATATTA ATATATTGGT ATAAATTAAA

4600
TATTTTATCT AAAACCAATT GAAGCAAATT AAAATATCAT AAATCTTGAG TCCCACATGA
ATAAAATAGA TTTTGGTTAA CTTCGTTTAA TTTTATAGTA TTTAGAACTC AGGGTGTACT
```

Fig. 3e

```
                    4650
AGACAATATA TAAAACTCGT GCAAATTTGC TTAAAATGCT TCTATGAGAC CATGACCAAG
TCTGTTATAT ATTTTGAGCA CGTTTAAACG AATTTTACGA AGATACTCTG GTACTGGTTC

4700
TGAGATTAAT AAGCGATTCA ATGTGCAAAT CAAAAGAGAA AAGAAGCTAA TGGGTTTAAA
ACTCTAATTA TTCGCTAAGT TACACGTTTA GTTTTCTCTT TTCTTCGATT ACCCAAATTT 4750                                                 4800
TATAACCAAA CAGAATAATA ATGCTATGTT TAGTTTTTCT AATTGAATCA TACCTTTGTG
ATATTGGTTT GTCTTATTAT TACGATACAA ATCAAAAGA TTAACTTAGT ATGGAAACAC

4850
TCCATCACCT ACTTACCGGT CAGAATAAAG CAATTACGTC TGCAACCAAA AAGCACTAAG
AGGTAGTGGA TGAATGGCCA GTCTTATTTC GTTAATGCAG ACGTTGGTTT TTCGTGATTC

4900
ACTTTCGGTC AGACATGATC TCTAACATCG GACGAACCCT AAGATAACCA AAATAAACTA
TGAAAGCCAG TCTGTACTAG AGATTGTAGC CTGCTTGGGA TTCTATTGGT TTTATTTGAT

4950
TATCTTATAT TCAAATCTCT GTTTATTTTA TCCATTTATG TTTTCTTTCT TTCCCATAAT
ATAGAATATA AGTTTAGAGA CAAATAAAAT AGGTAAATAC AAAAGAAAGA AAGGGTATTA

5000
TTTTTTTGTG TCTCATCAGA CTCTCTTACC AAACTGAATT TATCAACATG GTTTTTTTT
AAAAAAACAC AGAGTAGTCT GAGAGAATGG TTTGACTTAA ATAGTTGTAC CAAAAAAAA 5050                                                5100
TGGCCACATC AAAATGGTGG TTTATAAAGT AGACTAATAC AAAAGACATT TCTGTTAATT
ACCGGTGTAG TTTTACCACC AAATATTTCA TCTGATTATG TTTTCTGTAA AGACAATTAA

5150
TCACTAACAA AAATAATCTT AGCAGTACTA TAGATTGGAA AAGGAAAAGC AAATCTAGCA
AGTGATTGTT TTTATTAGAA TCGTCATGAT ATCTAACCTT TTCCTTTTCG TTTAGATCGT

5200
GTAAGATTTA TCAAAACTAG CAGTAAGAGT TTTAGATATC ATGAAAACAT CACAAACGAG
CATTCTAAAT AGTTTTGATC GTCATTCTCA AAATCTATAG TACTTTTGTA GTGTTTGCTC

5250
TAGTGTTTTA CTTTACATTT TTAACCAATC ACAAGGGTAG TTCCGTAAGT TGGGAAAATC
ATCACAAAAT GAAATGTAAA AATTGGTTAG TGTTCCCATC AAGGCATTCA ACCCTTTTAG

5300
GTACGAGGCT TCACCTAGTT AAGGTTAGGT CACATGATTC CCTGAACTCG ATTTTATAAG
CATGCTCCGA AGTGGATCAA TTCCAATCCA GTGTACTAAG GGACTTGAGC TAAAATATTC 5350                                           5400
TAAAAAAGAA AAATTTATAA AATCAAAATT TTTTATATAA AAAAATCAGG TGGATTTATC
ATTTTTTCTT TTTAAATATT TTAGTTTTAA AAAATATATT TTTTAGTCC ACCTAAATAG

5450
AGACCCTACC ATCGAGATGT CGACACGTGT CCAAACTCAT TCATTGCCCT ACTATTTCT
TCTGGGATGG TAGCTCTACA GCTGTGCACA GGTTTGAGTA AGTAACGGGA TGATAAAAGA

5500
GTTTAGGGTT GCAATCACTC ATCGCACACG CGCCATCTCC ACCTTCCATT ATTAATCTCT
CAAATCCCAA CGTTAGTGAG TAGCGTGTGC GCGGTAGAGG TGGAAGGTAA TAATTAGAGA

5550
CATTTTCAAC ATCACACTCT TACGAATCAT ACGATTTTAA TATCTCTGTC TCTCTCAACG
```

Fig. 3f

```
             GTAAAAGTTG TAGTGTGAGA ATGCTTAGTA TGCTAAAATT ATAGAGACAG AGAGAGTTGC

5600
             TATTAAATAA AAATGGTTTT AAATGTTAGG GTTTTTTGTA GGATTTTCAA TTATTAATCT
             ATAATTTATT TTTACCAAAA TTTACAATCC CAAAAAACAT CCTAAAAGTT AATAATTAGA 5650                                              5700
             CTATAATTCG ATGAACTAAG TAAAAAAGCA TCAAACTTTC TTGGCAGAAT CACATTTTTC
             GATATTAAGC TACTTGATTC ATTTTTTCGT AGTTTGAAAG AACCGTCTTA GTGTAAAAAG

5750
             TCTAAACTAA ATATGGACTG AAATTGAAAA ATTAAACCAC TAGCTAGAAT AAAGTGTTGG
             AGATTTGATT TATACCTGAC TTTAACTTTT TAATTGGTG ATCGATCTTA TTTCACAACC

5800
             TGAGAGTGGA ACTCTAATTT CTCTCCTTTA CTAATTATGT ATAAACACAA AAATGCACCA
             ACTCTCACCT TGAGATTAAA GAGAGGAAAT GATTAATACA TATTTGTGTT TTTACGTGGT

5850
             AATTTTTAGG TTTGAAAATA TCTAAGCATG GATAGGGTAA TTAACATTTT TTCTTTCAAT
             TTAAAAATCC AAACTTTTAT AGATTCGTAC CTATCCCATT AATTGTAAAA AAGAAAGTTA

5900
             TTTGCAATAT TTGAATAAAT CCTATGAGGG TCTTTGGTAC ACAATAATTG GAGGGTATAT
             AAACGTTATA AACTTATTTA GGATACTCCC AGAAACCATG TGTTATTAAC CTCCCATATA 5950                                              6000
             AGTTGAGTCT GAGAGTATAT TAGAAAGAGA ATATTTCAAG TAATGAAGCT GACATGTTTA
             TCAACTCAGA CTCTCATATA ATCTTTCTCT TATAAAGTTC ATTACTTCGA CTGTACAAAT

6050
             TATGTACTTT GAGAGAAGTG TTGTGAGATT TGTACAAATG TATATGTACA CTTTAAAAAG
             ATACATGAAA CTCTCTTCAC AACACTCTAA ACATGTTTAC ATATACATGT GAAATTTTTC

6100
             CAATATAAGA TAGATAAAAA AAATATAAAG AAAAAAAGAA AGAAAGAAAG AAAGAAAGAG
             GTTATATTCT ATCTATTTTT TTTATATTTC TTTTTTTCTT TCTTTCTTTC TTTCTTTCTC

6150
             AGAGGCTCAT ATATATATAG AATTGCTTGC AAGGAAAGAG AGAGAGAGAG ATTGAGATAT
             TCTCCGAGTA TATATATATC TTAACGAACG TTCCTTTCTC TCTCTCTCTC TAACTCTATA

6200
             CTTTTGGGAG AGGAGAAAGA AAAAGAAAAT GGGAAGAGGG AGAGTAGAAT TGAAGAGGAT
             GAAAACCCTC TCCTCTTTCT TTTTCTTTTA CCCTTCTCCC TCTCATCTTA ACTTCTCCTA 6250                                              6300
             AGAGAACAAG ATCAATAGGC AAGTGACGTT TGCAAAGAGA AGGAATGGTC TTTTGAAGAA
             TCTCTTGTTC TAGTTATCCG TTCACTGCAA ACGTTTCTCT TCCTTACCAG AAAACTTCTT

6350
             AGCATACGAG CTTTCAGTTC TATGTGATGC AGAAGTTGCT CTCATCATCT TCTCAAATAG
             TCGTATGCTC GAAAGTCAAG ATACACTACG TCTTCAACGA GAGTAGTAGA AGAGTTTATC

6400
             AGGAAAGCTG TACGAGTTTT GCAGTAGTTC GAGGTATATA TCTACTTTTG TATATATATT
             TCCTTTCGAC ATGCTCAAAA CGTCATCAAG CTCCATATAT AGATGAAAAC ATATATATAA

6450
             ACTTATAACA TAAACATTTT ATATACATAT TAAGTAACAC AAAAATGTCT TGTATGTATG
             TGAATATTGT ATTTGTAAAA TATATGTATA ATTCATTGTG TTTTTACAGA ACATACATAC
```

Fig. 3g

```
                    6500
GGTCTCTCTG TGATGTGTTG TTGTGTCGTA CGTACGTGTT CTATCATATC CTTTTAAAAG
CCAGAGAGAC ACTACACAAC AACACAGCAT GCATGCACAA GATAGTATAG GAAAATTTTC 6550                                                 6600
AAGCAAAGAG GAAAAAAAAT TGGGATACCC CCAAATCTGT ATCATTTTAT AACAAGTTTG
TTCGTTTCTC CTTTTTTTTA AACCCTATGG GGTTTAGACA TAGTAAAATA TTGTTCAAAC

6650
CTTTTTTGAT GTTCTTTTGT GTTTCTCTTT GATTTCCATT TTTGTTTTTG ATTTTTTTTC
GAAAAAACTA CAAGAAAACA CAAAGAGAAA CTAAAGGTAA AAACAAAAAC TAAAAAAAAG

6700
TATTTCTCTT TACATCTATC AAAGTTTTTT TTCTTATATT TTATTGCTTA TTTGTTTGTC
ATAAAGAGAA ATGTAGATAG TTTCAAAAAA AAGAATATAA AATAACGAAT AAACAAACAG

6750
TACTTAATTC ACATTATCTG AGAAGAAC AATCTATCTG ATATGAAATT AGGGTTAATT
ATGAATTAAG TGTAATAGAC TCTCTTCTTG TTAGATAGAC TATACTTTAA TCCCAATTAA

6800
TCTCTTGTGA GTACTCTTTA ATTCACATAA GCTTAAAGTT TCCACCTTTT GATTCTGGGG
AGAGAACACT CATGAGAAAT TAAGTGTATT CGAATTTCAA AGGTGGAAAA CTAAGACCCC 6850                                                 6900
GTCGTCCAAT TCGATCAAAT CACTCAATTT TGTTGTCAGA TTGATATAAG TTCATAGGGG
CAGCAGGTTA AGCTAGTTTA GTGAGTTAAA ACAACAGTCT AACTATATTC AAGTATCCCC

6950
GATATTGTTT CCACGACAAT CCATTTTAGT AACCCTTAGG GGTTTCCAAT TTTGGGTTTT
CTATAACAAA GGTGCTGTTA GGTAAAATCA TTGGGAATCC CCAAAGGTTA AAACCCAAAA

7000
GAATTGACGC TAATGTCAAA TTCATCTAAA GTCCGTTGGA TATGTATACT TGGGGATGGG
CTTAACTGCG ATTACAGTTT AAGTAGATTT CAGGCAACCT ATACATATGA ACCCCTACCC

7050
ATTCATCCTT TTTTCTGGGT TCTTTAGATC TTCTCTTAAA AGACTAACAG ATTTTGTTGT
TAAGTAGGAA AAAAGACCCA AGAAATCTAG AAGAGAATTT TCTGATTGTC TAAAACAACA

7100
AAACCCTAGG AAACAGTTAA AAATCCCATT TTTAAAAACA TGTTTTGAAC TTGATGAGTA
TTTGGGATCC TTTGTCAATT TTTAGGGTAA AAATTTTTGT ACAAAACTTG AACTACTCAT 7150                                                 7200
AGATTAATGG AAGAAATGAT GTTTTTGTGT GGTGTGAAGC ATGCTTCGGA CACTGGAGAG
TCTAATTACC TTCTTTACTA CAAAAACACA CCACACTTCG TACGAAGCCT GTGACCTCTC

7250
GTACCAAAAG TGTAACTATG GAGCACCAGA ACCCAATGTG CCTTCAAGAG AGGCCTTAGC
CATGGTTTTC ACATTGATAC CTCGTGGTCT TGGGTTACAC GGAAGTTCTC TCCGGAATCG

7300
AGTTGTACCC AATTCTCTTC TCTTTCTTCT AATTACCTTA ATTAATTACT CTCAATTTTT
TCAACATGGG TTAAGAGAAG AGAAAGAAGA TTAATGGAAT TAATTAATGA GAGTTAAAAA

7350
ACTTTGATTT TTAGAGTCAA ATGATTAATG TTATAATTTG TCATATACTT CAGGAACTTA
TGAAACTAAA AATCTCAGTT TACTAATTAC AATATTAAAC AGTATATGAA GTCCTTGAAT

7400
GTAGCCAGCA GGAGTATCTC AAGCTTAAGG AGCGTTATGA CGCCTTACAG AGAACCCAAA
```

Fig. 3h

```
CATCGGTCGT CCTCATAGAG TTCGAATTCC TCGCAATACT GCGGAATGTC TCTTGGGTTT 7450                                                    7500
GGTAAACTAA TTAGCTTCTT CAGCTACCTT CAGAGAGTGT TGTTTTTTT AGTAGATTTT
CCATTTGATT AATCGAAGAA GTCGATGGAA GTCTCTCACA AACAAAAAAA TCATCTAAAA

7550
TTTGATGGTT TTGATGTTGA AATAGGAATC TGTTGGGAGA AGATCTTGGA CCTCTAAGTA
AAACTACCAA AACTACAACT TTATCCTTAG ACAACCCTCT TCTAGAACCT GGAGATTCAT

7600
CAAAGGAGCT TGAGTCACTT GAGAGACAGC TTGATTCTTC CTTGAAGCAG ATCAGAGCTC
GTTTCCTCGA ACTCAGTGAA CTCTCTGTCG AACTAAGAAG GAACTTCGTC TAGTCTCGAG

7650
TCAGGGTACT ACTTTGTTCA TCAATATCTT TATACACTGA TCTATTTCCA TAGTAAGATT
AGTCCCATGA TGAAACAAGT AGTTATAGAA ATATGTGACT AGATAAAGGT ATCATTCTAA

7700
AAATTTGGTG TTTAATTCTG CAGACACAGT TTATGCTTGA CCAGCTCAAC GATCTTCAGA
TTTAAACCAC AAATTAAGAC GTCTGTGTCA AATACGAACT GGTCGAGTTG CTAGAAGTCT 7750                                              7800
GTAAGGTAAA TAAAGAAACA CTCATTCTCC TCTCTAAATT CCTCATCTAA AAGTAATGTA
CATTCCATTT ATTTCTTTGT GAGTAAGAGG AGAGATTTAA GGAGTAGATT TTCATTACAT

7850
ACCAAGAAAA CACAAATATT TGGAGCAGGA ACGCATGCTG ACTGAGACAA ATAAAACTCT
TGGTTCTTTT GTGTTTATAA ACCTCGTCCT TGCGTACGAC TGACTCTGTT TATTTTGAGA

7900
AAGACTAAGG GTAATTAATA TACATTCTCA TATCACCAAA TTAATGCATC ACTAAATTTG
TTCTGATTCC CATTAATTAT ATGTAAGAGT ATAGTGGTTT AATTACGTAG TGATTTAAAC

7950
GTTATAATGT GTGTGTGTAT ATACATATGT GACAGTTAGC TGATGGGTAT CAGATGCCAC
CAATATTACA CACACACATA TATGTATACA CTGTCAATCG ACTACCCATA GTCTACGGTG

8000
TCCAGCTGAA CCCTAACCAA GAAGAGGTTG ATCACTACGG TCGTCATCAT CATCAACAAC
AGGTCGACTT GGGATTGGTT CTTCTCCAAC TAGTGATGCC AGCAGTAGTA GTAGTTGTTG 8050                                                    8100
AACAACACTC CCAAGCTTTC TTCCAGCCTT TGGAATGTGA ACCCATTCTT CAGATCGGGT
TTGTTGTGAG GGTTCGAAAG AAGGTCGGAA ACCTTACACT GGGTAAGAA GTCTAGCCCA

8150
AACTTTAGAC TAGTATAACC AATTTGATTT GAGTTCTATT ATAAGCTTTT CTTAAGAAAG
TTGAAATCTG ATCATATTGG TTAAACTAAA CTCAAGATAA TATTCGAAAA GAATTCTTTC

8200
TATCTCAAAC TACTAAATTT TATGGAGCAG GTATCAGGGG CAACAAGATG GAATGGGAGC
ATAGAGTTTG ATGATTTAAA ATACCTCGTC CATAGTCCCC GTTGTTCTAC CTTACCCTCG

8250
AGGACCAAGT GTGAATAATT ACATGTTGGG TTGGTTACCT TATGACACCA ACTCTATTTG
TCCTGGTTCA CACTTATTAA TGTACAACCC AACCAATGGA ATACTGTGGT TGAGATAAAC

8300
AATCTTTCTC ACTTAATCAA TCCCTCTCTT TTTTTTTTGA CATTTTTAAG ATGATGTTTC
TTAGAAAGAG TGAATTAGTT AGGGAGAGAA AAAAAAAACT GTAAAAATTC TACTACAAAG
```

Fig. 3i

```
                8350                                                                    8400
        TATTTTATTA CCTCTCTCAT GTTTTCTGTC TTGTGTGCAT GTGTGTGTGT AATGTTTATG
        ATAAAATAAT GGAGAGAGTA CAAAAGACAG AACACACGTA CACACACACA TTACAAATAC

8450
        CCCTTCTATT ATTCAATAAT TTTTTCGACA ATTTTGCTTC CTATTTTTAC CCATTACTCC
        GGGAAGATAA TAAGTTATTA AAAAGCTGT  TAAAACGAAG GATAAAAATG GGTAATGAGG

8500
        TAAACTTCCT GATCCAGTTT CTTTTAAAAT AACTCCCATT TTATGCATGT TATCTAACCA
        ATTTGAAGGA CTAGGTCAAA GAAAATTTTA TTGAGGGTAA AATACGTACA ATAGATTGGT

8550
        ATTCTCTTAA CTATGATTTA TGGTACGATA TAACTCACAG TCTCACACTA TCTATTTGGT
        TAAGAGAATT GATACTAAAT ACCATGCTAT ATTGAGTGTC AGAGTGTGAT AGATAAACCA

8600
        GTTTTTTTGT TTGAGTCTTG AGAAGGGACC GCTTGTTTAT CTCTCTTGTT AAAGAGCAAC
        CAAAAAAACA AACTCAGAAC TCTTCCCTGG CGAACAAATA GAGAGAACAA TTTCTCGTTG 8650                                                    8700
        TCACTGGCCA CTGCTTATGT ATCTGTAGGC CCCACCTATA TCATTTTGGC TATATCTATA
        AGTGACCGGT GACGAATACA TAGACATCCG GGGTGGATAT AGTAAAACCG ATATAGATAT

8750
        CTTTTGTAGA GGGAGTATTA CTATAGAGAA GAAGATAAAT TTGGTTCTAA TATATCTTGC
        GAAAACATCT CCCTCATAAT GATATCTCTT CTTCTATTTA AACCAAGATT ATATAGAACG

8800
        AGGTAGTTGA TATTCTCAAT TATCATGAAG ATTTGATAGA CAAGTTTATC AGATACCTTA
        TCCATCAACT ATAAGAGTTA ATAGTACTTC TAAACTATCT GTTCAAATAG TCTATGGAAT

8850
        AACATAGGTT TAAGATCTCA ATTGAAATGT GAATTCACCC GACGATTAGA GTTACGATCT
        TTGTATCCAA ATTCTAGAGT TAACTTTACA CTTAAGTGGG CTGCTAATCT CAATGCTAGA

8900
        AAGGAAGCGT TTCTTGAATT TTGAGTTTGT TTGATCAAGA GTAGAATGCT TTTCTATTAC
        TTCCTTCGCA AAGAACTTAA AACTCAAACA AACTAGTTCT CATCTTACGA AAAGATAATG 8950                                                           9000
        TAAGGTTGTT AATGCTTATA TTCCATGACC AAGGCCAAGA GAACAAACAA AAACATGGTG
        ATTCCAACAA TTACGAATAT AAGGTACTGG TTCCGGTTCT CTTGTTTGTT TTTGTACCAC

9050
        CCTCTTGATG TATAGTAATG GCTCTTAATG GTCATATACA GAGAAAAAAA GATTAATGTC
        GGAGAACTAC ATATCATTAC CGAGAATTAC CAGTATATGT CTCTTTTTTT CTAATTACAG

9100
        GTTGCACAAG CTTGAAGTTA CTTACTCCTC GTCTTCCTCA TTAGTGTCTT CGTCTTCCTC
        CAACGTGTTC GAACTTCAAT GAATGAGGAG CAGAAGGAGT AATCACAGAA GCAGAAGGAG

9150
        ATCCTCATCG CTCCCAATAT AGGGCTTCAT CTACTTGAAA ACCAAATGCT CATGCAGTGG
        TAGGAGTAGC GAGGGTTATA TCCCGAAGTA GATGAACTTT TGGTTTACGA GTACGTCACC

9200
        AAAAAGATAA CAGAGGTTCA AATTAAGGCA AACAAAACTA CAAGTGAGAA AGGGAAACTA
        TTTTTCTATT GTCTCCAAGT TTAATTCCGT TTGTTTTGAT GTTCACTCTT TCCCTTTGAT 9250                                                          9300
        CAAGTGGTAA GATGTAATGT TTTGACTCAA AACCAGATCA GACAATGAAA AAAAGTATTG
```

Fig. 3j

```
GTTCACCATT CTACATTACA AAACTGAGTT TTGGTCTAGT CTGTTACTTT TTTTCATAAC

9350
ATACAAAAAG TCCATCCGGA AGCATAATTA CCGCTTGCAG GATGTCATCA GAGATGTCTG
TATGTTTTTC AGGTAGGCCT TCGTATTAAT GGCGAACGTC CTACAGTAGT CTCTACAGAC

9400
TTAGTCGGCC AATGGCATAG ATGGTGAGCG GACCAGAGTA GCGTAAATCC TCTAAATACT
AATCAGCCGG TTACCGTATC TACCACTCGC CTGGTCTCAT CGCATTTAGG AGATTTATGA

9450
GTCTAAAAGC CGGACCGACC CGACAAGGAT CACAGTCAAG GGGAATAGGA CACCTATTGA
CAGATTTTCG GCCTGGCTGG GCTGTTCCTA GTGTCAGTTC CCCTTATCCT GTGGATAACT

9500
TATCCCAAAA GACTGTTGTT ACAGCCACAT CATCCTTGTC CAACTGGGTA GCCCAAAGGG
ATAGGGTTTT CTGACAACAA TGTCGGTGTA GTAGGAACAG GTTGACCCAT CGGGTTTCCC 9550                                              9600
AAACTAGTTG TGGTAAGAGC TTGTTTGACT CAAAAAATGG CTAACTAGGA TGATGCTGAA
TTTGATCAAC ACCATTCTCG AACAAACTGA GTTTTTTACC GATTGATCCT ACTACGACTT

9650
TTACCATCTG TTCATGTTTT TGACTAGAGA GATGGGTAGT GAAATTTTCA AAGCCTTTGC
AATGGTAGAC AAGTACAAAA ACTGATCTCT CTACCCATCA CTTTAAAAGT TTCGGAAACG

9700
AAAACGCCTG TGGGACCTGT TTCAGAAAAA GACTTAAAAG ACTTGAGACT CAAGGAAAAT
TTTTGCGGAC ACCCTGGACA AAGTCTTTTT CTGAATTTTC TGAACTCTGA GTTCCTTTTA

9750
AATATCCATT ATATAAAGAT GACAACAAAT ATTAACGGAA GTAGGAGTGA TTGAGAACGA
TTATAGGTAA TATATTTCTA CTGTTGTTTA TAATTGCCTT CATCCTCACT AACTCTTGCT

9800
TTCTAGTAGA AGAGACGGCT CGCAGGACGT CGTTTATAAT AGGCCAATGG CAGAGATAGT
AAGATCATCT TCTCTGCCGA GCGTCCTGCA GCAAATATTA TCCGGTTACC GTCTCTATCA 9850                                                        9900
GAGAGGACCG GAGTAGCCTA AATTCTTTAA ATGTCGTTTG ATACACGGAC CAACTAGACG
CTCTCCTGGC CTCATCGGAT TTAAGAAATT TACAGCAAAC TATGTGCCTG GTTGATCTGC

9950
AGCATCATAC TCAGAGGGAA CCGGACACGT CTTGATATCC CAGAAGACCG ATGTTACGGC
TCGTAGTATG AGTCTCCCTT GGCCTGTGCA GAACTATAGG GTCTTCTGGC TACAATGCCG

10000
CTTAGCTTGC TGCCGCGTTG CCTTCATCAT CATCTTCTCC TTTTAATCTA TAACGGAAAT
GAATCGAACG ACGGCGCAAC GGAAGTAGTA GTAGAAGAGG AAAATTAGAT ATTGCCTTTA

10050
CAAACATCAG ATAAAGCATT CGAAAAGATA GATTGACACA GGTTAAATCA TCCACTTCAG
GTTTGTAGTC TATTTCGTAA GCTTTTCTAT CTAACTGTGT CCAATTTAGT AGGTGAAGTC

10100
AGAAAAAGAG AGGGACATGG CCGTAAACAA TGAGATAAGG ATCGGCCTAA TGTTTATAAT
TCTTTTTCTC TCCCTGTACC GGCATTTGTT ACTCTATTCC TAGCCGGATT ACAAATATTA 10150                                                       10200
GGGCTTGCGT TTAATGGGCC TACAGTTTCT TGAATCAGCC TTATGCATGA GTCCTAGTAT
CCCGAACGCA AATTACCCGG ATGTCAAAGA ACTTAGTCGG AATACGTACT CAGGATCATA
```

Fig. 3k

```
                                                  10250
TTTATCAACT TTTTTTTTC ATCTTTCTTT AGTTACAATA GATTTAAAGT GTTTTTTGTT
AAATAGTTGA AAAAAAAAG TAGAAAGAAA TCAATGTTAT CTAAATTTCA CAAAAAACAA

10300
AATGCCATTG CAAAATTTGG TAACTGTTTA TAACATTGTT CCTCACTTCA AAATTTAAAG
TTACGGTAAC GTTTTAAACC ATTGACAAAT ATTGTAACAA GGAGTGAAGT TTTAAATTTC

10350
CACCATTAAT AAAAGCTATA CATATAATTA TAACTTGGGT TTTGTGCAAA AAAAACAAAC
GTGGTAATTA TTTTCGATAT GTATATTAAT ATTGAACCCA AAACACGTTT TTTTTGTTTG

10400
AAATTAACCT TTCATTTTAA ATAAATGCAA TTCAATACCG CAATATCAAA AGTAACCCGT
TTTAATTGGA AAGTAAAATT TATTTACGTT AAGTTATGGC GTTATAGTTT TCATTGGGCA 10450                                                   10500
ATAACCTTTA TTCGTGTATA GATTTTAGAA ACAGTATAAG TCAAATTATC AAAACTATGT
TATTGGAAAT AAGCACATAT CTAAAATCTT TGTCATATTC AGTTTAATAG TTTTGATACA

10550
TGTTTTAAGC ATTTTAAAAA TAAGAATAAT AATAATGTTG AAGGGTGGAT TTGAACCCAT
ACAAAATTCG TAAAATTTTT ATTCTTATTA TTATTACAAC TTCCCACCTA AACTTGGGTA

10600
GAACTATAGA ACAAACCAAA GCATGCATAA CCACATGCGC CGAACAAACC AAAAACTCAT
CTTGATATCT TGTTTGGTTT CGTACGTATT GGTGTACGCG GCTTGTTTGG TTTTTGAGTA

10650
GGCTTTGTTA AACATATAAA AATATTCGAA TAAAAAATGT GGGGAACTTG TTACCAGTTT
CCGAAACAAT TTGTATATTT TTATAAGCTT ATTTTTTACA CCCCTTGAAC AATGGTCAAA

10700
TGGTTCTTTT TGGAGCCATT TTTTTCAACA CAGATATTGT TAAGGAGTTT CAGGTAAAAC
ACCAAGAAAA ACCTCGGTAA AAAAAGTTGT GTCTATAACA ATTCCTCAAA GTCCATTTTG 10750                                       10800
TGTATATTAT GCAGGGAACC ACAGTAGGCT ATAATGAAAG TCACACTGTG AAGTTAGCAG
ACATATAATA CGTCCCTTGG TGTCATCCGA TATTACTTTC AGTGTGACAC TTCAATCGTC

10850
ACAAGTTTTT ACTTAAAGAT GTGAGTTGTG ATCTTTTTGA TGTAAGTCTT GATGTATATG
TGTTCAAAAA TGAATTTCTA CACTCAACAC TAGAAAAACT ACATTCAGAA CTACATATAC

10900
TTGACAAATT ATATAAGTTT GTATTGCATA TTCTATGACT TACGAAGTTT CTATGCAAGA
AACTGTTTAA TATATTCAAA CATAACGTAT AAGATACTGA ATGCTTCAAA GATACGTTCT

10950
AAAGCCGGGA GAAAATTTCC GTCAAGTAAC TAAGAGATCG TAATTCTTGT CTGAAGAACA
TTTCGGCCCT CTTTTAAAGG CAGTTCATTG ATTCTCTAGC ATTAAGAACA GACTTCTTGT

11000
ACCCTTTTTT ATTATTTGAG TTTAGGTTGC CAACAGTGAA CAAAGGGACG AGATACCATA
TGGGAAAAAA TAATAAACTC AAATCCAACG GTTGTCACTT GTTTCCCTGC TCTATGGTAT 11050                                          11100
TGACAAATAT CCTCTAACGC CATTTCAACA GTTAATCAAC AGTGTCGGCT ATATGCATGT
ACTGTTTATA GGAGATTGCG GTAAAGTTGT CAATTAGTTG TCACAGCCGA TATACGTACA

11150
GCTAACAATG CACAAGAACA TTGTCACCAT CCCGTGAATA TGAATATTAA TGATTATGAA
```

Fig. 3I

```
CGATTGTTAC GTGTTCTTGT AACAGTGGTA GGGCACTTAT ACTTATAATT ACTAATACTT
                                  11200
CGAGTTTGTA GAGTTCCAAG AGGAAGGTAC TACCTTCTCA TACTCATTGA TCATATATTT
GCTCAAACAT CTCAAGGTTC TCCTTCCATG ATGGAAGAGT ATGAGTAACT AGTATATAAA
                       11250
TGTTTCTTGT TTGTTTTAGT AACTAGGGTT ATTCGGATTG TTTTTCAAAA TAATAGTAAT
ACAAAGAACA AACAAAATCA TTGATCCCAA TAAGCCTAAC AAAAAGTTTT ATTATCATTA
            11300
ATGTCAACTA TATTTATAAA AAAAAAAACT AAATAACTTT TGTACAATTG ATCATTTTTT
TACAGTTGAT ATAAATATTT TTTTTTTGA TTTATTGAAA ACATGTTAAC TAGTAAAAAA
        11350                                              11400
AAATATATCA TAAAGATTCA TCAATATATG AACATATATT TTTAACAATT ACACTAATTG
TTTATATAGT ATTTCTAAGT AGTTATATAC TTGTATATAA AAATTGTTAA TGTGATTAAC
                                             11450
GCTATATAGT GTATAGTTCC TTTTGTGGAG AGGTTTAAGT TCAGTTCAGA GATTATTGTA
CGATATATCA CATATCAAGG AAAACACCTC TCCAAATTCA AGTCAAGTCT CTAATAACAT
                                11500
CTTGGTAAAA TATTTGTCCT TGTTAATTAG TTCATCTTCT AGAATACAGA TTTGGGCCAT
GAACCATTTT ATAAACAGGA ACAATTAATC AAGTAGAAGA TCTTATGTCT AAACCCGGTA
                       11550
GTAGTTTCCC AGAAAACACC GGAAAAAAAA TTCACACTTC ACACCAGAAA CAATAAACGA
CATCAAAGGG TCTTTTGTGG CCTTTTTTTT AAGTGTGAAG TGTGGTCTTT GTTATTTGCT
            11600
GGAACAGAGC CCAAACTCAT CCCTATAATT GGGCCCAAAA AAAGCAGAGC AAACCAAACC
CCTTGTCTCG GGTTTGAGTA GGGATATTAA CCCGGGTTTT TTTCGTCTCG TTTGGTTTGG
       11650                                              11700
AAAATCAAGT AAATCCATTT ACAAATATGC TTTATAATTA TTATTTTTCT CAACCACAAA
TTTTAGTTCA TTTAGGTAAA TGTTTATACG AAATATTAAT AATAAAAGA GTTGGTGTTT
                                             11750
TATGCTTTAT AATTTATGTA AATGTTATAT GAATTATTTA CGATTTATTT TAATTACTTT
ATACGAAATA TTAAATACAT TTACAATATA CTTAATAAAT GCTAAATAAA ATTAATGAAA
                                11800
ATCTTGGAAT TATCTTACGA AGTTAATGAA AATATTTTAA ATATCTAATT TATATATGTC
TAGAACCTTA ATAGAATGCT TCAATTACTT TTATAAAATT TATAGATTAA ATATATACAG
                       11850
TGGACTAAAA TAAATAGAAA TATCTGTATT CCAATCATCA CAAAAAAAAA ATTCTCATCA
ACCTGATTTT ATTTATCTTT ATAGACATAA GGTTAGTAGT GTTTTTTTTT TAAGAGTAGT
            11900
TCTTTGATAT ATAGAAAGTT TTTAAAATTT CAGTTTCACA GATTTTACCA ATTATAGTTT
AGAAACTATA TATCTTTCAA AAATTTTAAA GTCAAAGTGT CTAAAATGGT TAATATCAAA
       11950                                              12000
TATAAGCTTA TGCTAATTAT GTGATCAATG CAAACAAAAG TTGACAATAA TAAAATGAAG
ATATTCGAAT ACGATTAATA CACTAGTTAC GTTTGTTTTC AACTGTTATT ATTTTACTTC
                                             12050
TCAAATATGA TAGATTCCTA CTATAAATAT AGACTCGTGA ATAATACTCG AATCAGTCTC
AGTTTATACT ATCTAAGGAT GATATTTATA TCTGAGCACT TATTATGAGC TTAGTCAGAG
```

Fig. 3m

```
                              12100
TGAGGTTTTG CTGGAAAAGA AAAACCGAAG AGCTCAAAAC AGAGTGCGTT TGTTTCTGGG
ACTCCAAAAC GACCTTTTCT TTTTGGCTTC TCGAGTTTTG TCTCACGCAA ACAAAGACCC

12150
AATCTTCAAG CCTCTCACTT GCGAAGACGA AGCTTACTCG TAAGGTGATT ATCTTCTTCT
TTAGAAGTTC GGAGAGTGAA CGCTTCTGCT TCGAATGAGC ATTCCACTAA TAGAAGAAGA

12200
TCTTCTTCTT TTCAATTCCT TTTTCGTTCA TCTGAAATGT GAAATCATGT GACGTGACGA
AGAAGAAGAA AAGTTAAGGA AAAAGCAAGT AGACTTTACA CTTTAGTACA CTGCACTGCT 12250                                                     12300
TTAGGTTAAC GATCGAATTT CTTAATTTCG TATATGATTA TCTTCTAGTT TCTTGATCAG
AATCCAATTG CTAGCTTAAA GAATTAAAGC ATATACTAAT AGAAGATCAA AGAACTAGTC

12350
CACATCTTGT TGTTTTCTTT CAATCGAGAC TGATTCTAGA TGTTCTTAAG GATCTTGTTC
GTGTAGAACA ACAAAAGAAA GTTAGCTCTG ACTAAGATCT ACAAGAATTC CTAGAACAAG

12400
GATGAACTTT GCATGAATCA TCCATATCGA CGAACTGGTC TGATCTTCTT GTTGTTATGG
CTACTTGAAA CGTACTTAGT AGGTATAGCT GCTTGACCAG ACTAGAAGAA CAACAATACC

12450
ATTAAGTTTC TTGAGATACA AGAAAGGCTT CAATGATCAA TCTGATCTGT TTTGATGAAC
TAATTCAAAG AACTCTATGT TCTTTCCGAA GTTACTAGTT AGACTAGACA AAACTACTTG

12500
ACAAATCTTT ATCTTTGAAC CATGGATAAG GTCAATTTCA CACCATGGCT GGAGGAAGTT
TGTTTAGAAA TAGAAACTTG GTACCTATTC CAGTTAAAGT GTGGTACCGA CCTCCTTCAA 12550                                                     12600
TATCACCGGC GTCATCTTTG GAAGATGTAA AGGCATACGT CAATGCTGTG GAGGTCGCAT
ATAGTGGCCG CAGTAGAAAC CTTCTACATT TCCGTATGCA GTTACGACAC CTCCAGCGTA

12650
TGCAGGAAAT GGAACCTGCA AGATTTGGAA TGTTTGTAAG ACTCTTTCGT GGTTTTACAG
ACGTCCTTTA CCTTGGACGT TCTAAACCTT ACAAACATTC TGAGAAAGCA CCAAAATGTC

12700
CTCCTAGGTG TGTTTGGTTT GCTCTTAAAC AGTCTAAAGA ACAATGACAC ATGTGAGAAT
GAGGATCCAC ACAAACCAAA CGAGAATTTG TCAGATTTCT TGTTACTGTG TACACTCTTA

12750
TGATTCTGAT GTTATTTTTC TCTTTGTAGG ATCGGTATGC CTACTTTCAG TGCACGCATG
ACTAAGACTA CAATAAAAAG AGAAACATCC TAGCCATACG GATGAAAGTC ACGTGCGTAC

12800
CAGGACCTCT TGAAAGATCA CCCGAGTCTG TGTCTTGGTT TAAATGTCTT ACTTCCACCT
GTCCTGGAGA ACTTTCTAGT GGGCTCAGAC ACAGAACCAA ATTTACAGAA TGAAGGTGGA 12850                                           12900
GAGTATCAGT TAACCATACC TCCCGAGGCT AGCGAAGAGT TCATAAGGT GGTTGGAAGA
CTCATAGTCA ATTGGTATGG AGGGCTCCGA TCGCTTCTCA AGTATTCCA CCAACCTTCT

12950
AGCGTACCAG TACCACCAAA GGTGGTTGGA AGAAGTCTAC CACGTCCGGA GCCTACCATA
TCGCATGGTC ATGGTGGTTT CCACCAACCT TCTTCAGATG GTGCAGGCCT CGGATGGTAT

13000
GATGATGCGA CTTCATACCT TATTGCTGTG AAGGAAGCCT TCATGATGA ACCTGCAAAA
```

Fig. 3n

```
CTACTACGCT GAAGTATGGA ATAACGACAC TTCCTTCGGA AAGTACTACT TGGACGTTTT
           13050
TATGGGGAAA TGCTTAAGCT CTTGAAAGAT TTTAAAGCTC GCAGGTATGT ATTAGTTCTT
ATACCCCTTT ACGAATTCGA GAACTTTCTA AAATTTCGAG CGTCCATACA TAATCAAGAA
                 13100
TTCTCCATGT TATGTTTGAT TTTTTCAGTC TACAGAACAA ACACATTATG TGAATTGATT
AAGAGGTACA ATACAAACTA AAAAAGTCAG ATGTCTTGTT TGTGTAATAC ACTTAACTAA
     13150                                                 13200
CTGATGTTAC TAAGTCTCTT TGTAGAGTCG ATGCCGCTTG TGTCATTGCT AGGGTGGAGG
GACTACAATG ATTCAGAGAA ACATCTCAGC TACGGCGAAC ACAGTAACGA TCCCACCTCC
                                                      13250
AACTCATGAA AGATCACTTG AATCTGCTTT TTGGTTTCTG TGTCTTCCTT TCAGCTACAA
TTGAGTACTT TCTAGTGAAC TTAGACGAAA AACCAAAGAC ACAGAAGGAA AGTCGATGTT
                                 13300
CGAGTTTTAC CACGAAGCTT AAGGTATAGA GTGCTTATAG TTACCATTTG ATGTTTCCTA
GCTCAAAATG GTGCTTCGAA TTCCATATCT CACGAATATC AATGGTAAAC TACAAAGGAT
                      13350
TATGTTAACT TGTGGTTTAA GTAACAAAAT TGTCCATGTG CAGGCAAGGT TTCAGGGCGA
ATACAATTGA ACACCAAATT CATTGTTTTA ACAGGTACAC GTCCGTTCCA AAGTCCCGCT
           13400
TGGTAGTCAA GTAGTTGACT CAGTTCTTCA GATAATGAGA ATGTACGGTG AGGGAAACAA
ACCATCAGTT CATCAACTGA GTCAAGAAGT CTATTACTCT TACATGCCAC TCCCTTTGTT
     13450                                                 13500
GTCCAAACAT GATGCGTATC AGGAGGTAGG CTTCTTGGTA GGATACTTTG TGTTGTGTGT
CAGGTTTGTA CTACGCATAG TCCTCCATCC GAAGAACCAT CCTATGAAAC ACAACACACA
                                            13550
TGCACTTTCT TAGTTCTTTG GTTTGATTTG CTTTGTTATC TTTTGCAGGT CGTTGCACTT
ACGTGAAAGA ATCAAGAAAC CAAACTAAAC GAAACAATAG AAAACGTCCA GCAACGTGAA
                                 13600
GTTCAGGGTC ATGACGATTT AGTCATGGAG CTTTCACAAA TTTTGACTGA TCCACCTACT
CAAGTCCCAG TACTGCTAAA TCAGTACCTC GAAAGTGTTT AAAACTGACT AGGTGGATGA
                      13650
GGAGTCTAGA GATAGCCAGA TAGCTAAGGA GAGTACTGGA AGACTGTAAT ATACCATAAG
CCTCAGATCT CTATCGGTCT ATCGATTCCT CTCATGACCT TCTGACATTA TATGGTATTC
           13700
AGACGAAAAA GAAAGTAGAG CTTCTCACGA AAAGAGAGTG TTTTTAGTTT TCTTTTGCAA
TCTGCTTTTT CTTTCATCTC GAAGAGTGCT TTTCTCTCAC AAAAATCAAA AGAAAACGTT
     13750                                                 13800
ACATTAGAGT TTTGTTTGAT TAACATGACA TTCAAAAATA TGCTATGCTT CTATGTTGAG
TGTAATCTCA AAACAAACTA ATTGTACTGT AAGTTTTTAT ACGATACGAA GATACAACTC
                                            13850
GTGTACAATG AATTGGTGTA TAAGAGACTA AAAGAGAGTG TATAGTTTCT TTGTTGAGGT
CACATGTTAC TTAACCACAT ATTCTCTGAT TTTCTCTCAC ATATCAAAGA AACAACTCCA
                                 13900
TTCTTTTATG TTGAGGTGTT CAATATGCTA TTTTCAGGGT AATCTTTTTA TAAGAAACTG
AAGAAAATAC AACTCCACAA GTTATACGAT AAAAGTCCCA TTAGAAAAAT ATTCTTTGAC
```

Fig. 3o

```
                      13950
AGAAGGGAAA CACTCAAAAA ACAGAGTTCA ACGTAGAAAC AAAAACAGAG AGGTGAACTC
TCTTCCCTTT GTGAGTTTTT TGTCTCAAGT TGCATCTTTG TTTTTGTCTC TCCACTTGAG

14000
ATGAAAGATC AATTTAACCT GCTTGTGATG ATTGGCTTAT CAAGAGAATT GAAGAGATTC
TACTTTCTAG TTAAATTGGA CGAACACTAC TAACCGAATA GTTCTCTTAA CTTCTCTAAG 14050                                              14100
ACGATTACAC AAAATTCAATT CTTAAAGACA AGAGTAGACT GCTAATTCTT ATTAAGGCTG
TGCTAATGTG TTTAAGTTAA GAATTTCTGT TCTCATCTGA CGATTAAGAA TAATTCCGAC

14150
TTAATGCTTC TTGAGAGCAT TGACCTTTTC CCTGAGGTAA TAAAGCTTGG CTCTTCTTAC
AATTACGAAG AACTCTCGTA ACTGGAAAAG GGACTCCATT ATTTCGAACC GAGAAGAATG

14200
TTTCTTCTTG TCCACCACCT TAATCACCCT CAGGTTGGG GAATACCTGT CACCAAAACA
AAAGAAGAAC AGGTGGTGGA ATTAGTGGGA GTCCAAACCC CTTATGGACA GTGGTTTTGT

14250
CCTCCACTTA CATCAGTATT TTCCATGACC AAGGCAAACA AAGAGAACAT ACAAAACATG
GGAGGTGAAT GTAGTCATAA AAGGTACTGG TTCCGTTTGT TTCTCTTGTA TGTTTGTAC

14300
GTGGCTCTTG ATTATAATAA TGGCTCTTAA TGGTCATATA CAAAAGTCTG AGAGAAAAG
CACCGAGAAC TAATATTATT ACCGAGAATT ACCAGTATAT GTTTTCAGAC TCTCTTTTTC 14350                                            14400
ATTAAAGTGG CTGCACAAGC TTGAAGCTTG AAGTTACTTA CAAGGGGAAC ATGGATTCGA
TAATTTCACC GACGTGTTCG AACTTCGAAC TTCAATGAAT GTTCCCCTTG TACCTAAGCT

14450
CGCCCACTCC AGCAACAAGC CTTCTAATTC TAAATGTTGA GTTGAGACCA GCATTACGCC
GCGGGTGAGG TCGTTGTTCG GAAGATTAAG ATTTACAACT CAACTCTGGT CGTAATGCGG

14500
TTGCTATGAC GACGCCTTTT ACGATTGATA CACGCCTCTT GTTCTCAGGC ACTTCCTGTT
AACGATACTG CTGCGGAAAA TGCTAACTAT GTGCGGAGAA CAAGAGTCCG TGAAGGACAA

14550
CAAACAAAGT AAATGAAAGG TTTCACTTAG AAGATGAAAG ATAGTTTGAT CTTACTCACC
GTTTGTTTCA TTTACTTTCC AAAGTGAATC TTCTACTTTC TATCAAACTA GAATGAGTGG

14600
CAAGAAAAAG AAATTACAAC CTAGGCCAAC AGTAGTTACC ACTTTTAGCT GCACAATGTA
GTTCTTTTTC TTTAATGTTG GATCCGGTTG TCATCAATGG TGAAAATCGA CGTGTTACAT 14650                                              14700
ACCAGGCTTT ATCTCTGGAA TCTCTCTAAG AGTTCTCACT TCCTCAACTG CTTCCTTGTC
TGGTCCGAAA TAGAGACCTT AGAGAGATTC TCAAGAGTGA AGGAGTTGAC GAAGGAACAG

14750
TACAATCTGC AGAGGATTGT GACATCGGTG CTTCCTTGTC TACATGATAT ATCTAAATAC
ATGTTAGACG TCTCCTAACA CTGTAGCCAC GAAGGAACAG ATGTACTATA TAGATTTATG

14800
AAGTGTCAAG TTCGAGTTGT AGTACCTGCA TAATATGCTT AGCGGTTTTA TCAAGCCGCT
TTCACAGTTC AAGCTCAACA TCATGGACGT ATTATACGAA TCGCCAAAAT AGTTCGGCGA

14850
TAAACTTGAT TCTCTGAGGC ACAACACAAT CTGACTCAGG GGATCCTTGA ACAGAATCTC
```

Fig. 3p

```
ATTTGAACTA AGAGACTCCG TGTTGTGTTA GACTGAGTCC CCTAGGAACT TGTCTTAGAG
               14900
CAGTGGTGGA AAAACACCTC GACGAAAAGT TTTGTTTCTG CCAAAAAAAT ATTCCCAAGA
GTCACCACCT TTTTGTGGAG CTGCTTTTCA AAACAAAGAC GGTTTTTTTA TAAGGGTTCT
```

Fig. 3q

```
(2) CCCTCACACATTTCTTATCTTTTGCTCTCAATAGATTCCATTGATTCAAAACAAAATTTTCATTAAGATTTCACAACCTCCACACA    86
(4) ------------------------------------GATTCA-CAAAAACTTTTC-TTCAGATT-CACAATCTCATCACAA    42
(2) --CTTCC---------------AAACACAATTAAAGAGAGGAAAAAGAATCAATAACCCTATAAATAAAAAATCAGACAAACAGA   154
(4) CCCTTCAAAAAGAGAAAAGATCTAAAGAATAAACAAGAGCCCTAATATCAAATCACAACCAAAAAAACCAAAGAAAG-CTAATTAA   127
(2) AGTTTCCTCTTCTTCTTCCTTAAGCTAGTACCTTTTGTTCTTGAAA-TTAGGGTTAATTTCTTTTTTTCCAAATACCATCAATTCT   238
(4) AGTTTTCTCTCTAGCTATTCCTCTT---CTTTTCTTGTTCTTGAAAACTAGGGTTTACTT---------------------    184
(2) CCAGACCATAAAAACTCAAAAAGATCAGATCTTTCCTCTGAAAAAGAGATACCCAACTTATGTTTTTGTGTGTCTGTATATAG    321
(4) --------------CACCAAAAGATAAGATCTTTCCCCAGAAAAAGCAATACCCAAGTCATGTTTCTGTGTGTCTGTATATAG    253
(2) ATAAA-CATTACATACCCATATTTGTGTATAGACATAAAAAGTGGAAATTAAGGTAACAAAAAGAA-------------------  386
(4) ATAAAACATTACATACCCTAATAAGGTTACACAAATAGCTATAAAAGAGGGAAAATAAGATAGGGATTTTTTGGGGTGAGGAAAG    338
ATGGGAAGAGGAAGAGTAGAGCTGAAGAGGATAGAGAACAAAATCAACAGACAAGTAACGTTTGCAAAGCGTAGGAACGGTTTGTTGAAG   476
                 C                                 G       T A     T       C  A   428
M  G  R  G  V  E  L  K  R  I  E  N  K  I  N  R  Q  Y  T  F  A  K  R  R  H  G  L  L  K    30
AAAGCTTATGAATTGTCTGTTCTCTGTGATGCTGAAGTTGCTCTCATCATCTTCTCCAACCGTGGAAAGCTCTATGAGTTTTGCAGCTCC   566
           GC T        C         CT     G                C         C       C     A   518
K  A  Y  E  L  S  V  L  C  D  A  E  V  A  L  I  I  F  S  N  R  G  K  L  Y  E  F  C  S     60
                                    S     V                                      T
TCAAACATGCTCAAGACACTTGATCGGTACCAGAAATGCAGCTATGGATCCATTGAAGTCAACAACAAACCTGCCAAAGAACTTGAGAAC   656
 C                G  AA     T    G T         C                                T     G   608
S  N  M  L  K  T  L  D  R  Y  Q  K  C  S  Y  G  S  I  E  V  N  N  K  P  A  K  E  L  E  N   90
                      E
AGCTACAGAGAATATCTGAAGCTTAAGGGTAGATATGAGAACCTTCAACGTCAACAGAGAAATCTTCTTGGGGAGGATTTAGGACCTTTG   746
            G  CT    G  A         ATG       G                        A       CT      C   698
S  Y  R  E  Y  L  K  L  K  G  R  Y  E  N  L  Q  R  Q  Q  R  N  L  L  G  E  D  L  G  P  L  120
AATTCAAAGGAGTTAGAGCAGCTTGAGCCGTCAACTGGACGGCTCTCTCAAGCAAGTTCCGTCCATCAAGACACAGTACATGCTTGACCAG   836
      C                     A             G          C G             T                   788
N  S  K  E  L  E  Q  L  E  R  Q  L  D  G  S  L  K  Q  V  R  S  I  K  T  Q  Y  M  L  D  Q  150
                                                       C
CTCTCGGATCTTCAAAATAAAGAGCAAATGTTGCTTGAAACCAATAGAGCTTTGGCAATGAAGCTGGATATATGATTGGTGTGAGAAGT    926
   T            GG   C      T  C          TG   C          T             A         C  C   CA   878
L  S  D  L  Q  N  K  E  Q  M  L  L  E  T  N  R  A  L  A  M  K  L  D  D  M  I  G  V  R  S   180
               G              I       D  A          R           E                      H
CATCATATG---GGAGGATGGAAGGCGGTGAA---CAGAATGTTACCTACGCGCATCATCAAGCTCAGTCTCAGGGACTATACCAGCCT   1010
        C       AGGA     T         TCAA      A  G     T GA    C  G       T              AT    968
M  H  M  -  G  G  W  E  G  E  -  Q  N  V  T  Y  A  H  H  Q  A  Q  S  Q  G  L  Y  Q  P    208
         I  Q              D  Q        I  A  G  P     E                             S    210
CTTGAATGCAATCCAACTCTGCAAATGGGGTATGATAATCCAGTATGCTCTGAGCAAATCACTGCGACAACACAAGCTCAGGCGCAGCCG   1100
         TG   C  T         T A   AGCC        G     A         GG  T GGTG    G    TC A AA   1058
L  E  C  N  P  T  L  Q  M  G  Y  D  N  P  V  C  S  R  Q  I  T  A  T  T  Q  A  A  P        238
         D                 I     S  K              M  A  V  V  G  S         Q            240
GGAAACGGTTACATTCCAGGATGGATGCTCTGAGAATCATGTACTGTCATGAAGCTCACCCACAAAAGACCTTATATATATATAAAGTAT   1190
     C      C TC            G      GCCGATACTTCTTCCCCCAATAAAGATCTTAAGCAAGTACTGGTGGGGTCTTCGTGGT   1148
G  N  G  Y  I  P  G  M  K  L  End    248
                                      250
(2) AGATACAAGACTTGGATTTGTAGACATAAGTGGCTAATATAATGGTCCTGAGGATCTTCTAGACATTTGTATCTTTTGGGAATCCTT   1277
    GCTTATATTAAGAATTC    1294
(4) GTGATCTTAGATCTTATGCATATGAATAATAATGTTATTGCACAAGACTTTTGCTTTTGTAGACACAAGTGGCTATAGCTGTAATAG    1235
    CCTTCAACATCTCTCTTCTGTTTCAGGATTTGTTTGTGCCTATTGTAATTGCTTATATATGTATGGTTTGTATAATGTGTGAAATGT   1322
                             S                                       S
    TAACATCGACCATGTCTCATCTGGTGA$_n$
           S    S
```

Figure 4

Sequence Range: -12 to 815

```
                                                        38
CCCGGATCCA AAATGGGAAG AGGGAGAGTA GAATTGAAGA GGATAGAGAA CAAGATCAAT
           K M G R    G R V      E L K      R I E N    K I N>

88
AGGCAAGTGA CGTTTGCAAA GAGAAGGAAT GGTCTTTTGA AGAAAGCATA CGAGCTTTCA
R Q V      T F A K    R R N      G L L     K K A Y    E L S>

138
GTTCTATGTG ATGCGGAAGT TGCTCTCATC ATCTTCTCAA ATAGAGGAAA GCTGTACGAG
V L C      D A E V    A L I      I F S     N R G K    L Y E>

188
TTTTGCAGTA GTTCGAGCAT GCTTCGGACA CTGGAGAGGT ACCAAAAGTG TAACTATGGA
F C S      S S S M    L R T      L E R      Y Q K C    N Y G>

238                                                 288
GCACCAGAAC CCAATGTGCC TTCAAGAGAG GCCTTAGCAG AACTTAGTAG CCAGCAGGAG
A P E      P N V P    S R E      A L A      E L S S    Q Q E>

338
TATCTCAAGC TTAAGGAGCG TTATGACGCC TTACAGAGAA CCCAAAGGAA TCTGTTGGGA
Y L K      L K E R    Y D A      L Q R      T Q R N    L L G>

388
GAAGATCTTG GACCTCTAAG TACAAAGGAG CTTGAGTCAC TTGAGAGACA GCTTGATTCT
E D L      G P L S    T K E      L E S      L E R Q    L D S>

438
TCCTTGAAGC AGATCAGAGC TCTCAGGACA CAGTTTATGC TTGACCAGCT CAACGATCTT
S L K      Q I R A    L R T      Q F M      L D Q L    N D L>

488
CAGAGTAAGG AACGCATGCT GACTGAGACA AATAAAACTC TAAGACTAAG GTTAGCTGAT
Q S K      E R M L    T E T      N K T      L R L R    L A D>

538                                                 588
GGGTATCAGA TGCCACTCCA GCTGAACCCT AACCAAGAAG AGGTTGATCA CTACGGTCGT
G Y Q      M P L Q    L N P      N Q E      E V D H    Y G R>

638
CATCATCATC AACAACAACA ACACTCCCAA GCTTTCTTCC AGCCTTTGGA ATGTGAACCC
H H H      Q Q Q Q    H S Q      A F F      Q P L E    C E P>

688
ATTCTTCAGA TCGGGTATCA GGGGCAACAA GATGGAATGG GAGCAGGACC AAGTGTGAAT
I L Q      I G Y Q    G Q Q      D G M      G A G P    S V N>

738
AATTACATGT TGGGTTGGTT ACCTTATGAC ACCAACTCTA TTTGAATCTT TCTCACTTAA
N Y M      L G W L    P Y D      T N S      I * I F    L T *>

788
TCAATCCCTC TCTTTTTTTT TTTGACATTT TTAAGATGAT GTTTCTA
S I P      L F F F    L T F      L R *      C F X>
```

Fig. 5

Sequence Range: -1699 to 3669

```
                                                                -1650
          GAATTCCCCG GATCTCCATA TACATATCAT ACATATATAT AGTATACTAT CTTTAGACTG
          CTTAAGGGGC CTAGAGGTAT ATGTATAGTA TGTATATATA TCATATGATA GAAATCTGAC

-1600
ATTTCTCTAT ACACTATCTT TTAACTTATG TATCGTTTCA AAACTCAGGA CGTACATGTT
TAAAGAGATA TGTGATAGAA AATTGAATAC ATAGCAAAGT TTTGAGTCCT GCATGTACAA

-1550
TTAAATTTGG TTATATAACC ACGACCATTT CAAGTATATA TGTCATACCA TACCAGATTT
AATTTAAACC AATATATTGG TGCTGGTAAA GTTCATATAT ACAGTATGGT ATGGTCTAAA

-1500
AATATAACTT CTATGAAGAA AATACATAAA GTTGGATTAA AATGCAAGTG ACATCTTTTT
TTATATTGAA GATACTTCTT TTATGTATTT CAACCTAATT TTACGTTCAC TGTAGAAAAA

-1450                                                    -1400
AGCATAGGTT CATTTGGCAT AGAAGAAATA TATAACTAAA AATGAACTTT AACTTAAATA
TCGTATCCAA GTAAACCGTA TCTTCTTTAT ATATTGATTT TTACTTGAAA TTGAATTTAT

-1350
GATTTACTA TATTACAATT TTTTCTTTTT ACATGGTCTA ATTTATTTTT CTAAAATTAG
CTAAAATGAT ATAATGTTAA AAAAGAAAAA TGTACCAGAT TAAATAAAAA GATTTAATC

-1300
TATGATTGTT GTTTTGATGA AACAATAATA CCGTAAGCAA TAGTTGCTAA AAGATGTCCA
ATACTAACAA CAAAACTACT TTGTTATTAT GGCATTCGTT ATCAACGATT TTCTACAGGT

-1250
AATATTTATA AATTACAAAG TAAATCAAAT AAGGAAGAAG ACACGTGGAA AACACCAAAT
TTATAAATAT TTAATGTTTC ATTTAGTTTA TTCCTTCTTC TGTGCACCTT TTGTGGTTTA

-1200
AAGAGAAGAA ATGGAAAAAA CAGAAAGAAA TTTTTTAACA AGAAAAATCA ATTAGTCCTC
TTCTCTTCTT TACCTTTTTT GTCTTTCTTT AAAAAATTGT TCTTTTTAGT TAATCAGGAG

-1150                                                    -1100
AAACCTGAGA TATTTAAAGT AATCAACTAA AACAGGAACA CTTGACTAAC AAAGAAATTT
TTTGGACTCT ATAAATTTCA TTAGTTGATT TTGTCCTTGT GAACTGATTG TTTCTTTAAA

-1050
GAAATGTGGT CCAACTTTCA CTTAATTATA TTGTTTTCTC TAAGGCTTAT GCAATATATG
CTTTACACCA GGTTGAAAGT GAATTAATAT AACAAAGAG ATTCCGAATA CGTTATATAC

-1000
CCTTAAGCAA ATGCCGAATC TGTTTTTTTT TTTTGTTATT GGATATTGAC TGAAAATAAG
GGAATTCGTT TACGGCTTAG ACAAAAAAAA AAAACAATAA CCTATAACTG ACTTTATTC

-950
GGGTTTTTC ACACTTGAAG ATCTCAAAAG AGAAAACTAT TACAACGGAA ATTCATTGTA
CCCAAAAAAG TGTGAACTTC TAGAGTTTTC TCTTTTGATA ATGTTGCCTT TAAGTAACAT

-900
AAAGAAGTGA TTAAGCAAAT TGAGCAAAGG TTTTTATGTG GTTTATTTCA TTATATGATT
TTTCTTCACT AATTCGTTTA ACTCGTTTCC AAAAATACAC CAAATAAAGT AATATACTAA

-850                                                      -800
GACATCAAAT TGTATATATA TGGTTGTTTT ATTTAACAAT ATATATGGAT ATAACGTACA
CTGTAGTTTA ACATATATAT ACCAACAAAA TAAATTGTTA TATATACCTA TATTGCATGT
```

Fig. 6a

```
                                                          -750
AACTAAATAT GTTTGATTGA CGAAAAAAAA TATATGTATG TTTGATTAAC AACATAGCAC
TTGATTTATA CAAACTAACT GCTTTTTTTT ATATACATAC AAACTAATTG TTGTATCGTG

-700
ATATTCAACT GATTTTTGTC CTGATCATCT ACAACTTAAT AAGAACACAC AACATTGAAA
TATAAGTTGA CTAAAAACAG GACTAGTAGA TGTTGAATTA TTCTTGTGTG TTGTAACTTT

-650
AAATCTTTGA CAAAATACTA TTTTTGGGTT TGAAATTTTG AATACTTACA ATTATTCTTC
TTTAGAAACT GTTTTATGAT AAAAACCCAA ACTTTAAAAC TTATGAATGT TAATAAGAAG

-600
TCGATCTTCC TCTCTTTCCT TAAATCCTGC GTACAAATCC GTCGACGCAA TACATTACAC
AGCTAGAAGG AGAGAAAGGA ATTTAGGACG CATGTTTAGG CAGCTGCGTT ATGTAATGTG

-550                                                     -500
AGTTGTCAAT TGGTTCTCAG CTCTACCAAA AACATCTATT GCCAAAAGAA AGGTCTATTT
TCAACAGTTA ACCAAGAGTC GAGATGGTTT TTGTAGATAA CGGTTTTCTT TCCAGATAAA

-450
GTACTTCACT GTTACAGCTG AGAACATTAA ATATAATAAG CAAATTTGAT AAAACAAAGG
CATGAAGTGA CAATGTCGAC TCTTGTAATT TATATTATTC GTTTAAACTA TTTTGTTTCC

-400
GTTCTCACCT TATTCCAAAA GAATAGTGTA AAATAGGGTA ATAGAGAAAT GTTAATAAAA
CAAGAGTGGA ATAAGGTTTT CTTATCACAT TTTATCCCAT TATCTCTTTA CAATTATTTT

-350
GGAAATTAAA AATAGATATT TTGGTTGGTT CAGATTTTGT TTCGTAGATC TACAGGGAAA
CCTTTAATTT TTATCTATAA AACCAACCAA GTCTAAAACA AAGCATCTAG ATGTCCCTTT

-300
TCTCCGCCGT CAATGCAAAG CGAAGGTGAC ACTTGGGGAA GGACCAGTGG TCCGTACAAT
AGAGGCGGCA GTTACGTTTC GCTTCCACTG TGAACCCCTT CCTGGTCACC AGGCATGTTA

-250                                                     -200
GTTACTTACC CATTTCTCTT CACGAGACGT CGATAATCAA ATTGTTTATT TTCATATTTT
CAATGAATGG GTAAAGAGAA GTGCTCTGCA GCTATTAGTT TAACAAATAA AAGTATAAAA

-150
TAAGTCCGCA GTTTTATTAA AAAATCATGG ACCCGACATT AGTACGAGAT ATACCAATGA
ATTCAGGCGT CAAAATAATT TTTTAGTACC TGGGCTGTAA TCATGCTCTA TATGGTTACT

-100
GAAGTCGACA CGCAAATCCT AAAGAAACCA CTGTGGTTTT TGCAAACAAG AGAAACCAGC
CTTCAGCTGT GCGTTTAGGA TTTCTTTGGT GACACCAAAA ACGTTTGTTC TCTTTGGTCG

-50
TTTAGCTTTT CCCTAAAACC ACTCTTACCC AAATCTCTCC ATAAATAAAG ATCCCGAGAC
AAATCGAAAA GGGATTTGG TGAGAATGGG TTTAGAGAGG TATTTATTTC TAGGGCTCTG

1
TCAAACACAA GTCTTTTTAT AAAGGAAAGA AAGAAAAACT TTCCTAATTG GTTCATACCA
AGTTTGTGTT CAGAAAAATA TTTCCTTTCT TCTTTTTGA AAGGATTAAC CAAGTATGGT 51                                                       101
AAGTCTGAGC TCTTCTTTAT ATCTCTCTTG TAGTTTCTTA TTGGGGGTCT TTGTTTTGTT
TTCAGACTCG AGAAGAAATA TAGAGAGAAC ATCAAAGAAT AACCCCCAGA AACAAAACAA

151
TGGTTCTTTT AGAGTAAGAA GTTTCTTAAA AAAGGATCAA AAATGGGAAG GGGTAGGGTT
```

Fig. 6b

```
ACCAAGAAAA TCTCATTCTT CAAAGAATTT TTTCCTAGTT TTTACCCTTC CCCATCCCAA

201
CAATTGAAGA GGATAGAGAA CAAGATCAAT AGACAAGTGA CATTCTCGAA AAGAAGAGCT
GTTAACTTCT CCTATCTCTT GTTCTAGTTA TCTGTTCACT GTAAGAGCTT TTCTTCTCGA

251
GGTCTTTTGA AGAAAGCTCA TGAGATCTCT GTTCTCTGTG ATGCTGAAGT TGCTCTTGTT
CCAGAAAACT TCTTTCGAGT ACTCTAGAGA CAAGAGACAC TACGACTTCA ACGAGAACAA

301
GTCTTCTCCC ATAAGGGGAA ACTCTTCGAA TACTCCACTG ATTCTTGGTA ACTTCAACTA
CAGAAGAGGG TATTCCCCTT TGAGAAGCTT ATGAGGTGAC TAAGAACCAT TGAAGTTGAT 351                                                     401
ATTCTTTACT TTTAAAAAAA TCTTTTAATC TGCTACTTTA TATAGTTTTT TTCCCCCTTA
TAAGAAATGA AAATTTTTTT AGAAAATTAG ACGATGAAAT ATATCAAAAA AAGGGGGAAT

451
AGTTGACTAC TTGATTTGCC CTAATTATTC ACTACTGCTT TTGTTATATA TTTTCTAGGG
TCAACTGATG AACTAAACGG GATTAATAAG TGATGACGAA AACAATATAT AAAAGATCCC

501
CTTCCATTTT TGGATTTTTT GATTAGCCAG AAAAATGTTT AATACAAATT TGTATAATTT
GAAGGTAAAA ACCTAAAAAA CTAATCGGTC TTTTACAAA TTATGTTTAA ACATATTAAA

551
AAAAATCAAA ACTTTAGGGC CGTAGTGAAG TGAACCCTAG AACACACAGA TTATACCATA
TTTTTAGTTT TGAAATCCCG GCATCACTTC ACTTGGGATC TTGTGTGTCT AATATGGTAT

601
GTAATTACCT TGATATATTG TGCAATATTT ATCAGCATCA TATCTTCAAA CTCAAGAGAT
CATTAATGGA ACTATATAAC ACGTTATAAA TAGTCGTAGT ATAGAAGTTT GAGTTCTCTA 651                                                     701
ATAGAAGGGT ATGTTAATCT TTGAACTAGG GTTTTGATCC CTAACTCATA ATGAATCCTT
TATCTTCCCA TACAATTAGA AACTTGATCC CAAAACTAGG GATTGAGTAT TACTTAGGAA

751
TTGTTCTCCA ATAGCCATGT CTTTCGAATT TGCAGATCTA AGCTCTAATT GATGCCATAG
AACAAGAGGT TATCGGTACA GAAAGCTTAA ACGTCTAGAT TCGAGATTAA CTACGGTATC

801
TAAGAAAATA AGATCTGTAG TTTTCACTCG CTCACTGAGT TCGAGTTTTA AATGAAGTGT
ATTCTTTTAT TCTAGACATC AAAAGTGAGC GAGTGACTCA AGCTCAAAAT TTACTTCACA

851
CGTTTCTTTT TTCATATATA GTTGCAACTG GATTATAATT AAAAAATATT ATGGGACGAG
GCAAAGAAAA AAGTATATAT CAACGTTGAC CTAATATTAA TTTTTTATAA TACCCTGCTC

901
AAAATAATTT AAAATAGATA TAGATAACAA TGTCAAATTG AGAATTTTTT ATTAGAAAGA
TTTTATTAAA TTTTATCTAT ATCTATTGTT ACAGTTTAAC TCTTAAAAAA TAATCTTTCT 951                                                    1001
ATATTTAACT TACGAGTTGT TTTTTTTCAG CTGTAAAAGA ATATCTAATT TGTTCTCACG
TATAAATTGA ATGCTCAACA AAAAAAGTC GACATTTCT TATAGATTAA ACAAGAGTGC

1051
ACTGTGTCTT CATGTTTTGC AAATCTAAGC AAAGAAAATG TTTAAACTCG GATCTTAAGA
TGACACAGAA GTACAAAACG TTTAGATTCG TTTCTTTTAC AAATTTGAGC CTAGAATTCT
```

Fig. 6c

```
                                 1101
TTATGAACTC GTAATATAAA ACACTATATA GTATTAAATT TGAACTAGTG TTGCTTCTTT
AATACTTGAG CATTATATTT TGTGATATAT CATAATTTAA ACTTGATCAC AACGAAGAAA

1151
TGCTACTTTG ACTTTAGAAA TTAAAACTGA AACAAAGATG TCAAATCTGA GTAGGGAGTC
ACGATGAAAC TGAAATCTTT AATTTTGACT TTGTTTCTAC AGTTTAGACT CATCCCTCAG

1201
TTTGACCTCT GGGGATCCAT AAAAAGAACT AACTCCATCC TAAAATCGGC TTCTTACCGA
AAACTGGAGA CCCCTAGGTA TTTTTCTTGA TTGAGGTAGG ATTTTAGCCG AAGAATGGCT 1251                                                  1301
TGGTCAAACT TAGCTCCAAC AAGCAACAGC TGTTCTTCTT TTTTTTTTTT TTTTTTTTTT
ACCAGTTTGA ATCGAGGTTG TTCGTTGTCG ACAAGAAGAA AAAAAAAAAA AAAAAAAAAA

1351
TTTAAGCATT GTCCTTGTTC TGAAAAAAAA TAAGATTGGT AAATTGGCAA GATTATAATA
AAATTCGTAA CAGGAACAAG ACTTTTTTTT ATTCTAACCA TTTAACCGTT CTAATATTAT

1401
ATTTATTATA ATGTGTCGCA CTAAGAAGAT TTTCTGTACC TAATTGTAGC AAAATTAAAG
TAAATAATAT TACACAGCGT GATTCTTCTA AAAGACATGG ATTAACATCG TTTTAATTTC

1451
AAACCGCAGT TAGAACTCGA AGCTAAGAGC ATAGGGTCTA TGATTCATAC TGTTTTGTTA
TTTGGCGTCA ATCTTGAGCT TCGATTCTCG TATCCCAGAT ACTAAGTATG ACAAAACAAT

1501
TTATAAAGGT ATCATAGAGA TCGGTACTTG ATTTGTTATA GGAAATCTTG GTTTAATTGC
AATATTTCCA TAGTATCTCT AGCCATGAAC TAAACAATAT CCTTTAGAAC CAAATTAACG 1551                                            1601
ATAAAACCAT CATTAGATTT ATCCTAAAAT GTGATGATAT TTTGGTCACA TCTCCATATT
TATTTTGGTA GTAATCTAAA TAGGATTTTA CACTACTATA AAACCAGTGT AGAGGTATAA

1651
ATTTATATAA TAAAATGATA ATTGGTTGAT GATAAAGCTA ACCCTAATTC TGTGAAATGA
TAAATATATT ATTTTACTAT TAACCAACTA CTATTTCGAT TGGGATTAAG ACACTTTACT

1701
TCAGTATGGA GAAGATACTT GAACGCTATG AGAGGTACTC TTACGCCGAA AGACAGCTTA
AGTCATACCT CTTCTATGAA CTTGCGATAC TCTCCATGAG AATGCGGCTT TCTGTCGAAT

1751
TTGCACCTGA GTCCGACGTC AATGTATTTC AATAAATATT TCTCCTTTTA ATCCACATAT
AACGTGGACT CAGGCTGCAG TTACATAAAG TTATTTATAA AGAGGAAAAT TAGGTGTATA

1801
ATATTATATC AATCTATTTG TAGTATTGAT GAATTTTATT TGTATAAAAC TTCTGGTACA
TATAATATAG TTAGATAAAC ATCATAACTA CTTAAAATAA ACATATTTTG AAGACCATGT 1851                                            1901
CAGACAAACT GGTCGATGGA GTATAACAGG CTTAAGGCTA AGATTGAGCT TTTGGAGAGA
GTCTGTTTGA CCAGCTACCT CATATTGTCC GAATTCCGAT TCTAACTCGA AAACCTCTCT

1951
AACCAGAGGT ACACATTTAC ACTCATCACA TTTCTATCTA GAAAATCGAT CGGGTTCCAT
TTGGTCTCCA TGTGTAAATG TGAGTAGTGT AAAGATAGAT CTTTTAGCTA GCCCAAGGTA

2001
TTTAAAGTAA GTTAAAATTC ATTGATGCTA TTGAAATTCA GGCATTATCT TGGGGAAGAC
```

Fig. 6d

```
                    AAATTTCATT CAATTTTAAG TAACTACGAT AACTTTAAGT CCGTAATAGA ACCCCTTCTG

2051
                    TTGCAAGCAA TGAGCCCTAA AGAGCTTCAG AATCTGGAGC AGCAGCTTGA CACTGCTCTT
                    AACGTTCGTT ACTCGGGATT TCTCGAAGTC TTAGACCTCG TCGTCGAACT GTGACGAGAA

2101
                    AAGCACATCC GCACTAGAAA AGTATTGCCT TCTGCTATTT CGTTGAACAT ATCTATATAA
                    TTCGTGTAGG CGTGATCTTT TCATAACGGA AGACGATAAA GCAACTTGTA TAGATATATT 2151                                                   2201
                    CTTAAACGTT TACAAGTGTT ATTATAATGT GAACATTGAA ATACATATGT GTATGTATCA
                    GAATTTGCAA ATGTTCACAA TAATATTACA CTTGTAACTT TATGTATACA CATACATAGT

2251
                    ATATATATAT CAGTAATCAA TATCAATTTG ATATGTCTAT AGGTTGGTTC GAATGTATGA
                    TATATATATA GTCATTAGTT ATAGTTAAAC TATACAGATA TCCAACCAAG CTTACATACT

2301
                    GTTATGTTGT GTATTTAAG ACTCCATATT ACTTAAAGTA ATGGGTTGTT AATGTTGATG
                    CAATACAACA CATAAAATTC TGAGGTATAA TGAATTTCAT TACCCAACAA TTACAACTAC

2351
                    TGTGTGTATG CAGAACCAAC TTATGTACGA GTCCATCAAT GAGCTCCAAA AAAAGGTATG
                    ACACACATAC GTCTTGGTTG AATACATGCT CAGGTAGTTA CTCGAGGTTT TTTTCCATAC

2401
                    TAAAACCCCT ATCAAATGTA TGTCTTATAG AGAAACGTAT AGGAAAGCTA ATTAACAATC
                    ATTTTGGGGA TAGTTTACAT ACAGAATATC TCTTTGCATA TCCTTTCGAT TAATTGTTAG 2451                                             2501
                    GTGCCGTTTC GGAAATGACA GGAGAAGGCC ATACAGGAGC AAAACAGCAT GCTTTCTAAA
                    CACGGCAAAG CCTTTACTGT CCTCTTCCGG TATGTCCTCG TTTTGTCGTA CGAAAGATTT

2551
                    CAGGTAACAC ATGTCATCAT TTCTCTTTCA TCAACATGTT GTCCATTGCA TTACTGTTAC
                    GTCCATTGTG TACAGTAGTA AAGAGAAAGT AGTTGTACAA CAGGTAACGT AATGACAATG

2601
                    CTTCCACTGT TCTGCTCCAC ACTTCCAGCC AAGCTATACC TACGATATCT TCATATCTCC
                    GAAGGTGACA AGACGAGGTG TGAAGGTCGG TTCGATATGG ATGCTATAGA AGTATAGAGG

2651
                    ACTTAACTTC GGCACCATTA AATAAAAATA GAAAATCTTT GCAAATTTGT TTGAAATAGC
                    TGAATTGAAG CCGTGGTAAT TTATTTTTAT CTTTTAGAAA CGTTTAAACA AACTTTATCG

2701
                    ATAGATGTTG TCTATTGATT GATATAATCA CCAGCCTGTA CGTAGATATG GTTTGTCCGT
                    TATCTACAAC AGATAACTAA CTATATTAGT GGTCGGACAT GCATCTATAC CAAACAGGCA 2751                                        2801
                    TTAGTTTTAA GGTGTCTCTC GGATTGAAAA TATTTTGAAA TCTTTTGAAA TGTTTGTCCC
                    AATCAAAATT CCACAGAGAG CCTAACTTTT ATAAAACTTT AGAAAACTTT ACAAACAGGG

2851
                    ATCATTCTTA CTTAGCTCAT ATCTATGTAT ATGAATATAG ACACTACTCC TAATTATAAA
                    TAGTAAGAAT GAATCGAGTA TAGATACATA TACTTATATC TGTGATGAGG ATTAATATTT

2901
                    ATGTTATAAT AGTTCATTGC ATGAGTGCAA CTGTGAAAAT AACTATTTGT AACCATTGCA
                    TACAATATTA TCAAGTAACG TACTCACGTT GACACTTTTA TTGATAAACA TTGGTAACGT
```

Fig. 6e

```
                2951
TATATATAGT TTCTTCACTT TGAAAATTGA TGATGATAAT ATGGTTTGAA ATAAATTTGC
ATATATATCA AAGAAGTGAA ACTTTTAACT ACTACTATTA TACCAAACTT TATTTAAACG

3001
TGGCAGATCA AGGAGAGGGA AAAAATTCTT AGGGCTCAAC AGGAGCAGTG GGATCAGCAG
ACCGTCTAGT TCCTCTCCCT TTTTTAAGAA TCCCGAGTTG TCCTCGTCAC CCTAGTCGTC 3051                                                  3101
AACCAAGGCC ACAATATGCC TCCCCCTCTG CCACCGCAGC AGCACCAAAT CCAGCATCCT
TTGGTTCCGG TGTTATACGG AGGGGGAGAC GGTGGCGTCG TCGTGGTTTA GGTCGTAGGA

3151
TACATGCTCT CTCATCAGCC ATCTCCTTTT CTCAACATGG GGTAACAAAA AATTACTAAT
ATGTACGAGA GAGTAGTCGG TAGAGGAAAA GAGTTGTACC CCATTGTTTT TTAATGATTA

3201
CAGTCTTAAT TTAAAGCACA TATGTTATGC AAGCTAGTTA CGTTAGGTGT TGTAATTTCA
GTCAGAATTA AATTTCGTGT ATACAATACG TTCGATCAAT GCAATCCACA ACATTAAAGT

3251
TTGAAGTTAT AGCTGTTAGT GATGGTTACA TGATGCTAGA TTTTGAAACT AGAAAACTTT
AACTTCAATA TCGACAATCA CTACCAATGT ACTACGATCT AAAACTTTGA TCTTTTGAAA

3301
ATTTTAAAAC ATTATTTTAT TAACGTAGGT TAATGCAATG GTCGCCAAAC GAACAAACTT
TAAAATTTTG TAATAAAATA ATTGCATCCA ATTACGTTAC CAGCGGTTTG CTTGTTTGAA 3351                                                  3401
ATTAGTGTGG AAAAATGTAC ATGGAATGGT TGCGAAAAGC CTAAGTCGAC TTTTGTTGTT
TAATCACACC TTTTTACATG TACCTTACCA ACGCTTTTCG GATTCAGCTG AAAACAACAA

3451
GTTGGTCTAT GTGTTTAAGT ACAATTTTAG TTTGTTAGAT AAATGAAATT AATATATCTT
CAACCAGATA CACAAATTCA TGTTAAAATC AAACAATCTA TTTACTTTAA TTATATAGAA

3501
TGACATTTCA CAATGGACTG ATATTTGATT TTCCTTTGTT GTACGGTGAA ACATATGATT
ACTGTAAAGT GTTACCTGAC TATAAACTAA AAGGAAACAA CATGCCACTT TGTATACTAA

3551
ACATATGCAC TTTCATATAT ATCCTATGTA TGATTGTGAA TGCAGTGGTC TGTATCAAGA
TGTATACGTG AAAGTATATA TAGGATACAT ACTAACACTT ACGTCACCAG ACATAGTTCT

3601
AGATGATCCA ATGGCAATGA GGAGGAATGA TCTCGAACTG ACTCTTGAAC CCGTTTACAA
TCTACTAGGT TACCGTTACT CCTCCTTACT AGAGCTTGAC TGAGAACTTG GGCAAATGTT

3651
CTGCAACCTT GGCTGCTTCG CCGCATGA
GACGTTGGAA CCGACGAAGC GGCGTACT
```

Fig. 6f

```
Sequence Range: -140 to 1080
                                                                   -91
             GAATTCGGCA CGAGAACTTT CCTAATTGGT TCATACCAAA GTCTGAGCTC TTCTTTATAT -41
             CTCTCTTGTA GTTTCTTATT GGGGGTCTTT GTTTTGTTTG GTTCTTTTAG AGTAAGAAGT 10
             TTCTTAAAAA AGGATCAAAA ATGGGAAGGG GTAGGGTTCA ATTGAAGAGG ATAGAGAACA
                                    M  G  R  G  R  V  Q  L  K  R  I  E  N>

60
             AGATCAATAG ACAAGTGACA TTCTCGAAAA GAAGAGCTGG TCTTTTGAAG AAAGCTCATG
             K  I  N  R  Q  V  T  F  S  K  R  R  A  G  L  L  K  K  A  H>

110                                                    160
             AGATCTCTGT TCTCTGTGAT GCTGAAGTTG CTCTTGTTGT CTTCTCCCAT AAGGGGAAAC
             E  I  S  V  L  C  D  A  E  V  A  L  V  V  F  S  H  K  G  K>

210
             TCTTCGAATA CTCCACTGAT TCTTGTATGG AGAAGATACT TGAACGCTAT GAGAGGTACT
             L  F  E  Y  S  T  D  S  C  M  E  K  I  L  E  R  Y  E  R  Y>

260
             CTTACGCCGA AAGACAGCTT ATTGCACCTG AGTCCGACGT CAATACAAAC TGGTCGATGG
             S  Y  A  E  R  Q  L  I  A  P  E  S  D  V  N  T  N  W  S  M>

310
             AGTATAACAG GCTTAAGGCT AAGATTGAGC TTTTGGAGAG AAACCAGAGG CATTATCTTG
             E  Y  N  R  L  K  A  K  I  E  L  L  E  R  N  Q  R  H  Y  L>

360
             GGGAAGACTT GCAAGCAATG AGCCCTAAAG AGCTTCAGAA TCTGGAGCAG CAGCTTGACA
             G  E  D  L  Q  A  M  S  P  K  E  L  Q  N  L  E  Q  Q  L  D>

410                                                    460
             CTGCTCTTAA GCACATCCGC ACTAGAAAAA ACCAACTTAT GTACGAGTCC ATCAATGAGC
             T  A  L  K  H  I  R  T  R  K  N  Q  L  M  Y  E  S  I  N  E>

510
             TCCAAAAAAA GGAGAAGGCC ATACAGGAGC AAAACAGCAT GCTTTCTAAA CAGATCAAGG
             L  Q  K  K  E  K  A  I  Q  E  Q  N  S  M  L  S  K  Q  I  K>

560
             AGAGGGAAAA AATTCTTAGG GCTCAACAGG AGCAGTGGGA TCAGCAGAAC CAAGGCCACA
             E  R  E  K  I  L  R  A  Q  Q  E  Q  W  D  Q  Q  N  Q  G  H>

610
             ATATGCCTCC CCCTCTGCCA CCGCAGCAGC ACCAAATCCA GCATCCTTAC ATGCTCTCTC
             N  M  P  P  P  L  P  P  Q  Q  H  Q  I  Q  H  P  Y  M  L  S>

660
             ATCAGCCATC TCCTTTTCTC AACATGGGTG GTCTGTATCA AGAAGATGAT CCAATGGCAA
             H  Q  P  S  P  F  L  N  M  G  G  L  Y  Q  E  D  D  P  M  A>

710                                                    760
             TGAGGAGGAA TGATCTCGAA CTGACTCTTG AACCCGTTTA CAACTGCAAC CTTGGCTGCT
             M  R  R  N  D  L  E  L  T  L  E  P  V  Y  N  C  N  L  G  C>

TCGCCGCATG AAGCATTTCC ATATATATAT ATTTGTAATC GTCAACAATA AAAACAGTTT
             F  A  A  *
                                                      860
             GCCACATACA TATAAATAGT GGCTAGGCTC TTTTCATCCA ATTAATATAT TTTGGCAAAT

910
             GTTCGATGTT CTTATATCAT CATATATAAA TTAGCAGGCT CCTTTCTTCT TTTGTAATTT
```

Fig. 8a

```
                     960
GATAAGTTTA TTTGCTTCAA TATGGAGCAA AATTGTAATA TATTTGAAGG TCAGAGAGAA 1010                                                    1060
TGAACGTGAA CTTAATAGAA AAAAAAAAAA AAAAAAAAAA AAAAAAAAAA AAAAAAAACC

CGACGTAGCT CGAGGAATTC
```

Fig. 8b

Sequence Range: -346 to 1028

```
                                                      -297
GAATTCCGGA TTCACAAAAA CTTTTCTTCA GATTCACAAT CTCATCACAA CCCTTCAAAA

-247
AGAGAAAAGA TCTAAAGAAT AAACAAGAGC CCTAATATCA AATCACAACC AAAAAAACCA

-197
AAGAAAGCTA ATTAAAGTTT TCTCTCTAGC TATTCCTCTT CTTTTCTTGT TCTTGAAAAC

-147
TAGGGTTTAC TTCACCAAAA GATAAGATCT TTCCCCAGAA AAAGCAATAC CCAAGTCATG

-97                                                   -47
TTTCTGTGTG TCTGTATATA GATAAAACAT TACATACCCT AATAAGGTTA CACAAATAGC

4
TATAAAAGAG GGAAAATAAG ATAGGGATTT TTTGGGGTGA GGAAAGATGG GAAGAGGAAG
                                              M   G   R   G   R>

54
AGTAGAGCTC AAGAGGATAG AGAACAAAAT CAACAGACAA GTGACGTTTG CTAAACGTAG
  V   E   L   K   R   I   E   N   K   I   N   R   Q   V   T   F   A   K   R   R>

AAATGGTTTG CTGAAAAAAG CTTATGAGCT TTCTGTTCTC TGCGATGCTG AAGTCTCTCT
  N   G   L   L   K   K   A   Y   E   L   S   V   L   C   D   A   E   V   S   L>

154
CATCGTCTTC TCCAACCGTG GCAAGCTCTA CGAGTTCTGC AGCACCTCCA ACATGCTCAA
  I   V   F   S   N   R   G   K   L   Y   E   F   C   S   T   S   N   M   L   K>

204                                         254
GACACTGGAA AGGTATCAGA AGTGTAGCTA TGGCTCCATT GAAGTCAACA ACAAACCTGC
  T   L   E   R   Y   Q   K   C   S   Y   G   S   I   E   V   N   N   K   P   A>

304
TAAAGAGCTT GAGAACAGCT ACAGAGAGTA CTTGAAGCTG AAAGGTAGAT ATGAAAATCT
  K   E   L   E   N   S   Y   R   E   Y   L   K   L   K   G   R   Y   E   N   L>

354
GCAACGTCAG CAGAGAAATC TTCTTGGAGA GGATCTTGGA CCTCTGAATT CAAAGGAGCT
  Q   R   Q   Q   R   N   L   L   G   E   D   L   G   P   L   N   S   K   E   L>

404
AGAGCAGCTT GAGCGTCAAC TAGACGGCTC TCTGAAGCAA GTTCGCTGCA TCAAGACACA
  E   Q   L   E   R   Q   L   D   G   S   L   K   Q   V   R   C   I   K   T   Q>

454
GTATATGCTT GACCAGCTCT CTGATCTTCA AGGTAAGGAG CATATCTTGC TTGATGCCAA
  Y   M   L   D   Q   L   S   D   L   Q   G   K   E   H   I   L   L   D   A   N>

504                                                 554
CAGAGCTTTG TCAATGAAGC TGGAAGATAT GATCGGCGTG AGACATCACC ATATAGGAGG
  R   A   L   S   M   K   L   E   D   M   I   G   V   R   H   H   H   I   G   G>

604
AGGATGGGAA GGTGGTGATC AACAGAATAT TGCCTATGGA CATCCTCAGG CTCATTCTCA
  G   W   E   G   G   D   Q   Q   N   I   A   Y   G   H   P   Q   A   H   S   Q>

654
GGGACTATAC CAATCTCTTG AATGTGATCC CACTTTGCAA ATTGGATATA GCCATCCAGT
  G   L   Y   Q   S   L   E   C   D   P   T   L   Q   I   G   Y   S   H   P   V>

704
GTGCTCAGAG CAAATGGCTG TGACGGTGCA AGGTCAGTCC CAACAAGGAA ACGGCTACAT
  C   S   E   Q   M   A   V   T   V   Q   G   Q   S   Q   Q   G   N   G   Y   I>
```

Fig. 10a

```
                             754
CCCTGGCTGG ATGCTGTGAG CGATACTTCT TCCCCCAATA AAGATCTTAA GCAAGTACTG
   P    G     W    M    L    *

804                                                      854
GTGGGGTCTT CGTGGTGTGA TCTTAGATCT TATGCATATG AATAATAATG TTATTGCACA

904
AGACTTTTGC TTTTGTAGAC ACAAGTGGCT ATAGCTGTAA TAGCCTTCAA CATCTCTCTT

954
CTGTTTCAGG ATTTGTTTGT GCCTATTGTA ATTGCTTATA TATGTATGGT TTGTATAATG

1004
TGTGAAATGT TAACATCGAC CATGTCTCAT CTGGTGAAAA AAAAAAAAAA AAAA
```

Fig. 10b

Sequence Range: -395 to 908

```
                                                                -346
           GAATTCCGGC CCTCACACAT TTCTTATCTT TTGCTCTCAA TAGATTCCAT TGATTCAAAA
                                            -296
           CAAAATTTTC ATTAAGATTT CACAACCTCC ACACACTTCC AAACACAATT AAAGAGAGGA
                                -246
           AAAAGAATCA ATAACCCTAT AAATAAAAAA TCAGACAAAC AGAAGTTTCC TCTTCTTCTT
                     -196
           CCTTAAGCTA GTACCTTTTG TTCTTGAAAT TAGGGTTAAT TTCTTTTTTC CAAATACCAT
                -146                                                    -96
           CAATTCTCCA GACCATAAAA ACTCAAAAAG ATCAGATCTT TCCTCTGAAA AAGAGATACC
                                                        -46
           CAACTTATGT TTTTGTGTGT CTGTATATAG ATAAACATTA CATACCCATA TTTGTGTATA
                                            5
           GACATAAAAA GTGGAAATTA AGGTAACAAA AAGAAATGGG AAGAGGAAGA GTAGAGCTGA
                                                   M   G   R   G   R   V   E   L>
                                55
           AGAGGATAGA GAACAAAATC AACAGACAAG TAACGTTTGC AAAGCGTAGG AACGGTTTGT
             K  R  I  E   N  K  I   N  R  Q   V  T  F   A  K  R   N  G  L>
                                                    105
           TGAAGAAAGC TTATGAATTG TCTGTTCTCT GTGATGCTGA AGTTGCTCTC ATCATCTTCT
             L  K  K  A   Y  E  L   S  V  L   C  D  A  E   V  A  L   I  I  F>
                     155                                                205
           CCAACCGTGG AAAGCTCTAT GAGTTTTGCA GCTCCTCAAA CATGCTCAAG ACACTTGATC
             S  N  R  G   K  L  Y   E  F  C   S  S  S  N   M  L  K   T  L  D>
                                                      255
           GGTACCAGAA ATGCAGCTAT GGATCCATTG AAGTCAACAA CAAACCTGCC AAAGAACTTG
             R  Y  Q  K   C  S  Y   G  S  I   E  V  N  N   K  P  A   K  E  L>
                                                305
           AGAACAGCTA CAGAGAATAT CTGAAGCTTA AGGGTAGATA TGAGAACCTT CAACGTCAAC
             E  N  S  Y   R  E  Y   L  K  L   K  G  R  Y   E  N  L   Q  R  Q>
                                355
           AGAGAAATCT TCTTGGGGAG GATTTAGGAC CTTTGAATTC AAAGGAGTTA GAGCAGCTTG
             Q  R  N  L   L  G  E   D  L  G   P  L  N  S   K  E  L   E  Q  L>
                           405
           AGCGTCAACT GGACGGCTCT CTCAAGCAAG TTCGGTCCAT CAAGACACAG TACATGCTTG
             E  R  Q  L   D  G  S   L  K  Q   V  R  S  I   K  T  Q   Y  M  L>
                 455                                              505
           ACCAGCTCTC GGATCTTCAA AATAAAGAGC AAATGTTGCT TGAAACCAAT AGAGCTTTGG
             D  Q  L  S   D  L  Q   N  K  E   Q  M  L  L   E  T  N   R  A  L>
                                                     555
           CAATGAAGCT GGATGATATG ATTGGTGTGA GAAGTCATCA TATGGGAGGA TGGGAAGGCG
             A  M  K  L   D  D  M   I  G  V   R  S  H  H   M  G  G   W  E  G>
                                             605
           GTGAACAGAA TGTTACCTAC GCGCATCATC AAGCTCAGTC TCAGGGACTA TACCAGCCTC
             G  E  Q  N   V  T  Y   A  H  H   Q  A  Q  S   Q  G  L   Y  Q  P>
                                       655
           TTGAATGCAA TCCAACTCTG CAAATGGGGT ATGATAATCC AGTATGCTCT GAGCAAATCA
             L  E  C  N   P  T  L   Q  M  G   Y  D  N  P   V  C  S   E  Q  I>
```

Fig. 11a

```
                        705
CTGCGACAAC ACAAGCTCAG GCGCAGCCGG GAAACGGTTA CATTCCAGGA TGGATGCTCT
 T  A  T  T  Q  A  Q   A  Q  P   G  N  G  Y   I  P  G   W  M  L>
           755                                                   805
GAGAATCATG TACTGTGATG AAGCTCACCC ACAAAAGACC TTATATATAT ATAAAGTATA
 *

GATACAAGAC TTGGATTTGT AGACATAAGT GGCTAATATA ATGGTCCTGA GGATCTTCTA
                                905
GACATTTGTA TCTTTTGGGA ATCCTTGCTT ATATTAAGAA TTC
```

Fig. 11b

METHODS OF SUPPRESSING FLOWERING IN TRANSGENIC PLANTS

STATEMENT AS TO RIGHTS TO INVENTIONS MADE UNDER FEDERALLY SPONSORED RESEARCH OR DEVELOPMENT

This invention was made with Government support of Grant Nos. IBN9418436 and IBN9018749 awarded by the National Science Foundation. The Government has certain rights in this invention.

FIELD OF THE INVENTION

The present invention relates generally to plant molecular biology and genetic engineering and more specifically to the production of genetically modified plants in which the natural process of flowering is suppressed.

BACKGROUND INFORMATION

The ecological and economic importance of wood is difficult to overstate, with the total amount of wood in the world's forests estimated at about 1.5 Gt. Thus, wood is by far the most abundant component of the terrestrial biomass. The carbon stored in wood and humus (partially degraded wood) is important in the planetary carbon cycle, which has a significant influence on global climate. In addition, wood is a leading industrial component of the global economy. About 4% of the US gross national product has been attributed to the wood products industry in past decades.

Unfortunately, a growing population is reducing the arable land area in the United States and around the world, while the demand for wood products increases. This growing demand and limited resources have resulted in a need for greater productivity of the remaining forest lands.

The flowering process consumes 25 to 35% of the energy of a typical plant, thereby limiting wood production. Thus, for trees used for lumber or pulp production, for example, it can be advantageous to suppress flowering in order increase the yield of wood. Suppression of flowering also can be desired to eliminate the production of allergic pollen, or to prevent pollen dissemination. Unfortunately, methods of producing genetically modified plants in which flowering is suppressed without effecting other desirable traits are not currently available.

Thus, a need exists for developing genetically modified plant varieties in which the natural process of flowering is suppressed. The present invention satisfies this need and provides related advantages as well.

SUMMARY OF THE INVENTION

The present invention provides a transgenic plant characterized by suppressed flowering. The transgenic plant contains a nucleic acid molecule including a floral organ selective regulatory element operatively linked to a nucleotide sequence encoding a cytotoxic gene product, wherein the nucleic acid molecule is heritable by progeny thereof.

The transgenic plant contains a nucleic acid molecule including a floral organ selective regulatory element operatively linked to a nucleotide sequence encoding a cytotoxic gene product, where the floral organ selective regulatory element is an AGL2 regulatory element, an AGL4 regulatory element or an AGL9 regulatory element, or a AP1 regulatory element, and wherein the nucleic acid molecule is heritable by progeny thereof.

In a transgenic plant of the invention, the floral organ selective regulatory element can be, for example, an AGL2 regulatory element having substantially the nucleotide sequence of *Arabidopsis* AGL2 promoter SEQ ID NO:1, or an active fragment thereof. A floral organ selective regulatory element useful in a transgenic plant of the invention also can be, for example, an AGL4 regulatory element such as an AGL4 regulatory element having substantially the nucleotide sequence of *Arabidopsis* AGL4 promoter SEQ ID NO:2, or an active fragment thereof. A floral organ selective regulatory element also can be an AGL9 regulatory element such as an AGL9 regulatory element having substantially the nucleotide sequence of *Arabidopsis* AGL9 promoter SEQ ID NO:3, or an active fragment thereof. A floral organ selective regulatory element also can be an AP1 regulatory element such as an AP1 regulatory element having substantially the nucleotide sequence of *Arabidopsis* AP1 promoter SEQ ID NO:10, or an active fragment thereof.

DNA sequences encoding a variety of encoded cytotoxic gene products can be used to produce a transgenic plant of the invention, including DNA encoding toxic peptides such as the diphtheria toxin A chain, RNase T1, Barnase RNase, ricin toxin A chain or the herpes simplex virus thymidine kinase (tk) gene product.

The invention further relates to regenerated fertile seedlings and mature plants obtained from transgenic seed or from the vegetative reproduction of transgenic plants, and R1 and subsequent generations, produced by sexual propagation or vegetative reproduction.

The description of the invention hereafter refers to *Arabidopsis thaliana*, when necessary for the sake of example. However, it should be noted that the invention is not limited to genetic transformation of plants such as *Arabidopsis*. The method of the present invention is capable of being practiced for other plant species, including for example, other angiosperm, and other gymnosperm forest plant species, legumes, grasses, other forage crops and the like. Particularly useful transgenic plants can be perennial woody plants such as Eucalyptus, cottonwood, birch, alder, Douglas fir, hemlock, pine and spruce.

The present invention also provides a tissue derived from a transgenic plant characterized by suppressed flowering and containing a nucleic acid molecule including a floral organ selective regulatory element operatively linked to a nucleotide sequence encoding a cytotoxic gene product, wherein the nucleic acid molecule is heritable by progeny thereof.

The present invention further provides tissue derived from a transgenic plant characterized by suppressed flowering and containing a nucleic acid molecule including a floral organ selective regulatory element operatively linked to a nucleotide sequence encoding a cytotoxic gene product, where the floral organ selective regulatory element is an AGL2 regulatory element, an AGL4 regulatory element or an AGL9 regulatory element, or an API regulatory element, wherein the nucleic acid molecule is heritable by progeny thereof. A tissue derived from a transgenic plant of the invention can be, for example, a tissue that is capable of vegetative or non-vegetative propagation, or plant cells, plant parts and seed.

The invention additionally is directed to all products derived from transgenic plants, plant cells, plant parts and seeds, which contain a nucleic acid molecule including a floral organ selective regulatory element operatively linked to a nucleotide sequence encoding a cytotoxic gene product, wherein the nucleic acid molecule is heritable by progeny thereof.

The invention also is directed to all products derived from transgenic plants, plant cells, plant parts and seeds, which contain a nucleic a nucleic acid molecule including a floral organ selective regulatory element operatively linked to a nucleotide sequence encoding a cytotoxic gene product, where the floral organ selective regulatory element is an AGL2 regulatory element, an AGL4 regulatory element or an AGL9 regulatory element, or an AP1 regulatory element, wherein the nucleic acid molecule is heritable by progeny thereof.

Also provided by the present invention is a method of producing a fertile, transgenic plant characterized by suppressed flowering. The method is based upon transformation of plant material, selection, plant regeneration, and conventional or propagation breeding techniques.

The method includes the step of introducing into a plant an exogenous nucleic acid molecule containing a floral organ selective regulatory element operatively linked to a nucleotide sequence encoding a cytotoxic gene product (a peptide), wherein the nucleic acid molecule is heritable by asexual or sexually obtained progeny thereof. The method includes the step of introducing into a plant an exogenous nucleic acid molecule containing a floral organ selective regulatory element operatively linked to a nucleotide sequence encoding a cytotoxic gene product, where flowering is suppressed due to selective expression of the exogenous nucleic acid molecule and where the floral organ selective regulatory element is preferably an AGL2 regulatory element, an AGL4 regulatory element or an AGL9 regulatory element, or the AP1 regulatory element.

The present invention also provides an isolated nucleic acid molecule including an AGL2, AGL4 or AGL9 or AP1 regulatory element, which confers selective expression upon an operatively linked nucleotide sequence (structural gene) in one or more floral organs of a plant.

The isolated nucleic acid molecule can further include, if desired, an operatively linked nucleotide sequence encoding a cytotoxic gene product. The encoded cytotoxic gene product can be one of a variety of cytotoxic gene products such as the peptides diphtheria toxin A chain, RNase T1, Barnase RNase, ricin toxin A chain or herpes simplex virus thymidine kinase gene product.

The present invention also provides a kit for producing a transgenic plant characterized by suppressed flowering. A kit of the invention comprises packaging containing a plant expression vector comprising a floral organ selective regulatory element operatively linked to a nucleotide sequence encoding a cytotoxic gene product, and instructions for transforming a susceptible plant with said vector.

BRIEF DESCRIPTION OF THE DRAWINGS

FIG. 1a through 1e shows the *Arabidopsis* AGL2 promoter SEQ ID NO:1.

FIGS. 2a through 2f shows the *Arabidopsis* AGL4 promoter SEQ ID NO:2.

FIGS. 3a through 3q shows the *Arabidopsis* AGL9 promoter SEQ ID NO:3.

FIG. 4 shows the nucleotide (SEQ ID NO:4) and amino acid sequence (SEQ ID NO:5) of the AGL2 cDNA and the nucleotide (SEQ ID NO:6) and amino acid sequence (SEQ ID NO:7) of the AGL4 cDNA. The AGL2 sequences are shown above the AGL4 sequences.

FIG. 5 shows the nucleotide (SEQ ID NO:8) and deduced amino acid sequence (SEQ ID NOS:9–11) of the AGL9 cDNA.

FIGS. 6a through 6f shows the *Arabidopsis* AP1 promoter SEQ ID NO:12.

FIGS. 8a through 8b shows the nucleotide (SEQ ID NO:13) and deduced amino acid sequence (SEQ ID NO:14) of the AP1 cDNA.

FIGS. 10a through 10b shows the nucleotide (SEQ ID NO:15) and amino acid sequence (SEQ ID NO:7) of the AGL4 cDNA.

FIGS. 11a through 11b shows the nucleotide (SEQ ID NO:16) and amino acid sequence (SEQ ID NO:5) of the AGL2 cDNA.

DETAILED DESCRIPTION OF THE INVENTION

Figure 9:
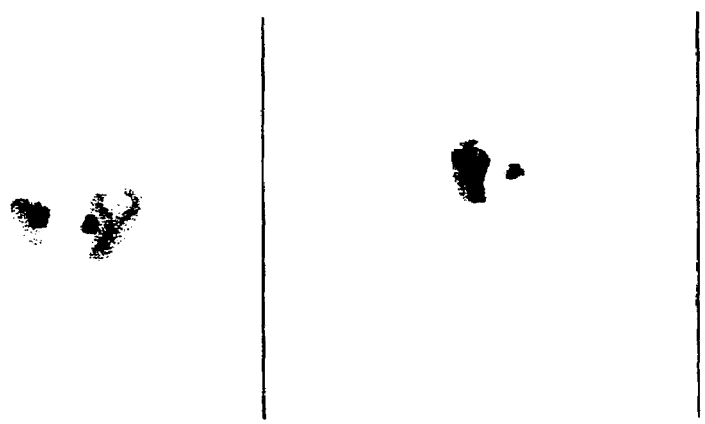
FIG. 9 shows GUS expression in 2 representative AP1 reporter lines. GUS activity is flower specific and GUS staining pattern largely mimics AP1 RNA accumulation pattern.

Flowering is often desirable and is the natural mechanism by which flowering plants propagate. Yet for some applications, it can be desirable to suppress flower and seed production. For example, in trees grown for lumber or pulp, wood yield can be increased by suppressing flower and seed production, which normally consumes 25 to 35% of the energy of a typical plant. Where allergic pollens are a concern, non-flowering varieties are desirable to avoid pollen dissemination. Furthermore, flowering can hasten senescence; thus, non-flowering transgenic plants can have improved longevity.

The present invention provides transgenic plants characterized by suppressed flowering. In a transgenic plant of the invention, a regulatory element that directs selective expression in one or more floral organs is used to control expression of an inhibitory or cytotoxic peptide such as diphtheria toxin or ricin. The selectively expressed cytotoxic gene product destroys floral tissue, thereby suppressing flowering, but is not expressed significantly in vegetative or other tissues and so has no deleterious effect outside the floral tissue.

A fertile transgenic plant of the invention contains a nucleic acid molecule including a floral organ selective regulatory element operatively linked to a nucleotide sequence encoding a cytotoxic gene product, wherein the nucleic acid molecule is heritable by progeny thereof. A fertile transgenic plant of the invention contains a nucleic acid molecule including a floral organ selective regulatory element operatively linked to a nucleotide sequence encoding a cytotoxic gene product, the floral organ selective regulatory element is an AGL2 regulatory element, an AGL4 regulatory element or an AGL9 regulatory element or an AP1 regulatory element, wherein the nucleic acid molecule is heritable by progeny thereof.

"Transgenic" is used herein to include any cell, cell line, callus, tissue, plant part or plant, the genotype of which has been altered beneficially by the presence of heterologous DNA that was introduced into the genotype by a process of genetic engineering, or which was initially introduced into the genotype of a parent plant by such a process and is subsequently transferred to later generations by sexual or asexual cell crosses or cell divisions. As used herein, "genotype" refers to the sum total of genetic material within a cell, either chromosomally, or extrachromosomally borne. Therefore, the term "transgenic" as used herein does not encompass the alteration of the genotype of any plant by conventional plant breeding methods or by naturally occurring events such as random cross-fertilization or spontaneous mutation.

The term "transgenic" may be used herein to describe a plant that contains an exogenous nucleic acid molecule or chimeric nucleic acid construct, which can be derived from an orthologous or heterologous plant or can originate from an animal or virus.

The term "exogenous," as used herein in reference to a nucleic acid molecule and a transgenic plant, means a nucleic acid molecule that is not native to the plant or that is present in the genome in other than its native association. An exogenous nucleic acid molecule can have a naturally occurring or non-naturally occurring nucleotide sequence and can be orthologous or heterologous to the plant species into which it is introduced.

The term "heritable" refers to the fact that the nucleic acid molecule is capable of transmission through a complete sexual cycle of a plant, i.e., it is passed from one plant through its gametes to progeny plants in the same manner as occurs in normal plants, or the nucleic acid can be transmitted via asexual propagation of cuttings or shoots.

The term "operatively linked," as used in reference to a regulatory element and a nucleotide sequence encoding a cytotoxic gene product, means that the regulatory element is linked so that it confers regulated expression upon the operatively linked nucleotide sequence. Thus, the term "operatively linked," as used in reference to a floral organ selective regulatory element and a nucleotide sequence encoding a cytotoxic gene product, means that the floral organ selective regulatory element is linked to the nucleotide sequence encoding the cytotoxic gene product so that the expression pattern of the floral organ selective regulatory element is conferred upon the nucleotide sequence encoding the cytotoxic gene product. It is recognized that a regulatory element and a nucleotide sequence that are operatively linked have, at a minimum, all elements essential for transcription, including, for example, a TATA box.

The term "suppressed," as used herein in reference to the flowering of a transgenic plant of the invention, means a significantly diminished extent of flowering as compared to the extent of flowering in a corresponding plant lacking a nucleic acid molecule containing a floral organ selective regulatory element operatively linked to a nucleotide sequence encoding a cytotoxic gene product. Thus, the term "suppressed" is used broadly to encompass both flowering that is significantly reduced as compared to the flowering in a corresponding non-transgenic plant, and to flowering that is completely precluded. In view of the above, one skilled in the art recognizes that a transgenic plant of the invention can be completely sterile or can be characterized by reduced fertility although generally flowering is suppressed to the extent that the transgenic plant is completely sterile.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

As used herein, the term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of human MCP-1.

As used herein, the term "flowering" is used broadly to refer not only to the traditional flowering of angiosperms but also to the normal reproductive development of other plants such as conifers.

It is recognized that there can be natural variation in the extent of flowering within a plant species or variety. However, a "suppression" in flowering in a transgenic plant of the invention readily can be identified by sampling a population of the corresponding plants, such as wild type plants, and determining that the normal distribution of flowering is significant diminished, on average, as compared to the normal distribution of flowering in a population of the corresponding plant species or variety that does not have a nucleic acid molecule containing a floral organ selective regulatory element operatively linked to a nucleotide sequence encoding a cytotoxic gene product. Thus, production of transgenic plants of the invention provides a means to skew the extent of normal flowering, such that flowering is diminished, on average, at least about 1%, 2%, 5%, 10%, 30%, 50% or 100% as compared to flowering in the corresponding plant species that does not have a nucleic acid molecule containing a floral organ selective regulatory element operatively linked to a nucleotide sequence encoding a cytotoxic gene product.

As used herein, the term "cytotoxic gene product" means a gene product, usually a peptide, that inhibits the growth of, or causes the death of, the cell in which it is expressed. Preferably, a cytotoxic gene product does not result in the death of cells other than the cell in which it is expressed. Thus, expression of a cytotoxic gene product from a floral organ selective regulatory element can be used to ablate cells within one or more floral organs without disturbing neighboring cells. A variety of cytotoxic gene products useful in plants are known in the art including toxins and enzymes, for example, diphtheria toxin A chain polypeptides; RNase T1; Barnase RNase; ricin toxin A chain polypeptides; and herpes simplex virus thymidine kinase (tk) gene products. While the diphtheria toxin A chain, RNase T1 and Barnase RNase are preferred cytotoxic gene products, or multiple nucleotide sequences encoding other cytotoxic gene products, can be used with a floral organ selective regulatory element to generate a transgenic plant of the invention characterized by suppressed flowering.

Diphtheria toxin is the naturally occurring toxin of *Corynebacterium diphtheriae*, which catalyzes the ADP-ribosylation of elongation factor 2, resulting in inhibition of protein synthesis and consequent cell death (Collier, *Bacteriol. Rev.* 39:54–85 (1975)). A single molecule of the fully active toxin is sufficient to kill a cell (Yamaizumi et al., *Cell* 15:245–250 (1978)). Diphtheria toxin has two subunits: the diphtheria toxin B chain directs internalization to most eukaryotic cells through a specific membrane receptor, whereas the A chain encodes the toxic catalytic domain. The catalytic DT-A chain does not include a signal peptide and is not secreted. Further, any DT-A released from dead cells in the absence of the diphtheria toxin B chain is precluded from cell attachment. Thus, DT-A is cell autonomous and directs killing only of the cells in which it is expressed without apparent damage to neighboring cells. The DT-A expression cassette of Palmiter et al., which contains the 193 residues of the A chain engineered with a synthetic ATG and lacking the native leader sequence, is particularly useful in the transgenic plants of the invention (Palmiter et al., *Cell* 50:435–443 (1987); Greenfield et al., *Proc, Natl. Acad. Sci., USA* 80:6853–6857 (1983), each of which is incorporated herein by reference).

RNase TI of *Aspergillus oryzae* and Barnase RNase of *Bacillus* amylolique-faciens also are cytotoxic gene products useful in the transgenic plants of the invention (Thorsness and Nasrallah, *Methods in Cell Biology* 50:439–448 (1995)). Barnase RNase may be more generally toxic to plants than RNase Ti and, thus, is preferred in the methods of the invention.

Ricin, a ribosome-inactivating protein produced by castor bean seeds, also is a cytotoxic gene product useful in a transgenic plant of the invention. The ricin toxin A chain polypeptide can be used to direct cell-specific ablation as described, for example, in Moffat et al., *Development* 114: 681–687 (1992). Plant ribosomes are variably susceptible to the plant-derived ricin toxin. The skilled person understands that the toxicity of ricin depends is variable and should be assessed for toxicity in the plant species of interest (see Olsnes and Pihl, *Molecular Action of Toxins and Viruses*, pages 51–105, Amsterdam: Elsevier Biomedical Press (1982)).

The present invention relates to the use of floral organ selective regulatory elements derived from AGL2, AGL4 or AGL9, which are "A GMOUS-LIKE" or "AGL" genes. AGAMOUS (AG) is a floral organ identity gene, one of a related family of transcription factors that, in various combinations, specify the identity of the floral organs: the petals, sepals, stamens and carpels (Bowman et al., *Devel.* 112:1–20 (1991); Weigel and Meyerowitz, *Cell* 78:203–209 (1994); Yanofsky, *Annual Rev. Plant Physiol. Mol. Biol.* 46:167–188 (1995)). The AGAMOUS gene product is essential for specification of carpel and stamen identity (Bowman et al., *The Plant Cell* 1:37–52 (1989); Yanofsky et al., *Nature* 346:35–39 (1990)). Related genes have recently been identified and denoted "AGAMOUS-LIKE" or "AGL" genes (Ma et al., *Genes Devel.* 5:484–495 (1991); Mandel and Yanofsky, *The Plant Cell* 7:1763–1771 (1995), which is incorporated herein by reference).

AGL2, AGL4 and AGL9, like AGAMOUS and other AGL genes, are characterized, in part, in that each is a plant MADS box gene. The plant MADS box genes generally encode proteins of about 260 amino acids including a highly conserved MADS domain of about 56 amino acids (Riechmann and Meyerowitz, *Biol. Chem.* 378:1079–1101 (1997), which is incorporated herein by reference). The MADS domain, which was first identified in the *Arabidopsis* AGAMOUS and *Antirrhimum majus* DEFICIENS genes, is conserved among transcription factors found in humans (serum response factor; SRF) and yeast (MCM1; Norman et al., *Cell* 55:989–1003 (1988); Passmore et al., *J. Mol. Biol.* 204: 593–606 (1988), and is the most highly conserved region of the MADS domain proteins. The MADS domain is the major determinant of sequence specific DNA-binding activity and can also perform dimerization and other accessory functions (Huang et al., *The Plant Cell* 8:81–94 (1996)). The MADS domain frequently resides at the amino-terminus, although some proteins contain additional residues amino-terminal to the MADS domain.

The "intervening domain" or "I-domain," located immediately C-terminal to the MADS domain, is a weakly conserved domain having a variable length of approximately 30 amino acids (Purugganan et al., *Genetics* 140:345–356 (1995)). In some proteins, the I-domain plays a role in the formation of DNA-binding dimers. A third domain present in plant MADS domain proteins is a moderately conserved 70 amino acid region denoted the "keratin-like domain" or "K-domain." Named for its similarity to regions of the keratin molecule, the structure of the K-domain appears capable of forming amphipathic helices and may mediate protein—protein interactions (Ma et al., *Genes Devel* 5:484–495 (1991)). The most variable domain, both in sequence and in length, is the carboxy-terminal or "C-domain" of the MADS domain proteins. Dispensable for DNA binding and protein dimerization in some MADS domain proteins, the function of the C-domain remains unknown.

The amino acid sequence of *Arabidopsis* AGL2, a protein with a calculated molecular mass of about 28.5 kDa, is shown in FIGS. 4 and 11*a* through 11*b*. Like other AGAMOUS-LIKE proteins, AGL2 has a highly conserved MADS domain and a K domain (Ma et al., *Genes Devel* 5:484–495 (1991). RNA dot blot hybridization was used to analyze AGL2 expression in immature seed pods, flowers, stems, and leaves. AGL2 RNA was preferentially expressed in flowers: a strong hybridization signal was seen in flower RNA, with a diminished level seen in RNA from immature seed pods. A faint signal was also detected in leaves. To determine whether AGL2 is expressed in an organ-specific manner, in situ hybridization was performed with wild type *Arabidopsis* inflorescence sections. The results showed that AGL2 was expressed mainly in carpels and was concentrated there in the ovules. In addition, AGL2 was expressed at a lower level in the stamens, with expression restricted to the anthers. Thus, the AGL2 gene is selectively expressed in floral organs, with a high level of expression seen in flowers and young seed pods and a much lower level of expression seen in leaves. These results indicate that an AGL2 regulatory element can confer floral organ selective expression upon a heterologous linked gene.

The amino acid sequence of AGL4 is shown in FIGS. 4 and 10a through 10b. The encoded protein, which has a calculated molecular mass of 28.5 kDa, has the characteristic highly conserved MADS domain. RNA dot blot hybridization was used to assess AGL4 expression in immature seed pods, flowers, stems, and leaves. AGL4 was highly expressed in flowers with the expression continuing at a lower level in immature seed pods. No expression was seen in the vegetative stems and leaves. These results indicate that AGL4 is specifically expressed in flowers and that an AGL4 regulatory element can confer floral organ selective expression upon a heterologous linked gene.

*Arabidopsis* AGL9 is a 251 amino acid protein having a calculated molecular mass of 29 kDa. AGL9 has a highly conserved MADS domain, as well as a K domain (see FIG. 5). The protein encoded by *Arabidopsis* AGL9 has a high degree of similarity to the products of the TM5 gene from tomato (*Lycopersicum esculentum*); the petunia gene FBP2, and the DEFH200 gene from *Antirrhinum majus*, indicating that TM5, FBP2 and DEFH200 are AGL9 orthologs (Pnueli et al., *Plant J.* 1:255–266 (1991); Angenent et al., *Plant Cell* 4:983–993 (1992); and Davies et al., *EMBO J.* 15:4330–4343 (1996), each of which is incorporated herein by reference). Throughout the first 160 amino acids, AGL9 shares approximately 89% amino acid identity with the FBP2, TM5 and DEFH200 gene products.

AGL9 RNA accumulates only in flowers, with RNA blot analysis showing no detectable expression in roots, stems or cauline leaves. In situ hybridization analyses demonstrated that AGL9 RNA begins to accumulate after the onset of expression of the floral meristem identity genes but before the expression of the floral organ identity genes. In particular, floral meristem identity genes such as AP1 and CAL are first expressed during stage 1 flower primordia, followed by AGL2 and AGL4, which are first expressed throughout stage 2 flower primordia. AGL9 is subsequently expressed late in stage 2 in a region that does not include the outer perimeter of the flower primordium. Later in flower development, AGL9 RNA accumulates in the petal, stamen, and carpel organs. Thus, AGL9 is specifically expressed only in floral organs, indicating that an AGL9 regulatory element can confer floral organ selective expression upon a heterologous linked gene.

The amino acid sequence of AP1 is shown in FIGS. 8a through 8b (Mandel, 1992 Nature 360:273–277). The encoded protein, which has a calculated molecular mass of 30 kDa, has the characteristic highly conserved MADS domain. The deduced AP1 protein is similar to the snapdragon SQUAMOSA protein, sharing 68% identical amino acid residues (Huijser et al., EMBO J. 33:1239–1249; 1992). RNA blot hybridization was used to assess AP1 expression in roots, stems, leaves, and flowers, where it was shown to be flower specific (Id., FIG. 3). Subsequent RNA tissue in situ hybridizations further defined the AP1 RNA accumulation patter where it was shown to first be expressed in a young flower primordium (a flower meristem) when it first becomes visible on the flanks of the shoot meristem. Additional studies showed that AP1 RNA accumulates in all cells of the young flower, and that in mature flowers, AP1 is expressed in sepals and petals but not in stamens and carpels (Id., FIG. 4). Thus, AP1 is specifically expressed in flowers and that an AP1 regulatory element can confer floral organ selective expression upon a heterologous linked gene. Proof of this concept came from fusing the AP1 regulatory region to the easily assayable "GUS" marker gene and the subsequent generation of transgenic plants that had stably integrated the AP1::GUS transgene into the plant nuclear genome (the POP10 construct and resulting lines)(See FIG. 9).

The AP1 regulatory region includes the 1.7 kb of the AP1 "promoter" (the promoter is defined as the 1700 bp immediately upstream of the AP1 translation initiation codon, ATG), as well as the genomic region containing all AP1 intronic sequences. Both the "full length" AP1 promoter (AP1 promoter plus all genomic regions containing AP1 intronic sequences as shown for the POP10 constrict in FIG. 7) and the 1700 bp AP1 promoter fragment are sufficient to express foreign genes that are operably linked to it within flowers, and thus may be suitable for suppressing flowering. Smaller constructs, such as those that do not contain all of the AP1 intronic sequences, may also be flower specific, and thus it is not necessary to include all of the AP1 genomic sequences to achieve complete flower-specific regulation. However, the use of the "full length" AP1 regulatory region may be used for optimal flower specific expression, since these sequences will drive gene expression only in flowers.

As used herein, the term "floral organ selective regulatory element" refers to a regulatory element such as a 5', 3' or intronic regulatory element that, when operatively linked to a nucleotide sequence, confers selective expression upon the operatively linked nucleotide sequence in a limited number of plant tissues, including one or more floral organs or subparts thereof. Thus, a floral organ selective regulatory element, as defined herein, confers selective expression in the petals, sepals, stamens or carpels of a plant or in some cell types within the petals, sepals, stamens or carpels, with expression low or absent in other tissues of the plant.

A floral organ selective regulatory element can confer specific expression exclusively in cells of one or more floral organ, or can confer selective expression in a limited number of plant cell types including cells of one or more floral organ. For example, an AGL9 regulatory element, which confers specific expression in flowers, without conferring expression in vegetative tissues such as roots, stems or cauline leaves, is a floral organ selective regulatory element as defined herein. A floral organ selective regulatory element also can be, for example, an AGL2 regulatory element, which confers high level expression in flowers, with a minimal level of expression in leaves.

As used herein, the term "AGL2 regulatory element" refers to a regulatory element derived from *Arabidopsis* AGL2 (SEQ ID NO:5) or an ortholog of *Arabidopsis* AGL2. An AGL2 ortholog is a MADS box gene product expressed, at least in part, in one or more floral organs of a plant and having homology to the amino acid sequence of *Arabidopsis* AGL2 (SEQ ID NO:5). An AGL2 ortholog can be, for example, a pine or rice ortholog such as PrMADS1 or OsMADS5 (Mouradov et al., *Plant Physiol.* 117:55–62 (1998); Kang and An, *Mol. Cells* 7:45–51 (1997), each of which is incorporated herein by reference) or can be another ortholog such as a Eucalyptus or spruce ortholog. An AGL2 ortholog generally has at least about 80% amino acid identity with amino acids 1 to 160 of *Arabidopsis* AGL2 (SEQ ID NO:5) and can have, for example, at least about 85%, 90%, or 95% amino acid identity with amino acids 1 to 160 of *Arabidopsis* AGL2 (SEQ ID NO:5).

As used herein, the term "AGL4 regulatory element" refers to a regulatory element derived from *Arabidopsis* AGL4 (SEQ ID NO:7) or an ortholog of *Arabidopsis* AGL4. An AGL4 ortholog is a MADS box gene product expressed, at least in part, in one or more floral organs of a plant and having homology to the amino acid sequence of *Arabidopsis* AGL4 (SEQ ID NO:7). An AGL4 ortholog can be, for example, a Eucalyptus, pine or spruce ortholog. An AGL4 ortholog generally has at least about 80% amino acid identity with amino acids 1 to 160 of *Arabidopsis* AGL4 (SEQ ID NO:7) and can have, for example, at least about 85%, 90%, or 95% amino acid identity with amino acids 1 to 160 of *Arabidopsis* AGL4 (SEQ ID NO:7).

As used herein, the term "AGL9 regulatory element" refers to a regulatory element derived from *Arabidopsis* AGL9 (SEQ ID NO:9) or an ortholog of *Arabidopsis* AGL9. An AGL9 ortholog is a MADS box gene product expressed, at least in part, in one or more floral organs of a plant and having homology to the amino acid sequence of *Arabidopsis* AGL9 (SEQ ID NO:9). An AGL9 ortholog can be, for example, a tomato, petunia or *A. majus* ortholog such as TM5, FBP2 or DEFH200 (Pnueli et al., *The Plant Cell* 6:163–173 (1994); Angenent et al., *Plant Cell* 4:983–993 (1992); and Davies et al., *EMBO J.* 15:4330–4343 (1996)) or can be, for example, a Eucalyptus, pine or spruce ortholog. An AGL9 ortholog generally has at least about 80% amino acid identity with amino acids 1 to 160 of *Arabidopsis* AGL9 (SEQ ID NO:9) and can have, for example, at least about 85%, 90%, or 95% amino acid identity with amino acids 1 to 160 of *Arabidopsis* AGL9 (SEQ ID NO:9).

As used herein the term "AP1 regulatory element" refers to a regulatory element derived from *Arabidopsis* AP1 (SEQ ID NO:12) or an ortholog of *Arabidopsis* AP1. An AP1 ortholog is a MADS box gene product expressed, at least in part, in one or more floral organs of a plant and having homology to the amino acid sequence of *Arabidopsis* AP1 (SEQ ID NO:12). An AP1 ortholog can be, for example, a Snapdragon ortholog, such as SQUAMOSA. Also, an AP1 ortholog could be, for example, a Eucalyptus, pine or spruce ortholog. An AP1 ortholog generally has at least about 75% amino acid identity with amino acids, 1 to 160 of *Arabidopsis* AP1 (SEQ ID NO:12) and can have, for example, at least about 85%, 90%, or 95% amino acid identity with amino acids 1 to 160 of *Arabidopsis* AP1 (SEQ ID NO:12).

Preferably, an AGL2, AGL4 or AGL9 or AP1 floral organ selective regulatory element is orthologous to the transgenic plant species into which it is introduced. An AGL2 promoter (SEQ ID NO:1) or active fragment thereof, for example, can be introduced into an *Arabidopsis* plant to produce a transgenic *Arabidopsis* variety characterized by suppressed flowering. Similarly, a Eucalyptus AGL2, AGL4 or AGL9 or AP1 floral organ selective regulatory element can be introduced into a Eucalyptus plant to produce a transgenic Eucalyptus variety characterized by suppressed flowering.

An AGL2, AGL4 or AGL9 or AP1 floral organ selective regulatory element also can be introduced into a heterologous plant to produce a transgenic plant of the invention characterized by suppressed flowering. AGAMOUS-like gene products have been widely conserved throughout the plant kingdom; for example, AGAMOUS has been conserved in tomato (TAGI) and maize (ZAG1), indicating that orthologs of AGAMOUS-like genes are present in most, if not all, angiosperms (Pnueli et al., *The Plant Cell* 6:163–173 (1994); Schmidt et al., *The Plant Cell* 5:729–737 (1993)). Furthermore, it has been shown that MADS-box genes exist in gymnosperms and angiosperms as well as in ferns, the common ancestors of contemporary seed plants (Tandre et al., *Plant Mol. Biol.* 27:69–78 (1995); Liu and Podila, *Plant Phys.* 113:665 (1997); Münster et al., *Proc. Natl. Acad. Sci., USA* 94:2145–2420 (1997); and Mouradov et al., *Plant Physiol.* 117:55–62 (1998)). AGL2, AGL4 and AGL9 floral organ selective regulatory elements also can be conserved and can function across species boundaries to confer floral organ selective expression in heterologous plant species. Thus, an *Arabidopsis* AGL2, AGL4 or AGL9 or AP1 floral organ selective regulatory element, such as the *Arabidopsis* AGL2, AGL4 or AGL9 or AP1 promoter SEQ ID NO:1, SEQ ID NO:2 or SEQ ID NO:3 or (SEQ ID NO:12), or an active fragment thereof, can confer floral organ selective expression upon an operatively linked nucleotide sequence encoding a cytotoxic gene product in a heterologous plant such as Eucalyptus, whereby the cytotoxic gene product is selectively expressed in floral tissue and flowering is suppressed.

A transgenic plant of the invention that is characterized by suppressed flowering can be one of a variety of plant species. As used herein, the term "plant" means a higher plant that generally is a vascular plant or seed plant such as an angiosperm or gymnosperm. An angiosperm is a seed-bearing plant whose seeds are borne in a mature ovary (fruit) and are divided into two broad classes based on the number of cotyledons or seed leaves that generally store or absorb food. A gymnosperm is a seed-bearing plant with seeds not enclosed in an ovary. In view of the above, the skilled person understands that the invention can be practiced, for example, with a monocotyledonous or dicotyledonous angiosperm or gymnosperm as desired.

In one embodiment, the invention provides a transgenic woody plant that is characterized by suppressed flowering. A transgenic plant of the invention can be, for example, a perennial woody plant such as a tree or shrub. For example, dicot trees such as alder, ash, basswood, beech, birch, cherry, cottonwood, elm, hickory, locust, maple, red and white oak, persimmon, sycamore, walnut, and poplar can be modified as disclosed herein to produce transgenic varieties in which flowering is suppressed. In addition, conifer woods, for example, cedar; Douglas fir; hemlock; loblolly, ponderosa, slash, sugar and western white pines; redwood; and spruce trees can be modified to produce transgenic varieties in which flowering is suppressed. The skilled person understands that the invention can be practiced with these or other shrubs or trees, especially trees useful for producing lumber, pulp or paper (Whetten and Sederoff, *Forest Ecology and Management* 43:301–316 (1991), which is incorporated herein by reference).

The present invention further provides tissues derived from a transgenic plant of the invention. Such tissues are derived from a transgenic plant that is characterized by suppressed flowering and that contains a nucleic acid molecule including a floral organ selective regulatory element operatively linked to a nucleotide sequence encoding a cytotoxic gene product.

As used herein, the term "tissue" means an aggregate of plant cells and intercellular material organized into a structural and functional unit. A particularly useful tissue of the invention is a tissue that can be vegetatively or non-vegetatively propagated such that the transgenic plant from which the tissue was derived is reproduced. A tissue of the invention can be, for example, a leaf, root, stem or part thereof.

The present invention also provides an isolated nucleic acid molecule including an AGL2, AGL4 or AGL9 or AP1 regulatory element, which confers selective expression upon an operatively linked nucleotide sequence in one or more floral organs of a plant. The isolated nucleic acid molecule can further include, if desired, an operatively linked nucleotide sequence encoding a cytotoxic gene product. The encoded cytotoxic gene product can be, for example, diphtheria toxin A chain, RNase T1, Barnase RNase, ricin toxin A chain, or the herpes simplex virus thymidine kinase gene product.

The *Arabidopsis* AGL2 promoter (SEQ ID NO:1) is shown in FIG. 1. An AGL2 regulatory element, such as a 5' regulatory element or intronic regulatory element, can confer selective expression in one or more floral organs such as carpels and stamens and, thus, is a floral organ selective regulatory element as defined herein. An isolated AGL2 floral organ selective regulatory element can have, for example, at least fifteen contiguous nucleotides of the *Arabidopsis* AGL2 sequence SEQ ID NO:1. Such an isolated AGL2 floral organ selective regulatory element can have, for example, at least 16, 18, 20, 25, 30, 40, 50, 100 or 500 contiguous nucleotides of SEQ ID NO:1 and is characterized, in part, by the ability to confer floral organ selective expression upon an operatively linked nucleotide sequence (see Example I).

The *Arabidopsis* AGL4 promoter (SEQ ID NO:2) is shown in FIG. 2. An AGL4 regulatory element confers selective expression in one or more floral organs without conferring expression in vegetative tissues and, thus, is a floral organ selective regulatory element as defined herein. An isolated AGL4 floral organ selective regulatory element can have, for example, at least fifteen contiguous nucleotides of the *Arabidopsis* AGL4 sequence SEQ ID NO:2. Such an isolated AGL4 floral organ selective regulatory element can have, for example, at least 16, 18, 20, 25, 30, 40, 50, 100 or 500 contiguous nucleotides of SEQ ID NO:2 and is characterized, in part, by the ability to confer floral organ selective expression upon an operatively linked nucleotide sequence (see Example II).

The *Arabidopsis* AGL9 promoter (SEQ ID NO:3) is shown in FIG. 3. An AGL9 regulatory element, such as a 5' regulatory element or intronic regulatory element, can confer selective expression in one or more floral organs, specifically in petals, stamens and carpels, and, thus, is a floral organ selective regulatory element as defined herein. An isolated AGL9 floral organ selective regulatory element can have, for example, at least fifteen contiguous nucleotides of the *Arabidopsis* AGL9 sequence SEQ ID NO:3. Such an isolated AGL9 floral organ selective regulatory element can have, for example, at least 16, 18, 20, 25, 30, 40, 50, 100 or 500 contiguous nucleotides of SEQ ID NO:3 and is characterized, in part, by the ability to confer floral organ selective expression upon an operatively linked nucleotide sequence (see Example III).

The *Arabidopsis* AP1 promoter (SEQ ID NO:12) is shown in FIG. 6. An AP1 regulatory element, such as a 5' regulatory element or intronic regulatory element, can confer selective expression in one or more floral organs, specifically in petals, stamens and carpels, and, thus, is a floral organ selective regulatory element as defined herein. An isolated AP1 floral organ selective regulatory element can have, for example, at least fifteen contiguous nucleotides of the *Arabidopsis* AP1 sequence (SEQ ID NO:12). Such an isolated AP1 floral organ selective regulatory element can have, for example, at least 16, 18, 20, 25, 30, 40, 50, 100 or 500 contiguous nucleotides of (SEQ ID NO:12) and is characterized, in part, by the ability to confer floral organ selective expression upon an operatively linked nucleotide sequence (see Example IV).

As used herein, the term "substantially the nucleotide sequence," when used in reference to an AGL2, AGL4 or AGL9 or AP1 regulatory element, means a nucleotide sequence having an identical sequence, or a nucleotide sequence having a similar, non-identical sequence that is considered to be a functionally equivalent sequence by those skilled in the art. For example, a floral organ selective regulatory element that is an AGL2 regulatory element can have, for example, a nucleotide sequence identical to the sequence of the *Arabidopsis* AGL2 promoter (SEQ ID NO:1) shown in FIG. 1, or a similar, non-identical sequence that is functionally equivalent. A floral organ selective regulatory element can have, for example, one or more modifications such as nucleotide additions, deletions or substitutions relative to the AGL2 promoter sequence shown in FIG. 1, provided that the modified nucleotide sequence retains substantially the ability to confer selective expression in one or more floral organs upon an operatively linked nucleotide sequence, such as a nucleotide sequence encoding a cytotoxic gene product.

It is understood that limited modifications can be made without destroying the biological function of an AGL2, AGL4 or AGL9 or AP1 regulatory element and that such limited modifications can result in floral organ selective regulatory elements that have substantially equivalent or enhanced function as compared to a wild type AGL2, AGL4 or AGL9 or AP1 regulatory element. These modifications can be deliberate, as through site-directed mutagenesis, or can be accidental such as through mutation in hosts harboring the regulatory element. All such modified nucleotide sequences are included in the definition of a floral organ selective regulatory element as long as the ability to confer selective expression in one or more floral organs is substantially retained.

A floral organ selective regulatory element can be derived from a gene that is an ortholog of *Arabidopsis* AGL2, AGL4 or AGL9 or AP1 and that is selectively expressed in one or more floral organs of the orthologous plant. An AGL2, A GL4 or AGL9 or AP1 floral organ selective regulatory element can be derived, for example, from an AGL2, AGL4 or A GL9 or AP1 ortholog such as a Eucalyptus, pine or spruce ortholog.

Floral organ selective regulatory elements also can be derived from a variety of other genes that are selectively expressed in one or more floral organs of a plant and can be identified and isolated using routine methodology. Differential screening strategies using, for example, RNA prepared from a floral organ and RNA prepared from non-floral material such as leaf or root tissue can be used to isolate cDNAs selectively expressed in cells of one or more floral organs; subsequently, the corresponding genes are isolated using the cDNA sequence as a probe.

Enhancer trap or gene trap strategies also can be used to identify and isolate a floral organ selective regulatory element (Sundaresan, et al., *Genes Dev.* 9, 1797–1810 (1995); Koncz et al., *Proc. Natl. Acad. Sci. USA* 86:8467–8471 (1989); Kertbundit et al., *Proc. Natl. Acad. Sci USA* 88:5212–5216 (1991); Topping et al., *Development* 112: 1009–1019 (1991), each of which is incorporated herein by reference). Enhancer trap elements include a reporter gene such as GUS with a weak or minimal promoter, while gene trap elements lack a promoter sequence, relying on transcription from a flanking chromosomal gene for reporter gene expression. Transposable elements included in the constructs mediate fusions to endogenous loci; constructs selectively expressed in one or more floral organs are identified by their pattern of expression. With the inserted element as a tag, the flanking floral organ selective regulatory element is cloned using, for example, inverse polymerase chain reaction methodology (see, for example, Aarts et al., Nature 363:715–717 (1993); see, also, Ochman et al., "Amplification of Flanking Sequences by Inverse PCR," in Innis et al. (Ed.), PCR Protocols, San Diego: Academic Press, Inc. (1990)). The Ac/Ds transposition system of Sundaresan, et al., Genes Dev. 9, 1797–1810 (1995), can be particularly useful in identifying and isolating a floral organ selective regulatory element useful in the invention.

Floral organ selective regulatory elements also can be isolated by inserting a library of random genomic DNA fragments in front of a promoterless reporter gene and screening transgenic plants transformed with the library for floral organ selective reporter gene expression. The promoterless vector pROA97, which contains the npt gene and the GUS gene each under the control of the minimal 35S promoter, can be useful for such screening. The genomic library can be, for example, Sau3A fragments of Arabidopsis thaliana genomic DNA or genomic DNA from, for example, Eucalyptus, pine or spruce (Ott et al., Mol. Gen. Genet 223:169–179 (1990); Claes et al., The Plant Journal 1:15–26 (1991), each of which is incorporated herein by reference).

An active fragment of an AGL2, AGL4 or AGL9 or AP1 promoter, which contains a floral organ selective regulatory element, can be identified by routine techniques, for example, using a reporter gene and in situ expression analysis. The GUS and firefly luciferase reporter genes are particularly useful for in situ localization of plant gene expression (Jefferson et al., EMBO J. 6:3901 (1987); Ow et al., Science 334:856 (1986), each of which is incorporated herein by reference), and promoterless vectors containing the GUS expression cassette are commercially available, for example, from Clontech (Palo Alto, Calif.). To identify an active fragment containing a floral organ selective regulatory element such as an AGL2, AGL4 or AGL9 or AP1 regulatory element, one or more nucleotide portions of an AGL2, AGL4 or AGL9 or AP1 gene can be generated using enzymatic or PCR-based methodology (Glick and Thompson (eds.), Methods in Plant Molecular Biology and Biotechnology, Boca Raton, Fla.: CRC Press (1993); Innis et al. (Ed.), PCR Protocols, San Diego: Academic Press, Inc. (1990)); the resulting segments are fused to a reporter gene such as GUS and analyzed as described above.

The present invention also provides a kit for producing a transgenic plant characterized by suppressed flowering. A kit of the invention comprises packaging containing a plant expression vector having a floral organ selective regulatory element operatively linked to a nucleotide sequence encoding a cytotoxic gene product. The plant expression vector can include, if desired, a nucleotide sequence encoding a selectable marker or reporter gene, along with instructions to employ the vector in accord with the present method.

The term "plant expression vector," as used herein, is a self-replicating nucleic acid molecule that provides a means to transfer an exogenous nucleic acid molecule into a plant host cell and to express the molecule therein. Plant expression vectors encompass vectors suitable for Agrobacterium-mediated transformation, including binary and cointegrating vectors, as well as vectors for physical transformation.

Plant expression vectors can be used for transient expression of the exogenous nucleic acid molecule, or can integrate and stably express the exogenous sequence. One skilled in the art understands that a plant expression vector can contain all the functions needed for transfer and expression of an exogenous nucleic acid molecule; alternatively, one or more functions can be supplied in trans as in a binary vector system for Agrobacterium-mediated transformation.

In addition to a floral organ selective regulatory element and a nucleotide sequence encoding a cytotoxic gene product, a plant expression vector of the invention can contain, if desired, additional elements. A binary vector for Agrobacterium-mediated transformation contains one or both T-DNA border repeats and can also contain, for example, one or more of the following: a broad host range replicon, an ori T for efficient transfer from E. coli to Agrobacterium, a bacterial selectable marker such as ampicillin and a polylinker containing multiple cloning sites.

A plant expression vector for physical transformation can have, if desired, a plant selectable marker or a reporter gene or both, in addition to a floral organ selective regulatory element in vectors such as pBR322, pUC, pGEM and M13, which are commercially available, for example, from Pharmacia (Piscataway, N.J.) or Promega (Madison, Wis.).

A selectable marker gene or a reporter gene can facilitate the identification and selection of transformed plants, or plant cells. Both selectable marker and reporter genes may be flanked with appropriate regulatory sequences to enable expression in plants. Useful selectable markers are well known in the art and include, for example, antibiotic and herbicide resistance genes. Specific examples of such genes are disclosed in Weising, K., et al., Ann. Rev. Genet., 22, 421–478 (1988). Selectable marker genes includes the hygromycin B phosphotransferase coding sequence, which confers resistance to hygromycin B; the aminoglycoside phosphotransferase gene of transposon Tn5 (AphII), which encodes resistance to the antibiotics kanamycin, neomycin and G418; and genes which code for resistance or tolerance to glyphosate, 1,2-dicholoropropionic acid methotrexate, imidazolinones, sulfonylureas, bromoxynil, phophononthricin and the like.

Reporter genes which encode for easily assayable marker proteins are well known in the art. IN general, a reporter gene is a gene which ins not present in or expressed by the recipient organism or tissue and which encodes a protein whose expression is manifested by some easily detectable property, e.g., phenotypic change or enzymatic activity. Examples of such gene are provided in Weising, et al., Ann. Rev. Genet., 22, 421–478 (1988).

In plant expression vectors for physical trans formation of a plant, the T-DNA borders or the ori T region can optionally be included but provide no advantage.

Also provided by the present invention is a method of producing a transgenic plant characterized by suppressed flowering. The method includes the step of introducing into a plant an exogenous nucleic acid molecule containing a floral organ selective regulatory element operatively linked to a nucleotide sequence encoding a cytotoxic gene product, where flowering is suppressed due to selective expression of the exogenous nucleic acid molecule and where the floral organ selective regulatory element is an AGL2 regulatory element, an AGL4 regulatory element or an AGL9 regulatory element or an AP1 regulatory element.

Methods for producing the desired recombinant nucleic acid molecule under control of an AGL2, AGL4 or AGL9 or AP1 floral organ selective regulatory element and for producing a transgenic plant of the invention are well known in the art (see, generally, Sambrook et al. (eds.) *Molecular Cloning: A Laboratory Manual* (Second Edition, Plainview, N.Y.: Cold Spring Harbor Laboratory Press (1989); Glick and Thompson, supra, 1993).

An exogenous nucleic acid molecule can be introduced into a plant using a variety of transformation methodologies including *Agrobacterium*-mediated transformation and direct gene transfer methods such as electoporation and microprojectile-mediated transformation (see, generally, Wang et al. (eds), *Transformation of Plants and Soil Microorganisms*, Cambridge, UK: University Press (1995), which is incorporated herein by reference).

Transformation methods based upon the soil bacterium *Agrobacterium tumefaciens* are particularly useful for introducing an exogenous nucleic acid molecule into a plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or, preferably, binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art (Glick and Thompson, supra, 1993). Wounded cells within dicot plant tissue that have been infected by *Agrobacterium* can develop organs de novo when cultured under the appropriate conditions; the resulting transgenic shoots eventually give rise to transgenic plants that ectopically express a nucleic acid molecule containing a floral organ selective regulatory element operatively linked to a nucleotide sequence encoding a cytotoxic gene product. *Agrobacterium* also can be used for transformation of whole plants as described in Bechtold et al., *C.R. Acad. Sci. Paris, Life Sci.* 316:1194–1199 (1993), which is incorporated herein by reference).

Microprojectile-mediated transformation also can be used to produce a transgenic plant containing a nucleic acid molecule including a floral organ selective regulatory element operatively linked to a nucleotide sequence encoding a cytotoxic gene product. This method, as described by Lundquist et al., U.S. Pat. No. 5,554,798, which is incorporated herein by reference), relies on microprojectiles such as gold or tungsten that are coated with the desired nucleic acid molecule by precipitation with calcium chloride, spermidine or PEG. The microprojectile particles are accelerated at high speed into an angiosperm tissue using a device such as the BIOLISTIC PD-1000 (Biorad; Hercules Calif.).

Microprojectile-mediated delivery or "particle bombardment" is especially useful to transform plants that are difficult to transform or regenerate using other methods. Microprojectile-mediated transformation has been used, for example, to generate a variety of transgenic plant species, including cotton, tobacco, corn, hybrid poplar and papaya (see Glick and Thompson, supra, 1993) as well as cereal crops such as wheat, oat, barley, sorghum and rice (Duan et al., *Nature Biotech.* 14:494–498 (1996); Shimamoto, *Curr. Opin. Biotech.* 5:158–162 (1994), each of which is incorporated herein by reference). In view of the above, the skilled artisan will recognize that *Agrobacterium*-mediated or microprojectile-mediated transformation, as disclosed herein, or other methods known in the art can be used to produce a transgenic plant of the invention characterized by suppressed flowering.

Following transformation via any method, it is necessary to identify and select those plants or cells which both contain the heterologous DNA and still retain sufficient regenerative capacity. There are two general approaches which have been found useful for accomplishing this. First, the transformed calli or plants regenerated therefrom can be screened for the presence of the heterologous DNA by various standard methods which could include assays for the expression of reporter genes or assessment of phenotypic effects of the heterologous DNA, if any. Alternatively, and preferably, when a selectable marker gene has been transmitted along with or as part of the heterologous DNA, those cells of the callus or plant which have been transformed can be identified by the use of a selective agent to detect expression of the selectable marker gene.

Selection of the putative transformants is a critical part of the successful transformation process since selection conditions must be chosen so as to allow growth and accumulation of the transformed cells or plants while simultaneously inhibiting the growth of the non-transformed cells or plants.

Selection procedures involve exposure to a toxic agent and may employ sequential changes in the concentration of the agent and multiple rounds of selection. The particular concentrations and cycle lengths are likely to need to be varied for each particular agent. A currently preferred selection procedure entails using an initial selection round at a relatively low toxic agent concentration and then later round(s) at higher concentration(s). This allows the selective agent to exert its toxic effect slowly over a longer period of time. Preferably, the concentration of the agent is initially such that about a 5–40% level of growth inhibition will occur, as determined from a growth inhibition curve. The effect may be to allow the transformed cells or plants to preferentially grow and divide while inhibiting untransformed cells or plants, but not to the extent that growth of the transformed cells or plants is prevented. Once the few individual transformed cells or plants have grown sufficiently, the tissue may be shifted to media containing a higher concentration of the toxic agent to kill essentially all untransformed cells. The shift to the higher concentration also reduces the possibility of non-transformed cells or plants habituating to the agent. The higher level is preferably in the range of about 30 to 100% growth inhibition. The length of the first selection cycle may be from about 1 to 4 weeks, preferably about 2 weeks. Later selection cycles may be from about 1 to about 12 weeks, preferably about 2 to about 10 weeks. Putative transformants can generally be identified as viable plants. In the case of transformation of cells, putative transformants can generally be identified as proliferating sectors of tissue among a background of non-proliferating cells.

Once a putative transformant is identified, transformation can be confirmed by phenotypic and/or genotypic analysis. If a selection agent is used, an example of phenotypic analysis is to visually inspect the plants. The plants which appear to be green, growing, and healthy are compared to a control on various levels of the selective agent. Another example of phenotypic analysis is to measure the increase in fresh weight of the putative transformant as compared to a control on various levels of the selective agent. Other analyses that may be employed will depend on the function of the heterologous DNA. For example, if an enzyme or protein is encoded by the DNA, enzymatic or immunological assays specific for the particular enzyme or protein may be used. Other gene products may be assayed by using a suitable bioassay or chemical assay. Other such techniques are well known in the art and are not repeated here. The presence of the gene can also be confirmed by conventional procedures, i.e., Southern blot or polymerase chain reaction (PCR) or the like.

EXAMPLE I

An AGL2 Regulatory Element Directs Floral Organ Selective Expression

This example shows that a fragment of the *Arabidopsis* AGL2 promoter is sufficient to direct floral organ selective gene expression.

*Agrobacterium tumefaciens* strain C58 was used to transform *Arabidopsis thaliana*, ecotype Columbia. The transformation method of this example was disclosed by Bechtold et al., *C. R. Acad. Sci. Paris,* 316:1194–9 (1993) (incorporated by reference herein).

A BglII fragment of approximately 2.3 kb was isolated from the *Arabidopsis* AGL2 promoter (SEQ ID NO:1) shown in FIG. 1 using the BglII sites indicated at nucleotide 1 and nucleotide 1120. The fragment was subcloned into the BamHI site of pGEM3Z (Promega, Madison, Wis.). The resulting plasmid was restricted with SalI and SmaI and subcloned into the corresponding sites of the GUS expression vector pBI101.2 (CLONTECH, Palo Alto, Calif.) to create pKY18. Analysis of GUS expression in kanamycin resistant *Arabidopsis* lines transformed with pKY18 revealed floral specific GUS expression with no significant expression in tissues other than flowers.

These results indicate that the 2.3 kb *Arabidopsis* AGL2 promoter fragment of SEQ ID NO:1 directs floral organ selective expression of a heterologous linked gene product.

EXAMPLE II

An AGL4 Regulatory Element Directs Floral Organ Selective Expression

This example shows that a fragment of the *Arabidopsis* AGL4 promoter is sufficient to direct floral organ selective gene expression.

*Agrobacterium tumefaciens* strain C58 was used to transform *Arabidopsis thaliana*, ecotype Columbia. The transformation method of this example was disclosed by Bechtold et al., *C. R. Acad. Sci. Paris,* 316:1194–9 (1993) (incorporated by reference herein).

AGL4 promoter fragments were isolated from the promoter sequence shown in FIG. 2 (SEQ ID NO:2). A 560 bp AGL4 fragment of SEQ ID NO:2 was prepared containing the region from nucleotide −862 to nucleotide −303 using the HindIII site indicated at nucleotide −862 and an engineered BamHII site. The 560 bp fragment was subcloned into the HindIII and BamHI sites of pGEM3Z (Promega). A 270 bp AGL4 fragment of SEQ ID NO:2 was prepared similarly using the indicated DraI site at nucleotide −573 and an engineered BamHI site at nucleotide −303 and subcloned into the HincII and BamHI sites of pGEM3Z. The 560 bp and 270 bp fragments were subsequently cloned into the GUS expression vector pBI101.1 (CLONTECH) to produce pSR34 and pSR35, respectively.

Plants were transformed with pSR34 and pSR35. GUS staining was observed in the flowers of pSR34 plants. These results demonstrate that the 560 bp fragment of the *Arabidopsis* A GL4 promoter confers floral organ selective expression upon a linked gene.

EXAMPLE III

An AGL9 Regulatory Element Directs Floral, Organ Selective Expression

This example shows that a fragment of the *Arabidopsis* AGL9 promoter is sufficient to direct floral organ selective gene expression.

*Agrobacterium tumefaciens* strain C58 was used to transform *Arabidopsis thaliana*, ecotype Columbia. The transformation method of this example was disclosed by Bechtold et al., *C. R. Acad. Sci. Paris,* 316:1194–9 (1993) (incorporated by reference herein).

The entire 1755 bp AGL9 promoter fragment shown in FIG. 3 (SEQ ID NO:3) was cloned into the GUS expression vector pBI101.3 (CLONTECH) to produce pSP112. Multiple transgenic lines containing pSP112 were analyzed for GUS expression. The results showed that GUS was expressed only in floral organs, with no expression evident in other tissues such as stem.

These results demonstrate that an AGL9 promoter is a floral organ selective regulatory element that can confer floral organ selective expression upon an operatively linked encoded gene such as GUS.

EXAMPLE IV

Ab AP1 Regulatory Element Directs Floral Organ Selective Expression

This example shows that a fragment of the *Arabidopsis* AP1 promoter is sufficient to direct floral selective gene expression.

*Agrobacterium tumefaciens* strain C58 was used to transform *Arabidopsis thaliana*, ecotype Columbia. The transformation method of this example was disclosed by Bechtold et al., C. R. Acad. Sci. Paris, 316:1194–9 (1993) (incorporated by reference herein).

Figure 7:
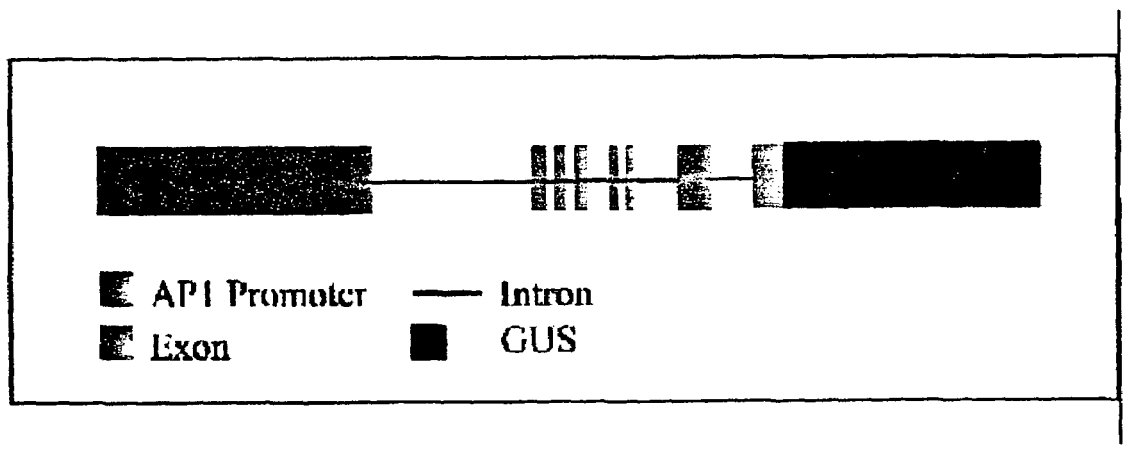
FIG. 7 shows a diagram of reporter construct POP10. The construct has 1.7 kb AP1 promoter plus the entire coding region of AP1 in front of promoterless GUS gene in pBI101.2 plasmid. The construct has 1.7 kb AP1 promoter plus the entire coding region of AP1 in front of promoterless GUS gene in pBI101.2 plasmid. The construct was first made by PCR amplification from intron 3 to the end of AP1 gene in exon 8 (right before stop codon) using KY65 plasmid containing AP1 genomic region as template. The HindIII site was added to the forward primer AP1HIN [5'-CAAGCTTGTACACATTTACACTCATCACAT-3' (SEQ ID NO:17)] and BamHI site was added to reverse primer AP1BAM, [5'-CGGATCCTGCGCGAAGCAGC-CAAGGTTG-3' (SEQ ID NO:18)] to aid cloning (sequence in italic are restriction sites of HindIII and BamHI). The 1.7 kb amplified fragment was cloned into plasmid pBI101.2 using HindIII and BamHI sites giving construct POP9. The 3.6 kb HindIII XbaI fragment was isolated from KY65 plasmid and cloned into POP9 construct giving POP10 construct.

The entire 1.7 kb AP1 promoter shown in FIG. 6 (SEQ ID NO:12) plus the entire coding region of AP1 including introns was cloned into the GUS expression vector pBI101.2 to produce the POP10 construct (FIG. 7). The construct was first made by PCR amplification from intron 3 to the end of AP1 gene in exon 8 (right before stop codon) using KY65 plasmid containing AP1 genomic region as template. The HindIII site was added to the forward primer AP1HIN and BamHI site was added to reverse primer AP1BAM to aid cloning. The 1.7 kb amplified fragment was cloned into plasmid pBI101.2 using HindIII and BamHI sites giving construct POP9. The 3.6 kb HindIII/XbaI fragment was isolated from KY65 plasmid and cloned into POP9 contruct giving POP10 contruct.

Multiple transgenic lines containing the POP 10 construct were analyzed for GUS expression. The results showed the GUS was expressed specifically in the young flower primordium (See FIG. 9) as soon as it arises on the flanks of the shoot meristem. No GUS staining was seen in the shoot meristem, the stem, leaves, roots, or any part of the plant other than in flowers.

All journal articles, references, and patent citations provided above, in parentheses or otherwise, whether previously stated or not, are incorporated herein by reference.

It should be understood that various modifications can be made without departing from the spirit of the invention. Accordingly, the invention is limited only by the following claims.

REFERENCES CITED

The references listed below are incorporated by reference herein.

Aarts et al., *Nature* 363:715–717 (1993).
Angenent et al., *Plant Cell* 4:983–993 (1992).
Bechtold et al., *C.R. Acad. Sci. Paris, Life Sci.* 316:1194–1199 (1993).
Bowman et al., *Devel.* 112:1–20 (1991).
Bowman et al., *The Plant Cell* 1:37–52 (1989).
Claes et al., *The Plant Journal* 1:15–26 (1991).
Collier, *Bacteriol. Rev.* 39:54–85 (1975).
Davies et al., *EMBO J.* 15:4330–4343 (1996).
Duan et al., *Nature Biotech.* 14:494–498 (1996).
Glick and Thompson (eds.), *Methods in Plant Molecular Biology and Biotechnology*, Boca Raton, Fla.: CRC Press (1993).
Greenfield et al., *Proc. Natl. Acad. Sci., USA* 80:6853–6857 (1983).
Higuchi, "Recombinant PCR" in Innis et al. (Ed.), *PCR Protocols*, San Diego: Academic Press, Inc. (1990).
Huang et al., *The Plant Cell* 8:81–94 (1996).
Huijser et al., *EMBO J.* 33:1239–1249; 1992.
Innis et al. (Ed.), *PCR Protocols*, San Diego: Academic Press, Inc. (1990).
Jefferson et al., *EMBO J.* 6:3901 (1987).
Kang and An, *Mol. Cells* 7:45–51 (1997).
Kertbundit et al., *Proc. Natl. Acad. Sci. USA* 88:5212–5216 (1991).
Koncz et al., *Proc. Natl. Acad. Sci. USA* 86:8467–8471 (1989).
Liu and Podila, *Plant Phys.* 113:665 (1997).
Ma et al., *Genes Devel.* 5:484–495 (1991).
Mandel and Yanofsky, *The Plant Cell* 7:1763–1771 (1995).
Mandel, *Nature* 360:273–277 (1992).
Moffat et al., *Development* 114:681–687 (1992).
Mouradov et al., *Plant Physiol.* 117:55–62 (1998).
Münster et al., *Proc. Natl. Acad, Sci., USA* 94:2145–2420 (1997).
Norman et al., *Cell* 55:989–1003 (1988).
Ochman et al., "Amplification of Flanking Sequences by Inverse PCR," in Innis et al., (Ed.), *PCR Protocols*, San Diego: Academic Press, Inc. (1990).
Olsnes and Pihl, *Molecular Action of Toxins and Viruses*, pages 51–105, Amsterdam: Elsevier Biomedical Press (1982).
Ott et al., *Mol. Gen. Genet.* 223:169–179 (1990).
Ow et al., *Science* 334:856 (1986).
Palmiter et al., *Cell* 50:435–443 (1987).
Passmore et al., *J. Mol. Biol.* 204:593–606 (1988).
Pnueli et al., *Plant J.* 1:255–266 (1991).
Pnueli et al., *The Plant Cell* 6:163–173 (1994).
Purugganan et al., *Genetics* 140:345–356 (1995).
Riechmann and Meyerowitz, *Biol. Chem.* 378:1079–1101 (1997).
Sambrook et al. (eds.) *Molecular Cloning: A Laboratory Manual* (Second Edition, Plainview, N.Y.: Cold Spring Harbor Laboratory Press (1989).
Schmidt et al., *The Plant Cell* 5:729–737 (1993).
Shimamoto, *Curr. Opin. Biotech.* 5:158–162 (1994).
Sundaresan, et al., *Genes Dev.* 9, 1797–1810 (1995).
Tandre et al., *Plant Mol. Biol.* 27:69–78 (1995).
Topping et al., *Development* 112:1009–1019 (1991).
Thorsness and Nasrallah, *Methods in Cell Biology* 50:439–448 (1995).
Wang et al. (eds), *Transformation of Plants and Soil Microorganisms*, Cambridge, UK: University Press (1995).
Weigel and Meyerowitz, *Cell* 78:203–209 (1994)
Weising, K., et al., *Ann. Rev. Genet.*, 22, 421–478 (1998).
Whetten and Sederoff, *Forest Ecology and Management* 43:301–316 (1991).
Yarnaizumi et al., *Cell* 15:245–250 (1978).
Yanofsky, *Annual Rev. Plant Physiol. Mol. Biol.* 46:167–188 (1995).
Yanofsky et al., *Nature* 346:35–39 (1990).

SEQUENCE LISTING

```
<160> NUMBER OF SEQ ID NOS: 18

<210> SEQ ID NO 1
<211> LENGTH: 4512
<212> TYPE: DNA
<213> ORGANISM: Arabidopsis thaliana
<220> FEATURE:
<223> OTHER INFORMATION: AGL2 promoter
<220> FEATURE:
<221> NAME/KEY: modified_base
<222> LOCATION: (254)..(260)
<223> OTHER INFORMATION: n = g, a, c or t

<400> SEQUENCE: 1
agatctctat gaaaaatggc aaaatcaaca ataatccctt ggctatatgg tggtatttct      60
gttaaaagtg acttatgggt agattttta gcttcataga ttctttgtcg aaaaaaaatt     120
actttgtaca ttttagtgga gttatttaaa tttcccaatt gaacaaaacc atatattgat    180
```

```
gaaattcgca aatgcaatcc aaaaataaat atgttccact cttttggtta gcttttaact      240
aaacatgcgt tttnnnnnnn ttccagctag tacgagtctc tatatataaa ctttcttaat      300
atcgctaaca atttacttca agtttgtaat gtgataagtg aaagaccgta tatacataca      360
catgttaatc aactgataac ctttgtgcct cgtgtgtcta gttactagtc aaccatcaaa      420
cgtgcatgat gctgtttttc ttagagtact attgttgtgt tatatataac taaacataaa      480
caatttgcta ttatgatata aacatagaat tttcaagcaa tgatatgttt agatgttttg      540
tataaatatt ccataaatag tagacaccca tatatacaca aacatgaatt ctacctgagg      600
agaaacacat agatgttcaa attaaataat aaccctataa tgaaaactct aaagtaagta      660
atacgaaata aaaatttatc ctttaaataa catataacat atatatcaac tttaattggt      720
aattgtatca caagagccaa ttatttggtg actgtatcac acgtgcttaa agagagcgtg      780
ggaatgaaag taaagaagaa taaagaagca gagagatggg ctagaaatga gaaaacacac      840
caaaccctaa cctcaccctc acacatttct tatcttttgc tctcaataga ttccattgat      900
tcaaaacaaa atttttcatta agatttcaca acctccacac acttccaaac acaattaaag      960
agaggaaaaa gaatcaataa ccctataaat aaaaaatcag acaaacagaa gtttcctctt     1020
cttcttcctt aagctagtac cttttgttct tgaaattagg gttaatttct tttttccaaa     1080
taccatcaat tctccagacc ataaaaactc aaaaagatca gatctttcct ctgaaaaaga     1140
gatacccaac ttatgttttt gtgtgtctgt atatagataa acattacata cccatatttg     1200
tgtatagaca taaaaagtgg aaattaaggt aacaaaaaga aatgggaaga ggaagagtag     1260
agctgaagag gatagagaac aaaatcaaca gacaagtaac gtttgcaaag cgtaggaacg     1320
gtttgttgaa gaaagcttat gaattgtctg ttctctgtga tgctgaagtt gctctcatca     1380
tcttctccaa ccgtggaaag ctctatgagt tttgcagctc ctcaaagtaa acaactctct     1440
cactctttat cagtttcttg attgagtttt tgctagatct gagcttagat ctttgtctca     1500
aggacttgtt atatatagat cacacgatct tgatttctac gaagttgagt taattagatt     1560
tcttgatttc attttctagg gttttttttcc aattcttgaa atttaagatc tggtttttt     1620 gttgtcaatg atttagaact gtgaattttg taatcgaata gattccaaat cctgatatgc     1680
aatctgaaaa gttttatata attaatatat gtctgtgtga ttggaaactt aaaagttgga     1740
atcacagatt tctatgaaaa ttacaagtat ccaacgtaga attgataata tatggttaca     1800
tgcattaacc atttgttagt tcatcatact ttatggtggt taaaacttca aacgcgtgta     1860
tatctatgaa ggcaaagatt gtttgttttt tcttaaaaac aatgtttaat agattttttaa     1920 ttatatgtta aaatagtttt gcttacatgc attcaagaaa atatagcgat taattccttt     1980
tttcaaatca caatttgtga atcaaacgaa aacgtaagat attgcttgca aatgatagga     2040
ttgaactatt gatatttgta aatataaata cgaaacttta cgtttgaaag ttgaaacaat     2100
caaatccaaa tcaactcgta tataatcaga taaataatgg aaacaatctt cattttttgat    2160 ggaagaatac tttaaaactt gaagagcttt ttttttttat ggtgatttat aggtttagat     2220
ctccaaagtc aagtatgatc tttttaataa actcttattc tctcttttg agttattttc      2280 agcatgctca agacacttga tcggtaccag aaatgcagct atggatccat tgaagtcaac     2340
aacaaacctg ccaaagaact tgaggtgttc ttaattcaaa tactatttg agttcctatc      2400 atatcatttc aagaaagatc ttttttttta aagtttgtt ttcgtgaaat atttcagaac      2460
agctacagag aatatctgaa gcttaagggt agatatgaga acccttcaacg tcaacagagg    2520
```

```
tacatatcta tctataccctc catatatttta ctcaattctg tatccatgta gattcatatt      2580
tgtaggtgtg tgtggctttt gttggtgcag aaatcttctt ggggaggatt taggacctttt     2640 gaattcaaag gagttagagc agcttgagcg tcaactggac ggctctctca agcaagttcg      2700
gtccatcaag gtatctttat gcatggaatc aatgattcaa atgagattaa tttgtgttgt      2760
ttaattatac tactatggtg gtatgatgat tgtttgcaga cacagtacat gcttgaccag      2820
ctctcggatc ttcaaaataa agagcaaatg ttgcttgaaa ccaatagagc tttggcaatg      2880
aaggtataat tacagaataa atgcatttgg tgacttgcga tcaatctctt tcacagagtt      2940
taagtttcta aatatgttttt gaaacatctc tagttttctt gtttctgatt atagtctttt    3000
ggtgaaatgt aaatgtttag ctggatgata tgattggtgt gagaagtcat catatgggag      3060
gatgggaagg cggtgaacag aatgttacct acgcgcatca tcaagctcag tctcagggac      3120
tataccagcc tcttgaatgc aatccaactc tgcaaatggg gtaaatctgc cttgaaaaat      3180
catctgcaaa tcagtttgtg tacttaacta ctaagattgt ccttatttaa ggttcttttag     3240 ttgcttggtg taaagaggat catcaatgtg tgtgaacctt ctaagttgat gttttggcga      3300
tgatgatgat gatgcaggta tgataatcca gtatgctctg agcaaatcac tgcgacaaca      3360
caagctcagg cgcagccggg aaacggttac attccaggat ggatgctctg agaatcatgt      3420
actgtgatga agctcaccca caaaagacct tatatatata taaagtatag atacaagact      3480
tggatttgta gacataagtg gctaatataa tggtcctgag gatcttctag acatttgtat      3540
cttttgggaa tccttgctta tattaagaat tcaaatgtgt ggaacttgtt ttaacactga      3600
accatgacac tggtttatta tcatgtaatg agagaaacat ttgggttaca atgtgatctc      3660
tccttgaccc aaatacacaa tataaaccct atgccaaaat acaagcatca catatatata     3720
ttcataaaag gtttaagtaa tcatacaaat gatgtaaaaa gtttcatgcc ttgaacaaaa      3780
cactgcgcca aaggcaaatg gtaagaaaca tgtcagattc ctgtgtgcat ctgttttgct      3840
gctgctgctg ttgttatctc tcaagagggt ttcctcagaa ctccataagc caaacgtgca      3900
gagagacgtt tcctcattcc cccatcgtat acaataccat atattgttaa aaaaaagata      3960
tcacagatca aatcaatttg cacatctctc tgctgccttg tcaatctcct caggtccggt      4020
caaggcagat caagacagga tcaatggcaa caagttacgg tgtttcgttg aactccatca      4080
cctgcaaatg agacgaattc acagcagaga aaaaaatatt ctttagtcaa catgaatgag      4140
aaataattca aatgttctga gtttcaggaa gaatgattag ccatatttgt actagacaag      4200
acaagtaaag attttacgca tgtgcttcta gggttgttgt acatctttca ttctattgat      4260
ctctggatca ctcgtctatt tatgcgtgat ggtgtctgag tctgactctg aaacactagt      4320
aaatgagaag ccgaaaactg gcttggaaga acatgaaaag tgtttacctt tccacaaaca      4380
gggcagtttt cacttctctc catccattca taaatgcaac taaggtggaa atggtgagaa      4440
cactttgtaa caatcttcgg gttctctgat atgtattcta caaaacacac gaaataatct      4500
gatactaagc tt                                                          4512
```

<210> SEQ ID NO 2
<211> LENGTH: 3589
<212> TYPE: DNA
<213> ORGANISM: Arabidopsis thaliana
<220> FEATURE:
<223> OTHER INFORMATION: AGL4 promoter
<220> FEATURE:
<221> NAME/KEY: modified_base
<222> LOCATION: (1532)..(1537)
<223> OTHER INFORMATION: n = a, g, c or t -continued

<400> SEQUENCE: 2

```
tgatagcgct tcgttcatca tgcagaagaa accaatgttt ccccaatctc acgcgcctcc    60
tcctatctac caccacttgg acaaatcccc tttgcagtat tcgttttttt ttccggacat   120
tgtacattca aaagcattcc aagtgtctaa taaacataac taaccactcc aagatgcaaa   180
atctagctac gacgaacaaa ttttaaacta tagagatgaa ctttaaattc gggcattaat   240
tagtggaact tgagctattg atgatcgagt tttctgactt tttgaagctt aagcttaatt   300
gagttttata tacactatat aggcttgtaa taatatggat caaacaagaa aaatacaaac   360
tacaaattgg gaattgggtt ttaaaacgtt atcgttctat tttaattcag gcacgtacct   420
ttagaatatc aagatccatg tttcaatatt tctgttgaca aataaataaa gatgtctcaa   480
atataagttg ggcaacgtac gtgtagacct aaaagagtcg aaacattggt atctaagtta   540
tatatctaca tggattatat aacaagacaa cgtttgtttt aaaaacttca ttgattttc    600
ttaattagta gcaactagca actaactact catggcaaat aatggcgtct gcgtggcacg   660
cgacttggga gagaaggtgt gagaatgttt ttactttctg tgtaaaagat ggaagagaga   720
gaaagagtaa agaagtagag agagagatat tgtatcacca aaccctaatg atctctcacc   780
ctcacaaatt ttcttatctt tatagctttt atagattcac aaaaacttt cttcagattc     840
acaatctcat cacaacccttt caaaaagaga aagatctaa agaataaaca agagccctaa    900
tatcaaatca caaccaaaaa aaccaaagaa agctaattaa agttttctct ctagctattc    960
ctcttctttt cttgttcttg aaaactaggg tttacttcac caaaaagata agatctttcc    1020
ccagaaaaag caatacccaa gtcatgtttc tgtgtgtctg tatatagata aaacattaca    1080
tacccctaata aggttacaca aatagctata aagagggaa aataagatag ggatttttttg   1140
gggtgaggaa agatgggaag aggaagagta gagctcaaga ggatagagaa caaaatcaac   1200
agacaagtga cgtttgctaa acgtagaaat ggtttcgtga aaaaagctta tgagcttct     1260
gttctctgcg atgctgaagt ctctctcatc gtcttctcca accgtggcaa gctctacgag   1320
ttctgcagca cctccaagta cttctctttc tttatacact tattagatct gtgtgtagat   1380
cttcatttt ttctagtctt gtgatgagtt ttatctttct tgattgcttt ttaacaaaat    1440
acttgatata ttttcagttt cttaatctga ctctaattag gttttgatta ataggaagga   1500
aataaatcca ggtacctttc aaggtgaatt gnnnnnngag atctgatctt aatttaatca   1560
tcatgtcaaa ttcttaggga tttaattgca atctattttt agatttatcg gagctaggaa   1620
agtatcataa tgatatacta ttattatcat gtaatttcat tgtctctaca cggatatata   1680
tgtgattaga acttggtaaa gtaaactaaa gattcacagt cttcaatgaa attgaaaaga   1740
tccaacgtag aataattagt ggttccatgc attaaccagt ctaattaaag ctcatgcaga   1800
catttaagca ccacatgaat ttaatatctt tttaattaag ggatcttctt tttataaatt   1860
ttcttttgtt agcttttaaa attttagttt gttcattaaa atttatagat cctcctctcc   1920
tgatttgtgt tttccgatcc tttccagcat gctcaagaca ctggaaaggt atcagaagtg   1980
tagctatggc tccattgaag tcaacaacaa acctgctaaa cagcttgagg tttaatctcc   2040
aacatctctt cgatcttaat tatttatcct tttttaattt tatctaaaga aaatgtttga   2100
ttttgagaca aaagcccttc aaagtttctt acatagatat tcaattgtct attatcttcg   2160
caattttcag aacagctaca gagagtactt gaagctgaaa ggtagatatg aaaatctgca   2220
acgtcagcag aggtatatac attaatgtgg atgatgatca tttataaaca gcatatatat   2280
```

-continued

| | | | | |
|---|---|---|---|---|
| atatatatat | atatatatat | atatagaaag | tattgatcat | gaaagtgtgt | tgcagcagaa | 2340 |
| atcttcttgg | agaggatctt | ggacctctga | attcaaagga | gctagagcag | cttgagcgtc | 2400 |
| aactagacgg | ctctctgaag | caagttcgct | gcatcaaggt | gatttacttc | tgtacataca | 2460 |
| ctgaaagatt | cacacaaatc | tttctctata | tatagactga | gacacatgca | tgaaatgttt | 2520 |
| ttgatgcgtg | aggttatctg | aaaatgcctc | ttctttttg | cagacacagt | atatgcttga | 2580 |
| ccagctctct | gatcttcaag | gtaaggagca | tatcttgctt | gatgccaaca | gagctttgtc | 2640 |
| aatgaaggta | tatgatgatg | tttctctctc | tctcctccag | tttctattta | tagatggaaa | 2700 |
| ctttaaatag | tccaatttat | atatatgagt | ctaaatttca | cattcttcaa | ctgctacatg | 2760 |
| tttcttttgt | attatttcta | tgatatcttc | aggaaagttt | gaaaaatatt | gtgttttgtt | 2820 |
| tagctggaag | atatgatcgg | cgtgagacat | caccatatag | gaggaggatg | ggaaggtggt | 2880 |
| gatcaacaga | atattgccta | tggacatcct | caggctcatt | ctcagggact | ataccaatct | 2940 |
| cttgaatgtg | atcccacttt | gcaaattggg | taaatcaaac | aacttttctt | gctttaagac | 3000 |
| atcaacttag | gttataaaca | gttagcagtt | tgctttaagc | ccaacattgt | ctttgtttca | 3060 |
| tagaggcttt | ggttaaaact | cgtgttgttt | agtctaagga | ttcagcactt | tgatgtctga | 3120 |
| agtatggaaa | atcaatctct | cagacttgaa | aatgtgggtt | tctattgttg | acttcgaaac | 3180 |
| tatgttgttg | tggtgttgca | aacagatata | gccatccagt | gtgctcagag | caaatggctg | 3240 |
| tgacggtgca | aggtcagtcc | caacaaggaa | acggctacat | ccctggctgg | atgctgtgag | 3300 |
| cgatacttct | tcccccaata | aagatcttaa | gcaagtactg | gtggggtctt | cgtggtgtga | 3360 |
| tcttagatct | tatgcatatg | aataataatg | ttattgcaca | agacttttgc | ttttgtagac | 3420 |
| acaagtggct | atagctgtaa | tagccttcaa | catctctctt | ctgtttcagg | atttgtttgt | 3480 |
| gcctattgta | attgcttata | tatgtatggt | ttgtataatg | tgtgaaatgt | taacatcgac | 3540 |
| catgtctcat | ctggtgaaga | tcttatcctg | tctatgcatg | ataccaaaa | | 3589 |

<210> SEQ ID NO 3
<211> LENGTH: 14940
<212> TYPE: DNA
<213> ORGANISM: Arabidopsis thaliana
<220> FEATURE:
<223> OTHER INFORMATION: AGL9 promoter

<400> SEQUENCE: 3

| | | | | | | |
|---|---|---|---|---|---|---|
| taaaatctgg | aagtttccag | ccctgataat | gttgcagaat | aaattagtgc | gcagtaagtc | 60 |
| tccaaaaga | gagaaactac | aaataaataa | accaagtcaa | attcattaac | aaggagaaca | 120 |
| gcatgaaatg | tttcccaaac | acacaaaatc | ttgactagcc | aacagcgctt | caaatgagga | 180 |
| agtaactaat | ttcagtagct | tgggtatggt | gaagtataat | taccttccac | cacacatatc | 240 |
| cgtagcctat | caccccaacg | ataatgatca | aaccatagtt | tctaccacct | gtacattgaa | 300 |
| ggaaagtgtt | aactgttttc | ttccgaattt | agatcaacag | taaacaaaga | atggtgttac | 360 |
| tctaagtctc | taatgtaatg | ccttcctaaa | tgctacaaag | aaaagccact | tatcagaaca | 420 |
| aagtatgtct | tgtttgatgc | gagaaaagta | gcaaagaga | ataaaacctg | aaatataatt | 480 |
| tcaaaataca | atgtctagaa | atcaagtgt | gcaaatcctt | tattcaagtt | tcatatcaaa | 540 |
| ccaattttga | catttctagt | gcagaacaga | aacaaaact | tcaatataaa | aaatataaa | 600 |
| aactccagag | gacctgatcc | tgaaggtgaa | acaatggtga | taggtctgtt | tgacccagc | 660 |
| aactgtatct | catgcctaag | actgttaacc | tacaaaata | aatagagctc | aggcaagaaa | 720 |
| ctattgattc | acgataaatc | tatgtcctca | gcaagtctat | attatccagc | tccatccgat | 780 |

-continued

```
agcttatcat cgccaataga ttaatgtgaa acttacctgg gccacaagta catcatcgtg    840
gggtttgcta gctgatttgc taggttcgtc ttgtttcagt tgcctgaata ccatctgtcc    900
acataaacaa aacccattgc ctcattttgc caaaccgcat catacacatg tgaagtcgcc    960
aaagcttttg cacaatatag aaattagaat accttaaaag caccagaaac caaattggag   1020
acatctggta agccccttc tttagaaaat gctgatccaa taagacctta aagtaacatt    1080
tgcaaaaatc acagtatagt tagtaattgc agtaacttgg acgaacatta agcatgtaca   1140
cgaaatcaat cgactcagca agttcacaat aattgtacta gtaggtgcat tcacagagaa   1200
actaaacata aacttctcct cagatgtatt cagagaatag ctatactcca ataaagtctt   1260
aaactttgag ccagtcaagt acactgatca aagggtttat gaaaaacact aacttcttat   1320
cctctaattg cgattaccca tagacgaaac caataaaaaa gcaatggaga actagagcac   1380
agtcactaca agaaataccc tataaaagta ccgacctgca ccgatgagga tggtgagctt   1440
cccgagcgga agagccatgg ctagagacga gcttatacgg cgaagaacta agatggcaaa   1500
cgaatccgcg tgagaatatc taagagagta ttggtaagag agagctgcag gaacgtaccg   1560
gtgaaacaga ggcgtttttt gggacgatga agtgaggcag cgagagagat acgacgtgcg   1620
actatattgt tcgcttgttg aggcaacaaa acagagttgc ttctaaaacc cgaaccgaaa   1680
tgtccggtct gattcggtct aaatcacgat taggttcgtt ttaaaaccta ggaggcaata   1740
accggacgga tcataaattc ataatagaga cagacaaatt ggtccattat taaaatcact   1800
tgggcatttg gggatgattc aaatgcccaa gttttctcaa atttggacga ttcattcacc   1860
taagacatac ttgagcaaca acaaagtgaa gtccactgtc atatcttatg tctcaaaaag   1920
tattgaaatg tgtcaattga tattggagag gcacactagc taagggatta ttcaatcaat   1980
ttccagcaat ttaattaaac ttatttgtag tgaaagtggg aagataaaag atctcaccct   2040
cacatgttca aaaaaaaag ttgaaaatgg aagtaattca acatgtagca tagagcccaa   2100
atatgtctca ttttttaat ccatataatc tcaaatcctc ttacttactt ctaaacatat    2160
ggttcccata atcataacaa tgctatgtta acatggccgg ttctaaagga agccaagtgc   2220
agcaactgcc ttacgcctct acgtgttaaa atgaaaatga agaccactga ccacttctat   2280
taaagcttca ttcactagtg tataattaca catttttta aggatttatg agtagtgatt    2340
gaggcccata tgtttgtatg tttgttttc ttactatatc attacttgac tataagagtt    2400
ggtttcctat tccattctct tttctaacag cctatatatg taaaaatcta agcaaaattt   2460
cttgtcaaga ggatgattgt acatttgtac ttggttatct cgccccggcc caaaacatac   2520
ctaaggccag gtgctatatc ctcaacctgc tttggcattc atcaatctac gaactttggc   2580
gtgaaacggt gacaagatta acaagattca ctctcaacta cgatgttcta ctatctcaaa   2640
tctttaaaaa agtggatcaa actgtcaaaa gtctagttcg atggactagc ttcaacactc   2700
ctccaaatct agttcgatgg actatatatt ctcttctgat gctatcctta tcttggatta   2760
ggcatctaaa ctatggtttt aatggtgtca tgaggtttta caacttacaa ggatgaaagt   2820
tatttactcc cagtcactat cttaatcaaa tgacaaaatg ttaactagtt tgagtgctta   2880
tatattagtt atgaatctga aatttattag tgtgtacata agtgatacaa cacttaaata   2940
acatctacat gagttttta ataacataat aatccattat agtagtttac ggcataaggt    3000
atgaaccaaa ttttcattg cacgctgaaa agtgaaaacc tttaaaatgc ataatgacta    3060
agagtctatg acaacagtaa cttactatat attagaggag gggtgaaaaa aaaagtagag   3120
```

```
agactggtcc aaaaacttaa ccccactcaa taaacccaga cgtgacttgt ttgacgataa    3180
ctccatcttt ctattttggg taacgaggtc cccttcccat tacgtcttga cgtggaccct    3240
gtccgtctat ttttagcaga ttaatccaac ggttcttatt ctttcttcga cccttcacga    3300
cattgcctca aagccgtccg attctcatct cacgcccaat ggaccacata tatcaccagt    3360
actccgcaac ttagctgtcg tgtaggattt cacgtggcat ttatttgttc tagtttgtag    3420
tgcaaacatt gcaagttgat atggtcccct atcgatcacc gtcgtctctt tagcttcaca    3480
tcgagattct tctttctttc ctacgtgtaa tagcattttt gattttgaga atttctttag    3540
aaccgttgga tctctcatcg ttggttgatc catccatcca aatgggacct gtgtgtgctc    3600
catccagggc atatgatccc aaagccaaaa gagtatttcc aagtgctttc tttctttctt    3660
tctttctttc ttactaacct ttttttttct tatgctttag actaagaaat ttattcggcc    3720
atatccactt ttacgaatat acttcttaca agatctagat tttttgagt taattcggtg    3780
tataacat tggcatggac tgcaattaag taatggtaat gtgatcatga tgcgatgtgt    3840
cgttatcagt agtataatat tgatgggcta ccctggaaaa caaaattacg tgttatatgt    3900
acacaatttg gtagaaccgt agaaattaaa ctgaataaaa ccttctataa tgttcaaaat    3960
tatatggtac agattaatac ggaaaaacat tcacgcttta cgtaacaatt aagtggaaag    4020
taaaattatc ccaaaaatat ttatatcaca tcattgttat atttctaagt ttttttatat    4080
ctctaatggt atatgtttta cagattgttt tttgggaaaa ttcttaaaga gacttgaaga    4140
atgttttttt tttatttct tgaaatgttt gacacttgaa accgtttaaa aactcaaata    4200
tagtatatat cattgttggt ctcataccct gtaattcacc acatatatta tcaatgggga    4260
agatttgaaa attttggggg gatcacaaaa cgaaggaaag agtacaaaaa gagaaggaaa    4320
agatagaaga tatatgtttt taacttcatt ggtatgacat caataaataa atagttgaat    4380
gtactttagt ttctcttttg gtttaatgca catcatctcg atcaattgtc atcatcttac    4440
attgaattat acgaccagat ctgataacaa gtgaattcgt acttgcccctt cccttcttc    4500
tcatacgtcc ttctaactaa ttttgattgt aacttataat tatataacca tatttaattt    4560
tatttatct aaaaccaatt gaagcaaatt aaaatatcat aaatcttgag tcccacatga    4620
agacaatata taaaactcgt gcaaatttgc ttaaaatgct tctatgagac catgaccaag    4680
tgagattaat aagcgattca atgtgcaaat caaaagagaa aagaagctaa tgggtttaaa    4740
tataaccaaa cagaataata atgctatgtt tagttttttct aattgaatca tacctttgtg    4800
tccatcacct acttaccggt cagaataaag caattacgtc tgcaaccaaa aagcactaag    4860
actttcggtc agacatgatc tctaacatcg gacgaaccct aagataacca aaataaacta    4920
tatcttatat tcaaatctct gtttatttta tccatttatg ttttctttct ttcccataat    4980
ttttttttgtg tctcatcaga ctctcttacc aaactgaatt tatcaacatg gtttttttt    5040
tggccacatc aaaatggtgg tttataaagt agactaatac aaaagacatt tctgttaatt    5100
tcactaacaa aaataatctt agcagtacta tagattggaa aaggaaaagc aaatctagca    5160
gtaagattta tcaaaactag cagtaagagt tttagatatc atgaaaacat cacaaacgag    5220
tagtgtttta ctttacattt ttaaccaatc acaagggtag ttccgtaagt tgggaaaatc    5280
gtacgaggct tcacctagtt aaggttaggt cacatgattc cctgaactcg attttataag    5340
taaaaagaa aaatttataa aatcaaaatt ttttatataa aaaaatcagg tggatttatc    5400
agaccctacc atcgagatgt cgacacgtgt ccaaactcat tcattgccct actattttct    5460
gtttagggtt gcaatcactc atcgcacacg cgccatctcc accttccatt attaatctct    5520
```

```
cattttcaac atcacactct tacgaatcat acgattttaa tatctctgtc tctctcaacg   5580
tattaaataa aaatggtttt aaatgttagg gttttttgta ggattttcaa ttattaatct   5640
ctataattcg atgaactaag taaaaaagca tcaaactttc ttggcagaat cacatttttc   5700
tctaaactaa atatggactg aaattgaaaa attaaaccac tagctagaat aaagtgttgg   5760
tgagagtgga actctaatttt ctctccttta ctaattatgt ataaacacaa aaatgcacca   5820
aatttttagg tttgaaaata tctaagcatg ataggtaa ttaacatttt ttctttcaat   5880
tttgcaatat ttgaataaat cctatgaggg tctttggtac acaataattg gagggtatat   5940
agttgagtct gagagtatat tagaaagaga atatttcaag taatgaagct gacatgttta   6000
tatgtacttt gagagaagtg ttgtgagatt tgtacaaatg tatatgtaca ctttaaaaag   6060
caatataaga tagataaaaa aaatataaag aaaaaaagaa agaaagaaag aaagaaagag   6120
agaggctcat atatatatag aattgcttgc aaggaaagag agagagagag attgagatat   6180
cttttgggag aggagaaaga aaaagaaaat gggaagaggg agagtagaat tgaagaggat   6240
agagaacaag atcaataggc aagtgacgtt tgcaaagaga aggaatggtc ttttgaagaa   6300
agcatacgag ctttcagttc tatgtgatgc agaagttgct ctcatcatct tctcaaatag   6360
aggaaagctg tacgagtttt gcagtagttc gaggtatata tctacttttg tatatatatt   6420
acttataaca taaacatttt atatacatat taagtaacac aaaaatgtct tgtatgtatg   6480
ggtctctctg tgatgtgttg ttgtgtcgta cgtacgtgtt ctatcatatc cttttaaaag   6540
aagcaaagag gaaaaaaat ttgggatacc ccaaatctgt atcatttat aacaagtttg   6600 ctttttttgat gttcttttgt gtttctcttt gatttccatt tttgttttttg atttttttttc   6660 tatttctctt tacatctatc aaagtttttt ttcttatatt ttattgctta tttgtttgtc   6720
tacttaattc acattatctg agagaagaac aatctatctg atatgaaatt agggttaatt   6780
tctcttgtga gtactcttta attcacataa gcttaaagtt tccaccttttt gattctgggg   6840 gtcgtccaat tcgatcaaat cactcaattt tgttgtcaga ttgatataag ttcataggg   6900 gatattgttt ccacgacaat ccattttagt aacccttagg ggtttccaat tttgggtttt   6960
gaattgacgc taatgtcaaa ttcatctaaa gtccgttgga tatgtatact tggggatggg   7020
attcatcctt ttttctgggt tctttagatc ttctcttaaa agactaacag attttgttgt   7080
aaaccctagg aaacagttaa aaatcccatt tttaaaaaca tgttttgaac ttgatgagta   7140
agattaatgg aagaaatgat gttttttgtgt ggtgtgaagc atgcttcgga cactggagag   7200
gtaccaaaag tgtaactatg gagcaccaga acccaatgtg ccttcaagag aggccttagc   7260
agttgtaccc aattctcttc tctttcttct aattacctta attaattact ctcaattttt   7320
actttgattt ttagagtcaa atgattaatg ttataatttg tcatatactt caggaactta   7380
gtagccagca ggagtatctc aagcttaagg agcgttatga cgccttacag agaacccaaa   7440
ggtaaactaa ttagcttctt cagctacctt cagagagtgt ttgttttttt agtagatttt   7500
tttgatggtt ttgatgttga ataggaatc tgttgggaga agatcttgga cctctaagta   7560
caaaggagct tgagtcactt gagagacagc ttgattcttc cttgaagcag atcagagctc   7620
tcagggtact actttgttca tcaatatctt tatacactga tctatttcca tagtaagatt   7680
aaatttggtg tttaattctg cagacacagt ttatgcttga ccagctcaac gatcttcaga   7740
gtaaggtaaa taagaaaca ctcattctcc tctctaaatt cctcatctaa aagtaatgta   7800
accaagaaaa cacaaatatt tggagcagga acgcatgctg actgagacaa ataaaactct   7860
```

```
aagactaagg gtaattaata tacattctca tatcaccaaa ttaatgcatc actaaatttg    7920
gttataatgt gtgtgtgtat atacatatgt gacagttagc tgatgggtat cagatgccac    7980
tccagctgaa ccctaaccaa gaagaggttg atcactacgg tcgtcatcat catcaacaac    8040
aacaacactc ccaagctttc ttccagcctt tggaatgtga acccattctt cagatcgggt    8100
aactttagac tagtataacc aatttgattt gagttctatt ataagctttt cttaagaaag    8160
tatctcaaac tactaaattt tatggagcag gtatcagggg caacaagatg gaatgggagc    8220
aggaccaagt gtgaataatt acatgttggg ttggttacct tatgacacca actctatttg    8280
aatctttctc acttaatcaa tccctctctt ttttttttga cattttttaag atgatgtttc    8340 tatttttatta cctctctcat gttttctgtc ttgtgtgcat gtgtgtgtgt aatgtttatg    8400
cccttctatt attcaataat tttttcgaca attttgcttc ctatttttac ccattactcc    8460
taaacttcct gatccagttt cttttaaaat aactcccatt ttatgcatgt tatctaaccca    8520 attctcttaa ctatgattta tggtacgata taactcacag tctcacacta tctatttggt    8580 gttttttttgt ttgagtcttg agaagggacc gcttgtttat ctctcttgtt aaagagcaac    8640
tcactggcca ctgcttatgt atctgtaggc cccacctata tcattttggc tatatctata    8700
cttttgtaga gggagtatta ctatagagaa gaagataaat ttggttctaa tatatcttgc    8760
aggtagttga tattctcaat tatcatgaag atttgataga caagtttatc agataccta    8820 aacataggtt taagatctca attgaaatgt gaattcaccc gacgattaga gttacgatct    8880
aaggaagcgt tcttgaatt ttgagttgt ttgatcaaga gtagaatgct tttctattac    8940
taaggttgtt aatgcttata ttccatgacc aaggccaaga gaacaaacaa aaacatggtg    9000
cctcttgatg tatagtaatg gctcttaatg gtcatataca gagaaaaaaa gattaatgtc    9060
gttgcacaag cttgaagtta cttactcctc gtcttcctca ttagtgtctt cgtcttcctc    9120
atcctcatcg ctcccaatat agggcttcat ctacttgaaa accaaatgct catgcagtgg    9180
aaaaagataa cagaggttca aattaaggca aacaaaacta caagtgagaa agggaaacta    9240
caagtggtaa gatgtaatgt tttgactcaa aaccagatca gacaatgaaa aaaagtattg    9300
atacaaaaag tccatccgga agcataatta ccgcttgcag gatgtcatca gagatgtctg    9360
ttagtcggcc aatggcatag atggtgagcg gaccagagta gcgtaaatcc tctaaatact    9420
gtctaaaagc cggaccgacc cgacaaggat cacagtcaag gggaatagga cacctattga    9480
tatcccaaaa gactgttgtt acagccacat catccttgtc caactgggta gcccaaaggg    9540
aaactagttg tggtaagagc ttgtttgact caaaaaatgg ctaactagga tgatgctgaa    9600
ttaccatctg ttcatgtttt tgactagaga gatgggtagt gaaatttca aagcctttgc    9660 aaaacgcctg tgggacctgt ttcagaaaaa gacttaaaag acttgagact caaggaaaat    9720
aatatccatt atataaagat gacaacaaat attaacggaa gtaggagtga ttgagaacga    9780
ttctagtaga agagacggct cgcaggacgt cgttttataat aggccaatgg cagagatagt    9840
gagaggaccg gagtagccta aattcttttaa atgtcgtttg atacacggac caactagacg    9900
agcatcatac tcagagggaa ccggacacgt cttgatatcc cagaagaccg atgttacggc    9960
cttagcttgc tgccgcgttg ccttcatcat catcttctcc ttttaatcta taacgaaat    10020 caaacatcag ataagcatt cgaaaagata gattgacaca ggttaaatca tccacttcag    10080
agaaaaagag agggacatgg ccgtaaacaa tgagataagg atcggcctaa tgtttataat    10140
gggcttgcgt ttaatgggcc tacagttttct tgaatcagcc ttatgcatga gtcctagtat    10200
tttatcaact tttttttttc atctttcttt agttacaata gatttaaagt gttttttgtt    10260
```

```
aatgccattg caaaatttgg taactgttta taacattgtt cctcacttca aaatttaaag   10320
caccattaat aaaagctata catataatta taacttgggt tttgtgcaaa aaaaacaaac   10380
aaattaacct ttcattttaa ataaatgcaa ttcaataccg caatatcaaa agtaacccgt   10440
ataaccttta ttcgtgtata gattttagaa acagtataag tcaaattatc aaaactatgt   10500
tgttttaagc attttaaaaa taagaataat aataatgttg aagggtggat ttgaacccat   10560
gaactataga acaaaccaaa gcatgcataa ccacatgcgc cgaacaaacc aaaaactcat   10620
ggctttgtta aacatataaa aatattcgaa taaaaaatgt ggggaacttg ttaccagttt   10680
tggttctttt tggagccatt ttttcaaca cagatattgt taaggagttt caggtaaaac   10740
tgtatattat gcagggaacc acagtaggct ataatgaaag tcacactgtg aagttagcag   10800
acaagttttt acttaaagat gtgagttgtg atctttttga tgtaagtctt gatgtatatg   10860
ttgacaaatt atataagttt gtattgcata ttctatgact tacgaagttt ctatgcaaga   10920
aaagccggga gaaaatttcc gtcaagtaac taagagatcg taattcttgt ctgaagaaca   10980 acccttttt attatttgag tttaggttgc caacagtgaa caaagggacg agataccata   11040
tgacaaatat cctctaacgc catttcaaca gttaatcaac agtgtcggct atatgcatgt   11100
gctaacaatg cacaagaaca ttgtcaccat cccgtgaata tgaatattaa tgattatgaa   11160
cgagtttgta gagttccaag aggaaggtac taccttctca tactcattga tcatatattt   11220
tgtttcttgt ttgttttagt aactagggtt attcggattg ttttttcaaaa aataatagtaat   11280 atgtcaacta tatttataaa aaaaaaaact aaataacttt tgtacaattg atcattttt   11340 aaatatatca taaagattca tcaatatatg aacatatatt tttaacaatt acactaattg   11400
gctatatagt gtatagttcc ttttgtggag aggtttaagt tcagttcaga gattattgta   11460
cttggtaaaa tatttgtcct tgttaattag ttcatcttct agaatacaga tttgggccat   11520
gtagtttccc agaaaacacc ggaaaaaaaa ttcacacttc acaccagaaa caataaacga   11580
ggaacagagc ccaaactcat ccctataatt gggcccaaaa aaagcagagc aaaccaaacc   11640
aaaatcaagt aaatccattt acaaatatgc tttataatta ttattttct caaccacaaa   11700 tatgctttat aatttatgta aatgttatat gaattattta cgatttattt taattacttt   11760
atcttggaat tatcttacga agttaatgaa aatatttaa atatctaatt tatatatgtc   11820
tggactaaaa taaatagaaa tatctgtatt ccaatcatca caaaaaaaaa attctcatca   11880
tctttgatat atagaaagtt tttaaaattt cagtttcaca gattttacca attatagttt   11940
tataagctta tgctaattat gtgatcaatg caaacaaaag ttgacaataa taaaatgaag   12000
tcaaatatga tagattccta ctataaatat agactcgtga ataatactcg aatcagtctc   12060
tgaggttttg ctggaaaaga aaaccgaag agctcaaaac agagtgcgtt tgtttctggg   12120
aatcttcaag cctctcactt gcgaagacga agcttactcg taaggtgatt atcttcttct   12180
tcttcttctt ttcaattcct ttttcgttca tctgaaatgt gaaatcatgt gacgtgacga   12240
ttaggttaac gatcgaattt cttaatttcg tatatgatta tcttctagtt tcttgatcag   12300
cacatcttgt tgttttcttt caatcgagac tgattctaga tgttcttaag gatcttgttc   12360
gatgaacttt gcatgaatca tccatatcga cgaactggtc tgatcttctt gttgttatgg   12420
attaagtttc ttgagataca agaaaggctt caatgatcaa tctgatctgt tttgatgaac   12480
acaaatcttt atctttgaac catggataag gtcaatttca caccatggct ggaggaagtt   12540
tatcaccggc gtcatctttg gaagatgtaa aggcatacgt caatgctgtg gaggtcgcat   12600
```

-continued

```
tgcaggaaat ggaacctgca agatttggaa tgtttgtaag actctttcgt ggttttacag    12660
ctcctaggtg tgtttggttt gctcttaaac agtctaaaga acaatgacac atgtgagaat    12720
tgattctgat gttattttc tctttgtagg atcggtatgc ctactttcag tgcacgcatg     12780
caggacctct tgaaagatca cccgagtctg tgtcttggtt taaatgtctt acttccacct    12840
gagtatcagt taaccatacc tcccgaggct agcgaagagt ttcataaggt ggttggaaga    12900
agcgtaccag taccaccaaa ggtggttgga agaagtctac cacgtccgga gcctaccata    12960
gatgatgcga cttcatacct tattgctgtg aaggaagcct ttcatgatga acctgcaaaa    13020
tatggggaaa tgcttaagct cttgaaagat tttaaagctc gcaggtatgt attagttctt    13080
ttctccatgt tatgtttgat tttttcagtc tacagaacaa acacattatg tgaattgatt    13140
ctgatgttac taagtctctt tgtagagtcg atgccgcttg tgtcattgct agggtggagg    13200
aactcatgaa agatcacttg aatctgcttt ttggtttctg tgtcttcctt tcagctacaa    13260
cgagttttac cacgaagctt aaggtataga gtgcttatag ttaccatttg atgtttccta    13320
tatgttaact tgtggtttaa gtaacaaaat tgtccatgtg caggcaaggt ttcagggcga    13380
tggtagtcaa gtagttgact cagttcttca gataatgaga atgtacggtg agggaaacaa    13440
gtccaaacat gatgcgtatc aggaggtagg cttcttggta ggatactttg tgttgtgtgt    13500
tgcactttct tagttctttg gtttgatttg ctttgttatc ttttgcaggt cgttgcactt    13560
gttcagggtc atgacgattt agtcatggag ctttcacaaa ttttgactga tccacctact    13620
ggagtctaga gatagccaga tagctaagga gagtactgga agactgtaat ataccataag    13680
agacgaaaaa gaaagtagag cttctcacga aaagagagtg ttttttagttt tcttttgcaa    13740 acattagagt tttgtttgat taacatgaca ttcaaaaata tgctatgctt ctatgttgag    13800
gtgtacaatg aattggtgta taagagacta aaagagagtg tatagtttct ttgttgaggt    13860
ttcttttatg ttgaggtgtt caatatgcta ttttcagggt aatctttta taagaaactg    13920 agaagggaaa cactcaaaaa acagagttca acgtagaaac aaaaacagag aggtgaactc    13980
atgaaagatc aatttaacct gcttgtgatg attggcttat caagagaatt gaagagattc    14040
acgattacac aaattcaatt cttaaagaca agagtagact gctaattctt attaaggctg    14100
ttaatgcttc ttgagagcat tgaccttttc cctgaggtaa taaagcttgg ctcttcttac    14160
tttcttcttg tccaccacct taatcaccct caggtttggg gaatacctgt caccaaaaca    14220
cctccactta catcagtatt ttccatgacc aaggcaaaca aagagaacat acaaaacatg    14280
gtggctcttg attataataa tggctcttaa tggtcatata caaaagtctg agagaaaaag    14340
attaaagtgg ctgcacaagc ttgaagcttg aagttactta caaggggaac atggattcga    14400
cgcccactcc agcaacaagc cttctaattc taaatgttga gttgagacca gcattacgcc    14460
ttgctatgac gacgcctttt acgattgata cacgcctctt gttctcaggc acttcctgtt    14520
caaacaaagt aaatgaaagg tttcacttag aagatgaaag atagtttgat cttactcacc    14580
caagaaaaag aaattacaac ctaggccaac agtagttacc actttagct gcacaatgta     14640 accaggcttt atctctggaa tctctctaag agttctcact tcctcaactg cttccttgtc    14700
tacaatctgc agaggattgt gacatcggtg cttccttgtc tacatgatat atctaaatac    14760
aagtgtcaag ttcgagttgt agtacctgca taatatgctt agcggtttta tcaagccgct    14820
taaacttgat tctctgaggc acaacacaat ctgactcagg ggatccttga acagaatctc    14880
cagtggtgga aaaacacctc gacgaaaagt tttgtttctg ccaaaaaaat attcccaaga    14940
```

-continued

<210> SEQ ID NO 4
<211> LENGTH: 1294
<212> TYPE: DNA
<213> ORGANISM: Arabidopsis thaliana
<220> FEATURE:
<223> OTHER INFORMATION: AGL2 cDNA
<220> FEATURE:
<221> NAME/KEY: CDS
<222> LOCATION: (387)..(1133)
<223> OTHER INFORMATION: AGAMOUS-LIKE 2 (AGL2)

<400> SEQUENCE: 4

| | |
|---|---|
| ccctcacaca tttcttatct tttgctctca atagattcca ttgattcaaa acaaaatttt | 60 |
| cattaagatt tcacaacctc cacacacttc caaacacaat taaagagagg aaaaagaatc | 120 |
| aataaccctc taaataaaaa atcagacaaa cagaagtttc ctcttcttct tccttaagct | 180 |
| agtacctttt gttcttgaaa ttagggttaa tttcttttt ccaaatacca tcaattctcc | 240 |
| agaccataaa aactcaaaaa gatcagatct ttcctctgaa aaagagatac ccaacttatg | 300 |
| tttttgtgtg tctgtatata gataaacatt acatacccat atttgtgtat agacataaaa | 360 |
| agtggaaatt aagtaacaa aagaa atg gga aga gga aga gta gag ctg aag | 413 |
|                                           Met Gly Arg Gly Arg Val Glu Leu Lys<br>                                           1               5 | |
| agg ata gag aac aaa atc aac aga caa gta acg ttt gca aag cgt agg<br>Arg Ile Glu Asn Lys Ile Asn Arg Gln Val Thr Phe Ala Lys Arg Arg<br> 10                  15                   20                 25 | 461 |
| aac ggt ttg ttg aag aaa gct tat gaa ttg tct gtt ctc tgt gat gct<br>Asn Gly Leu Leu Lys Lys Ala Tyr Glu Leu Ser Val Leu Cys Asp Ala<br>             30                   35                   40 | 509 |
| gaa gtt gct ctc atc atc ttc tcc aac cgt gga aag ctc tat gag ttt<br>Glu Val Ala Leu Ile Ile Phe Ser Asn Arg Gly Lys Leu Tyr Glu Phe<br>        45                   50                   55 | 557 |
| tgc agc tcc tca aac atg ctc aag aca ctt gat cgg tac cag aaa tgc<br>Cys Ser Ser Ser Asn Met Leu Lys Thr Leu Asp Arg Tyr Gln Lys Cys<br>    60                   65                   70 | 605 |
| agc tat gga tcc att gaa gtc aac aac aaa cct gcc aaa gaa ctt gag<br>Ser Tyr Gly Ser Ile Glu Val Asn Asn Lys Pro Ala Lys Glu Leu Glu<br>75                   80                   85 | 653 |
| aac agc tac aga gaa tat ctg aag ctt aag ggt aga tat gag aac ctt<br>Asn Ser Tyr Arg Glu Tyr Leu Lys Leu Lys Gly Arg Tyr Glu Asn Leu<br> 90                  95                  100              105 | 701 |
| caa cgt caa cag aga aat ctt ctt ggg gag gat tta gga cct ttg aat<br>Gln Arg Gln Gln Arg Asn Leu Leu Gly Glu Asp Leu Gly Pro Leu Asn<br>                   110                 115               120 | 749 |
| tca aag gag tta gag cag ctt gag cgt caa ctg gac ggc tct ctc aag<br>Ser Lys Glu Leu Glu Gln Leu Glu Arg Gln Leu Asp Gly Ser Leu Lys<br>             125                 130               135 | 797 |
| caa gtt cgg tcc atc aag aca cag tac atg ctt gac cag ctc tcg gat<br>Gln Val Arg Ser Ile Lys Thr Gln Tyr Met Leu Asp Gln Leu Ser Asp<br>       140                 145                 150 | 845 |
| ctt caa aat aaa gag caa atg ttg ctt gaa acc aat aga gct ttg gca<br>Leu Gln Asn Lys Glu Gln Met Leu Leu Glu Thr Asn Arg Ala Leu Ala<br>155                  160                  165 | 893 |
| atg aag ctg gat gat atg att ggt gtg aga agt cat cat atg gga gga<br>Met Lys Leu Asp Asp Met Ile Gly Val Arg Ser His His Met Gly Gly<br>170                  175                  180              185 | 941 |
| tgg gaa ggc ggt gaa cag aat gtt acc tac gcg cat cat caa gct cag<br>Trp Glu Gly Gly Glu Gln Asn Val Thr Tyr Ala His His Gln Ala Gln<br>                   190                 195               200 | 989 |
| tct cag gga cta tac cag cct ctt gaa tgc aat cca act ctg caa atg<br>Ser Gln Gly Leu Tyr Gln Pro Leu Glu Cys Asn Pro Thr Leu Gln Met | 1037 |

-continued

```
                    205                 210                 215
ggg tat gat aat cca gta tgc tct gag caa atc act gcg aca aca caa    1085
Gly Tyr Asp Asn Pro Val Cys Ser Glu Gln Ile Thr Ala Thr Thr Gln
            220                 225                 230 gct cag gcg cag ccg gga aac ggt tac att cca gga tgg atg ctc tga    1133
Ala Gln Ala Gln Pro Gly Asn Gly Tyr Ile Pro Gly Trp Met Leu
    235                 240                 245 gaatcatgta ctgtgatgaa gctcacccac aaaagacctt atatatatat aaagtataga  1193
tacaagactt ggatttgtag acataagtgg ctaatataat ggtcctgagg atcttctaga  1253
catttgtatc ttttgggaat ccttgcttat attaagaatt c                     1294
```

<210> SEQ ID NO 5
<211> LENGTH: 248
<212> TYPE: PRT
<213> ORGANISM: Arabidopsis thaliana
<220> FEATURE:
<223> OTHER INFORMATION: AGAMOUS-LIKE 2 (AGL2)

<400> SEQUENCE: 5

```
Met Gly Arg Gly Arg Val Glu Leu Lys Arg Ile Glu Asn Lys Ile Asn
  1               5                  10                  15

Arg Gln Val Thr Phe Ala Lys Arg Arg Asn Gly Leu Leu Lys Lys Ala
             20                  25                  30

Tyr Glu Leu Ser Val Leu Cys Asp Ala Glu Val Ala Leu Ile Ile Phe
         35                  40                  45

Ser Asn Arg Gly Lys Leu Tyr Glu Phe Cys Ser Ser Ser Asn Met Leu
     50                  55                  60

Lys Thr Leu Asp Arg Tyr Gln Lys Cys Ser Tyr Gly Ser Ile Glu Val
 65                  70                  75                  80

Asn Asn Lys Pro Ala Lys Glu Leu Glu Asn Ser Tyr Arg Glu Tyr Leu
                 85                  90                  95

Lys Leu Lys Gly Arg Tyr Glu Asn Leu Gln Arg Gln Gln Arg Asn Leu
            100                 105                 110

Leu Gly Glu Asp Leu Gly Pro Leu Asn Ser Lys Glu Leu Glu Gln Leu
        115                 120                 125

Glu Arg Gln Leu Asp Gly Ser Leu Lys Gln Val Arg Ser Ile Lys Thr
    130                 135                 140

Gln Tyr Met Leu Asp Gln Leu Ser Asp Leu Gln Asn Lys Glu Gln Met
145                 150                 155                 160

Leu Leu Glu Thr Asn Arg Ala Leu Ala Met Lys Leu Asp Asp Met Ile
                165                 170                 175

Gly Val Arg Ser His His Met Gly Gly Trp Glu Gly Gly Glu Gln Asn
            180                 185                 190

Val Thr Tyr Ala His His Gln Ala Gln Ser Gln Gly Leu Tyr Gln Pro
        195                 200                 205

Leu Glu Cys Asn Pro Thr Leu Gln Met Gly Tyr Asp Asn Pro Val Cys
    210                 215                 220

Ser Glu Gln Ile Thr Ala Thr Thr Gln Ala Gln Ala Gln Pro Gly Asn
225                 230                 235                 240

Gly Tyr Ile Pro Gly Trp Met Leu
                245
```

<210> SEQ ID NO 6
<211> LENGTH: 1349
<212> TYPE: DNA
<213> ORGANISM: Arabidopsis thaliana -continued

```
<220> FEATURE:
<223> OTHER INFORMATION: AGL4 cDNA
<220> FEATURE:
<221> NAME/KEY: CDS
<222> LOCATION: (339)..(1091)
<223> OTHER INFORMATION: AGAMOUS-LIKE 4 (AGL4)

<400> SEQUENCE: 6
gattcacaaa aacttttctt cagattcaca atctcatcac aacccttcaa aaagagaaaa      60
gatctaaaga ataaacaaga gccctaatat caaatcacaa ccaaaaaaac caaagaaagc     120
taattaaagt tttctctcta gctattcctc ttcttttctt gttcttgaaa actagggttt     180
acttcaccaa aagataagat ctttccccag aaaaagcaat acccaagtca tgtttctgtg     240
tgtctgtata tagataaaac attacatacc ctaataaggt tacacaaata gctataaaag     300
agggaaaata agatagggat ttttgggggt gaggaaag atg gga aga gga aga gta     356
                                          Met Gly Arg Gly Arg Val
                                            1               5 gag ctc aag agg ata gag aac aaa atc aac aga caa gtg acg ttt gct      404
Glu Leu Lys Arg Ile Glu Asn Lys Ile Asn Arg Gln Val Thr Phe Ala
            10                  15                  20 aaa cgt aga aat ggt ttg ctg aaa aaa gct tat gag ctt tct gtt ctc      452
Lys Arg Arg Asn Gly Leu Leu Lys Lys Ala Tyr Glu Leu Ser Val Leu
        25                  30                  35 tgc gat gct gaa gtc tct ctc atc gtc ttc tcc aac cgt ggc aag ctc      500
Cys Asp Ala Glu Val Ser Leu Ile Val Phe Ser Asn Arg Gly Lys Leu
    40                  45                  50 tac gag ttc tgc agc acc tcc aac atg ctc aag aca ctg gaa agg tat      548
Tyr Glu Phe Cys Ser Thr Ser Asn Met Leu Lys Thr Leu Glu Arg Tyr
55                  60                  65                  70 cag aag tgt agc tat ggc tcc att gaa gtc aac aac aaa cct gct aaa      596
Gln Lys Cys Ser Tyr Gly Ser Ile Glu Val Asn Asn Lys Pro Ala Lys
                75                  80                  85 gag ctt gag aac agc tac aga gag tac ttg aag ctg aaa ggt aga tat      644
Glu Leu Glu Asn Ser Tyr Arg Glu Tyr Leu Lys Leu Lys Gly Arg Tyr
            90                  95                 100 gaa aat ctg caa cgt cag cag aga aat ctt ctt gga gag gat ctt gga      692
Glu Asn Leu Gln Arg Gln Gln Arg Asn Leu Leu Gly Glu Asp Leu Gly
        105                 110                 115 cct ctg aat tca aag gag cta gag cag ctt gag cgt caa cta gac ggc      740
Pro Leu Asn Ser Lys Glu Leu Glu Gln Leu Glu Arg Gln Leu Asp Gly
    120                 125                 130 tct ctg aag caa gtt cgc tgc atc aag aca cag tat atg ctt gac cag      788
Ser Leu Lys Gln Val Arg Cys Ile Lys Thr Gln Tyr Met Leu Asp Gln
135                 140                 145                 150 ctc tct gat ctt caa ggt aag gag cat atc ttg ctt gat gcc aac aga      836
Leu Ser Asp Leu Gln Gly Lys Glu His Ile Leu Leu Asp Ala Asn Arg
                155                 160                 165 gct ttg tca atg aag ctg gaa gat atg atc ggc gtg aga cat cac cat      884
Ala Leu Ser Met Lys Leu Glu Asp Met Ile Gly Val Arg His His His
            170                 175                 180 ata gga gga gga tgg gaa ggt ggt gat caa cag aat att gcc tat gga      932
Ile Gly Gly Gly Trp Glu Gly Gly Asp Gln Gln Asn Ile Ala Tyr Gly
        185                 190                 195 cat cct cag gct cat tct cag gga cta tac caa tct ctt gaa tgt gat      980
His Pro Gln Ala His Ser Gln Gly Leu Tyr Gln Ser Leu Glu Cys Asp
    200                 205                 210 ccc act ttg caa att gga tat agc cat cca gtg tgc tca gag caa atg     1028
Pro Thr Leu Gln Ile Gly Tyr Ser His Pro Val Cys Ser Glu Gln Met
215                 220                 225                 230
```

```
gct gtg acg gtg caa ggt cag tcc caa caa gga aac ggc tac atc cct      1076
Ala Val Thr Val Gln Gly Gln Ser Gln Gln Gly Asn Gly Tyr Ile Pro
                235                 240                 245 ggc tgg atg ctg tga gcgatacttc ttcccccaat aaagatctta agcaagtact      1131
Gly Trp Met Leu
            250 ggtgggtct tcgtggtgtg atcttagatc ttatgcatat gaataataat gttattgcac     1191 aagactttg cttttgtaga cacaagtggc tatagctgta atagccttca acatctctct     1251
tctgtttcag gatttgtttg tgcctattgt aattgcttat atatgtatgg tttgtataat    1311
gtgtgaaatg ttaacatcga ccatgtctca tctggtga                             1349
```

<210> SEQ ID NO 7
<211> LENGTH: 250
<212> TYPE: PRT
<213> ORGANISM: Arabidopsis thaliana
<220> FEATURE:
<223> OTHER INFORMATION: AGAMOUS-LIKE 4 (AGL4)

<400> SEQUENCE: 7

```
Met Gly Arg Gly Arg Val Glu Leu Lys Arg Ile Glu Asn Lys Ile Asn
 1               5                  10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ser Leu Ile Val Phe
            35                  40                  45

Ser Asn Arg Gly Lys Leu Tyr Glu Phe Cys Ser Thr Ser Asn Met Leu
        50                  55                  60

Lys Thr Leu Glu Arg Tyr Gln Lys Cys Ser Tyr Gly Ser Ile Glu Val
 65                  70                  75                  80

Asn Asn Lys Pro Ala Lys Glu Leu Glu Asn Ser Tyr Arg Glu Tyr Leu
                85                  90                  95

Lys Leu Lys Gly Arg Tyr Glu Asn Leu Gln Arg Gln Arg Asn Leu
                100                 105                 110

Leu Gly Glu Asp Leu Gly Pro Leu Asn Ser Lys Glu Leu Glu Gln Leu
            115                 120                 125

Glu Arg Gln Leu Asp Gly Ser Leu Lys Gln Val Arg Cys Ile Lys Thr
        130                 135                 140

Gln Tyr Met Leu Asp Gln Leu Ser Asp Leu Gln Gly Lys Glu His Ile
145                 150                 155                 160

Leu Leu Asp Ala Asn Arg Ala Leu Ser Met Lys Leu Glu Asp Met Ile
                165                 170                 175

Gly Val Arg His His His Ile Gly Gly Gly Trp Glu Gly Gly Asp Gln
            180                 185                 190

Gln Asn Ile Ala Tyr Gly His Pro Gln Ala His Ser Gln Gly Leu Tyr
        195                 200                 205

Gln Ser Leu Glu Cys Asp Pro Thr Leu Gln Ile Gly Tyr Ser His Pro
    210                 215                 220

Val Cys Ser Glu Gln Met Ala Val Thr Val Gln Gly Gln Ser Gln Gln
225                 230                 235                 240

Gly Asn Gly Tyr Ile Pro Gly Trp Met Leu
                245                 250
```

<210> SEQ ID NO 8
<211> LENGTH: 827
<212> TYPE: DNA
<213> ORGANISM: Arabidopsis thaliana

```
<220> FEATURE:
<223> OTHER INFORMATION: AGL9 cDNA
<220> FEATURE:
<221> NAME/KEY: CDS
<222> LOCATION: (10)..(819)
<223> OTHER INFORMATION: AGAMOUS-LIKE 9 (AGL9)

<400> SEQUENCE: 8 cccggatcc aaa atg gga aga ggg aga gta gaa ttg aag agg ata gag aac      51
            Lys Met Gly Arg Gly Arg Val Glu Leu Lys Arg Ile Glu Asn
              1               5                  10 aag atc aat agg caa gtg acg ttt gca aag aga agg aat ggt ctt ttg        99
Lys Ile Asn Arg Gln Val Thr Phe Ala Lys Arg Arg Asn Gly Leu Leu
 15                  20                  25                  30 aag aaa gca tac gag ctt tca gtt cta tgt gat gcg gaa gtt gct ctc       147
Lys Lys Ala Tyr Glu Leu Ser Val Leu Cys Asp Ala Glu Val Ala Leu
                 35                  40                  45 atc atc ttc tca aat aga gga aag ctg tac gag ttt tgc agt agt tcg       195
Ile Ile Phe Ser Asn Arg Gly Lys Leu Tyr Glu Phe Cys Ser Ser Ser
 50                  55                  60 agc atg ctt cgg aca ctg gag agg tac caa aag tgt aac tat gga gca       243
Ser Met Leu Arg Thr Leu Glu Arg Tyr Gln Lys Cys Asn Tyr Gly Ala
         65                  70                  75 cca gaa ccc aat gtg cct tca aga gag gcc tta gca gaa ctt agt agc       291
Pro Glu Pro Asn Val Pro Ser Arg Glu Ala Leu Ala Glu Leu Ser Ser
 80                  85                  90 cag cag gag tat ctc aag ctt aag gag cgt tat gac gcc tta cag aga       339
Gln Gln Glu Tyr Leu Lys Leu Lys Glu Arg Tyr Asp Ala Leu Gln Arg
 95                 100                 105                 110 acc caa agg aat ctg ttg gga gaa gat ctt gga cct cta agt aca aag       387
Thr Gln Arg Asn Leu Leu Gly Glu Asp Leu Gly Pro Leu Ser Thr Lys
                115                 120                 125 gag ctt gag tca ctt gag aga cag ctt gat tct tcc ttg aag cag atc       435
Glu Leu Glu Ser Leu Glu Arg Gln Leu Asp Ser Ser Leu Lys Gln Ile
        130                 135                 140 aga gct ctc agg aca cag ttt atg ctt gac cag ctc aac gat ctt cag       483
Arg Ala Leu Arg Thr Gln Phe Met Leu Asp Gln Leu Asn Asp Leu Gln
145                 150                 155 agt aag gaa cgc atg ctg act gag aca aat aaa act cta aga cta agg       531
Ser Lys Glu Arg Met Leu Thr Glu Thr Asn Lys Thr Leu Arg Leu Arg
    160                 165                 170 tta gct gat ggg tat cag atg cca ctc cag ctg aac cct aac caa gaa       579
Leu Ala Asp Gly Tyr Gln Met Pro Leu Gln Leu Asn Pro Asn Gln Glu
175                 180                 185                 190 gag gtt gat cac tac ggt cgt cat cat cat caa caa caa caa cac tcc       627
Glu Val Asp His Tyr Gly Arg His His His Gln Gln Gln Gln His Ser
                195                 200                 205 caa gct ttc ttc cag cct ttg gaa tgt gaa ccc att ctt cag atc ggg       675
Gln Ala Phe Phe Gln Pro Leu Glu Cys Glu Pro Ile Leu Gln Ile Gly
        210                 215                 220 tat cag ggg caa caa gat gga atg gga gca gga cca agt gtg aat aat       723
Tyr Gln Gly Gln Gln Asp Gly Met Gly Ala Gly Pro Ser Val Asn Asn
            225                 230                 235 tac atg ttg ggt tgg tta cct tat gac acc aac tct att tga atc ttt       771
Tyr Met Leu Gly Trp Leu Pro Tyr Asp Thr Asn Ser Ile     Ile Phe
        240                 245                 250 ctc act taa tca atc cct ctc ttt ttt ttt ttg aca ttt tta aga tga       819
Leu Thr     Ser Ile Pro Leu Phe Phe Phe Leu Thr Phe Leu Arg
255                 260                 265                 270 tgtttcta                                                              827
```

<210> SEQ ID NO 9
<211> LENGTH: 251
<212> TYPE: PRT
<213> ORGANISM: Arabidopsis thaliana
<220> FEATURE:
<223> OTHER INFORMATION: AGAMOUS-LIKE 9 (AGL9)

<400> SEQUENCE: 9

```
Lys Met Gly Arg Gly Arg Val Glu Leu Lys Arg Ile Glu Asn Lys Ile
 1               5                  10                  15

Asn Arg Gln Val Thr Phe Ala Lys Arg Arg Asn Gly Leu Leu Lys Lys
            20                  25                  30

Ala Tyr Glu Leu Ser Val Leu Cys Asp Ala Glu Val Ala Leu Ile Ile
        35                  40                  45

Phe Ser Asn Arg Gly Lys Leu Tyr Glu Phe Cys Ser Ser Ser Ser Met
 50                  55                  60

Leu Arg Thr Leu Glu Arg Tyr Gln Lys Cys Asn Tyr Gly Ala Pro Glu
 65                  70                  75                  80

Pro Asn Val Pro Ser Arg Glu Ala Leu Ala Glu Leu Ser Ser Gln Gln
                85                  90                  95

Glu Tyr Leu Lys Leu Lys Glu Arg Tyr Asp Ala Leu Gln Arg Thr Gln
            100                 105                 110

Arg Asn Leu Leu Gly Glu Asp Leu Gly Pro Leu Ser Thr Lys Glu Leu
        115                 120                 125

Glu Ser Leu Glu Arg Gln Leu Asp Ser Ser Leu Lys Gln Ile Arg Ala
130                 135                 140

Leu Arg Thr Gln Phe Met Leu Asp Gln Leu Asn Asp Leu Gln Ser Lys
145                 150                 155                 160

Glu Arg Met Leu Thr Glu Thr Asn Lys Thr Leu Arg Leu Arg Leu Ala
                165                 170                 175

Asp Gly Tyr Gln Met Pro Leu Gln Leu Asn Pro Asn Gln Glu Glu Val
            180                 185                 190

Asp His Tyr Gly Arg His His Gln Gln Gln His Ser Gln Ala
        195                 200                 205

Phe Phe Gln Pro Leu Glu Cys Glu Pro Ile Leu Gln Ile Gly Tyr Gln
210                 215                 220

Gly Gln Gln Asp Gly Met Gly Ala Gly Pro Ser Val Asn Asn Tyr Met
225                 230                 235                 240

Leu Gly Trp Leu Pro Tyr Asp Thr Asn Ser Ile
                245                 250
```

<210> SEQ ID NO 10
<211> LENGTH: 4
<212> TYPE: PRT
<213> ORGANISM: Arabidopsis thaliana
<220> FEATURE:
<223> OTHER INFORMATION: AGL9 cDNA peptide

<400> SEQUENCE: 10

```
Ile Phe Leu Thr
 1
```

<210> SEQ ID NO 11
<211> LENGTH: 12
<212> TYPE: PRT
<213> ORGANISM: Arabidopsis thaliana
<220> FEATURE:
<223> OTHER INFORMATION: AGL9 cDNA peptide

<400> SEQUENCE: 11

Ser Ile Pro Leu Phe Phe Phe Leu Thr Phe Leu Arg
 1               5                  10

<210> SEQ ID NO 12
<211> LENGTH: 5368
<212> TYPE: DNA
<213> ORGANISM: Arabidopsis thaliana
<220> FEATURE:
<223> OTHER INFORMATION: AP1 promoter

<400> SEQUENCE: 12

| | | | | | |
|---|---|---|---|---|---|
| gaattccccg | gatctccata | tacatatcat | acatatatat | agtatactat | ctttagactg | 60 |
| atttctctat | acactatctt | ttaacttatg | tatcgtttca | aaactcagga | cgtacatgtt | 120 |
| ttaaatttgg | ttatataacc | acgaccattt | caagtatata | tgtcatacca | taccagattt | 180 |
| aatataactt | ctatgaagaa | aatacataaa | gttggattaa | aatgcaagtg | acatcttttt | 240 |
| agcataggtt | catttggcat | agaagaaata | tataactaaa | aatgaacttt | aacttaaata | 300 |
| gattttacta | tattcaatt | ttttcttttt | acatggtcta | atttattttt | ctaaaattag | 360 |
| tatgattgtt | gttttgatga | aacaataata | ccgtaagcaa | tagttgctaa | aagatgtcca | 420 |
| aatatttata | aattcaaag | taaatcaaat | aaggaagaag | acacgtggaa | acaccaaat | 480 |
| aagagaagaa | atggaaaaaa | cagaaagaaa | tttttaaca | agaaaaatca | attagtcctc | 540 |
| aaacctgaga | tatttaaagt | aatcaactaa | acaggaaca | cttgactaac | aaagaaattt | 600 |
| gaaatgtggt | ccaactttca | cttaattata | ttgttttctc | taaggcttat | gcaatatatg | 660 |
| ccttaagcaa | atgccgaatc | tgtttttttt | tttgttatt | ggatattgac | tgaaaataag | 720 |
| gggttttttc | acacttgaag | atctcaaaag | agaaaactat | tacaacgaaa | attcattgta | 780 |
| aaagaagtga | ttaagcaaat | tgagcaaagg | ttttatgtg | gtttatttca | ttatatgatt | 840 |
| gacatcaaat | tgtatatata | tggttgtttt | atttaacaat | atatatgat | ataacgtaca | 900 |
| aactaaatat | gtttgattga | cgaaaaaaa | tatatgtatg | tttgattaac | aacatagcac | 960 |
| atattcaact | gattttgtc | ctgatcatct | acaacttaat | aagaacacac | aacattgaaa | 1020 |
| aaatctttga | caaaatacta | tttttgggtt | tgaaattttg | aatacttaca | attattcttc | 1080 |
| tcgatcttcc | tctctttcct | taaatcctgc | gtacaaatcc | gtcgacgcaa | tacattacac | 1140 |
| agttgtcaat | tggttctcag | ctctaccaaa | aacatctatt | gccaaaagaa | aggtctattt | 1200 |
| gtacttcact | gttacagctg | agaacattaa | atataataag | caaatttgat | aaaacaaagg | 1260 |
| gttctcacct | tattccaaaa | gaatagtgta | aaataggta | atagagaaat | gttaataaaa | 1320 |
| ggaaattaaa | aatagatatt | ttggttggtt | cagattttgt | ttcgtagatc | tacagggaaa | 1380 |
| tctccgccgt | caatgcaaag | cgaaggtgac | acttgggaa | ggaccagtgg | tccgtacaat | 1440 |
| gttacttacc | catttctctt | cacgagacgt | cgataatcaa | attgtttatt | ttcatatttt | 1500 |
| taagtccgca | gttttattaa | aaaatcatgg | acccgacatt | agtacgagat | ataccaatga | 1560 |
| gaagtcgaca | cgcaaatcct | aaagaaacca | ctgtggtttt | tgcaaacaag | agaaaccagc | 1620 |
| tttagctttt | ccctaaaacc | actcttaccc | aaatctctcc | ataaataaag | atcccgagac | 1680 |
| tcaaacacaa | gtctttttat | aaaggaaaga | agaaaaaact | ttcctaattg | gttcatacca | 1740 |
| aagtctgagc | tcttctttat | atctctcttg | tagtttctta | ttgggggtct | ttgttttgtt | 1800 |
| tggttctttt | agagtaagaa | gtttcttaaa | aaaggatcaa | aaatgggaag | gggtagggtt | 1860 |
| caattgaaga | ggatagagaa | caagatcaat | agacaagtga | cattctcgaa | aagaagagct | 1920 |

```
ggtcttttga agaaagctca tgagatctct gttctctgtg atgctgaagt tgctcttgtt    1980
gtcttctccc ataagcggaa actcttcgaa tactccactg attcttggta acttcaacta    2040
attctttact tttaaaaaaa tcttttaatc tgctacttta tatagttttt ttccccctta    2100
agttgactac ttgatttgcc ctaattattc actactgctt ttgttatata ttttctaggg    2160
cttccatttt tggatttttt gattagccag aaaaatgttt aatacaaatt tgtataattt    2220
aaaaatcaaa actttagggc cgtagtgaag tgaaccctag aacacacaga ttataccata    2280
gtaattacct tgatatattg tgcaatattt atcagcatca tatcttcaaa ctcaagagat    2340
atagaagggt atgttaatct ttgaactagg gttttgatcc ctaactcata atgaatcctt    2400
ttgttctcca atagccatgt ctttcgaatt tgcagatcta agctctaatt gatgccatag    2460
taagaaaata agatctgtag ttttcactcg ctcactgagt tcgagtttta aatgaagtgt    2520
cgtttctttt ttcatatata gttgcaactg gattataatt aaaaaatatt atgggacgag    2580
aaaataattt aaaatagata tagataacaa tgtcaaattg agaatttttt attagaaaga    2640
atatttaact tacgagttgt ttttttttcag ctgtaaaaga atatctaatt tgttctcacg    2700
actgtgtctt catgttttgc aaatctaagc aaagaaaatg tttaaactcg gatcttaaga    2760
ttatgaactc gtaatataaa acactatata gtattaaatt tgaactagtg ttgcttcttt    2820
tgctactttg actttagaaa ttaaaactga aacaaagatg tcaaatctga gtagggagtc    2880
tttgacctct ggggatccat aaaaagaact aactccatcc taaaatcggc ttcttaccga    2940
tggtcaaact tagctccaac aagcaacagc tgttcttctt tttttttttt tttttttttt    3000
tttaagcatt gtccttgttc tgaaaaaaaa taagattggt aaattggcaa gattataata    3060
atttattata atgtgtcgca ctaagaagat tttctgtacc taattgtagc aaaattaaag    3120
aaaccgcagt tagaactcga agctaagagc ataggtgtcta tgattcatac tgttttgtta    3180
ttataaaggt atcatagaga tcggtacttg atttgttata ggaaatcttg gtttaattgc    3240
ataaaaccat cattagattt atcctaaaat gtgatgatat tttggtcaca tctccatatt    3300
atttatataa taaatgata attggttgat gataaagcta accctaattc tgtgaaatga    3360
tcagtatgga gaagatactt gaacgctatg agaggtactc ttacgccgaa agacagctta    3420
ttgcacctga gtccgacgtc aatgtatttc aataaatatt tctccttta atccacatat    3480
atattatatc aatctatttg tagtattgat gaattttatt tgtataaaac ttctggtaca    3540
cagacaaact ggtcgatgga gtataacagg cttaaggcta agattgagct tttggagaga    3600
aaccagaggt acacatttac actcatcaca tttctatcta gaaaatcgat cgggttccat    3660
tttaaagtaa gttaaaattc attgatgcta ttgaaattca ggcattatct tggggaagac    3720
ttgcaagcaa tgagccctaa agagcttcag aatctggagc agcagcttga cactgctctt    3780
aagcacatcc gcactagaaa agtattgcct tctgctatttt cgttgaacat atctatataa    3840
cttaaacgtt tacaagtgtt attataatgt gaacattgaa atacatatgt gtatgtatca    3900
atatatatat cagtaatcaa tatcaatttg atatgtctat aggttggttc gaatgtatga    3960
gttatgttgt gtattttaag actccatatt acttaaagta atgggttgtt aatgttgatg    4020
tgtgtgtatg cagaaccaac ttatgtacga gtccatcaat gagctccaaa aaaggtatg     4080
taaaccccct atcaaatgta tgtcttatag agaaacgtat aggaaagcta attaacaatc    4140
gtgccgtttc ggaaatgaca ggagaaggcc atacaggagc aaaacagcat gctttctaaa    4200
caggtaacac atgtcatcat ttctctttca tcaacatgtt gtccattgca ttactgttac    4260
cttccactgt tctgctccac acttccagcc aagctatacc tacgatatct tcatatctcc    4320
```

-continued

| | |
|---|---|
| acttaacttc ggcaccatta aataaaaata gaaaatcttt gcaaatttgt ttgaaatagc | 4380 |
| atagatgttg tctattgatt gatataatca ccagcctgta cgtagatatg gtttgtccgt | 4440 |
| ttagttttaa ggtgtctctc ggattgaaaa tattttgaaa tcttttgaaa tgtttgtccc | 4500 |
| atcattctta cttagctcat atctatgtat atgaatatag acactactcc taattataaa | 4560 |
| atgttataat agttcattgc atgagtgcaa ctgtgaaaat aactatttgt aaccattgca | 4620 |
| tatatatagt ttcttcactt tgaaaattga tgatgataat atggtttgaa ataaatttgc | 4680 |
| tggcagatca aggagaggga aaaaattctt agggctcaac aggagcagtg ggatcagcag | 4740 |
| aaccaaggcc acaatatgcc tccccctctg ccaccgcagc agcaccaaat ccagcatcct | 4800 |
| tacatgctct ctcatcagcc atctcctttt ctcaacatgg ggtaacaaaa aattactaat | 4860 |
| cagtcttaat ttaaagcaca tatgttatgc aagctagtta cgttaggtgt tgtaatttca | 4920 |
| ttgaagttat agctgttagt gatggttaca tgatgctaga ttttgaaact agaaaacttt | 4980 |
| attttaaaac attatttat taacgtaggt taatgcaatg gtcgccaaac gaacaaactt | 5040 |
| attagtgtgg aaaaatgtac atggaatggt tgcgaaaagc ctaagtcgac ttttgttgtt | 5100 |
| gttggtctat gtgtttaagt acaattttag tttgttagat aaatgaaatt aatatatctt | 5160 |
| tgacatttca caatggactg atatttgatt tcctttgtt gtacggtgaa acatatgatt | 5220 |
| acatatgcac tttcatatat atcctatgta tgattgtgaa tgcagtggtc tgtatcaaga | 5280 |
| agatgatcca atggcaatga ggaggaatga tctcgaactg actcttgaac ccgtttacaa | 5340 |
| ctgcaacctt ggctgcttcg ccgcatga | 5368 |

<210> SEQ ID NO 13
<211> LENGTH: 1220
<212> TYPE: DNA
<213> ORGANISM: Arabidopsis thaliana
<220> FEATURE:
<223> OTHER INFORMATION: AP1 cDNA
<220> FEATURE:
<221> NAME/KEY: CDS
<222> LOCATION: (141)..(911)
<223> OTHER INFORMATION: AP1

<400> SEQUENCE: 13

| | |
|---|---|
| gaattcggca cgagaacttt cctaattggt tcataccaaa gtctgagctc ttctttatat | 60 |
| ctctcttgta gtttcttatt gggggtcttt gttttgtttg gttcttttag agtaagaagt | 120 |

| | |
|---|---|
| ttcttaaaaa aggatcaaaa atg gga agg ggt agg gtt caa ttg aag agg ata | 173 |
| Met Gly Arg Gly Arg Val Gln Leu Lys Arg Ile | |
| 1 5 10 | |

| | |
|---|---|
| gag aac aag atc aat aga caa gtg aca ttc tcg aaa aga aga gct ggt | 221 |
| Glu Asn Lys Ile Asn Arg Gln Val Thr Phe Ser Lys Arg Arg Ala Gly | |
| 15 20 25 | |

| | |
|---|---|
| ctt ttg aag aaa gct cat gag atc tct gtt ctc tgt gat gct gaa gtt | 269 |
| Leu Leu Lys Lys Ala His Glu Ile Ser Val Leu Cys Asp Ala Glu Val | |
| 30 35 40 | |

| | |
|---|---|
| gct ctt gtt gtc ttc tcc cat aag ggg aaa ctc ttc gaa tac tcc act | 317 |
| Ala Leu Val Val Phe Ser His Lys Gly Lys Leu Phe Glu Tyr Ser Thr | |
| 45 50 55 | |

| | |
|---|---|
| gat tct tgt atg gag aag ata ctt gaa cgc tat gag agg tac tct tac | 365 |
| Asp Ser Cys Met Glu Lys Ile Leu Glu Arg Tyr Glu Arg Tyr Ser Tyr | |
| 60 65 70 75 | |

| | |
|---|---|
| gcc gaa aga cag ctt att gca cct gag tcc gac gtc aat aca aac tgg | 413 |
| Ala Glu Arg Gln Leu Ile Ala Pro Glu Ser Asp Val Asn Thr Asn Trp | |
| 80 85 90 | |

| | | | | | | | | | | | | | | | | |
|---|---|---|---|---|---|---|---|---|---|---|---|---|---|---|---|---|
| tcg | atg | gag | tat | aac | agg | ctt | aag | gct | aag | att | gag | ctt | ttg | gag | aga | 461 |
| Ser | Met | Glu | Tyr | Asn | Arg | Leu | Lys | Ala | Lys | Ile | Glu | Leu | Leu | Glu | Arg | |
| | | | 95 | | | | | 100 | | | | | 105 | | | |
| aac | cag | agg | cat | tat | ctt | ggg | gaa | gac | ttg | caa | gca | atg | agc | cct | aaa | 509 |
| Asn | Gln | Arg | His | Tyr | Leu | Gly | Glu | Asp | Leu | Gln | Ala | Met | Ser | Pro | Lys | |
| | | 110 | | | | | 115 | | | | | 120 | | | | |
| gag | ctt | cag | aat | ctg | gag | cag | cag | ctt | gac | act | gct | ctt | aag | cac | atc | 557 |
| Glu | Leu | Gln | Asn | Leu | Glu | Gln | Gln | Leu | Asp | Thr | Ala | Leu | Lys | His | Ile | |
| | 125 | | | | | 130 | | | | | 135 | | | | | |
| cgc | act | aga | aaa | aac | caa | ctt | atg | tac | gag | tcc | atc | aat | gag | ctc | caa | 605 |
| Arg | Thr | Arg | Lys | Asn | Gln | Leu | Met | Tyr | Glu | Ser | Ile | Asn | Glu | Leu | Gln | |
| 140 | | | | | 145 | | | | | 150 | | | | | 155 | |
| aaa | aag | gag | aag | gcc | ata | cag | gag | caa | aac | agc | atg | ctt | tct | aaa | cag | 653 |
| Lys | Lys | Glu | Lys | Ala | Ile | Gln | Glu | Gln | Asn | Ser | Met | Leu | Ser | Lys | Gln | |
| | | | | 160 | | | | | 165 | | | | | 170 | | |
| atc | aag | gag | agg | gaa | aaa | att | ctt | agg | gct | caa | cag | gag | cag | tgg | gat | 701 |
| Ile | Lys | Glu | Arg | Glu | Lys | Ile | Leu | Arg | Ala | Gln | Gln | Glu | Gln | Trp | Asp | |
| | | | 175 | | | | | 180 | | | | | 185 | | | |
| cag | cag | aac | caa | ggc | cac | aat | atg | cct | ccc | cct | ctg | cca | ccg | cag | cag | 749 |
| Gln | Gln | Asn | Gln | Gly | His | Asn | Met | Pro | Pro | Pro | Leu | Pro | Pro | Gln | Gln | |
| | | 190 | | | | | 195 | | | | | 200 | | | | |
| cac | caa | atc | cag | cat | cct | tac | atg | ctc | tct | cat | cag | cca | tct | cct | ttt | 797 |
| His | Gln | Ile | Gln | His | Pro | Tyr | Met | Leu | Ser | His | Gln | Pro | Ser | Pro | Phe | |
| | 205 | | | | | 210 | | | | | 215 | | | | | |
| ctc | aac | atg | ggt | ggt | ctg | tat | caa | gaa | gat | gat | cca | atg | gca | atg | agg | 845 |
| Leu | Asn | Met | Gly | Gly | Leu | Tyr | Gln | Glu | Asp | Asp | Pro | Met | Ala | Met | Arg | |
| 220 | | | | | 225 | | | | | 230 | | | | | 235 | |
| agg | aat | gat | ctc | gaa | ctg | act | ctt | gaa | ccc | gtt | tac | aac | tgc | aac | ctt | 893 |
| Arg | Asn | Asp | Leu | Glu | Leu | Thr | Leu | Glu | Pro | Val | Tyr | Asn | Cys | Asn | Leu | |
| | | | | 240 | | | | | 245 | | | | | 250 | | |
| ggc | tgc | ttc | gcc | gca | tga | agcatttcca | tatatatata | tttgtaatcg | | | | | | | | 941 |
| Gly | Cys | Phe | Ala | Ala | | | | | | | | | | | | |
| | | | 255 | | | | | | | | | | | | | |

| | |
|---|---|
| tcaacaataa aaacagtttg ccacatacat ataaatagtg gctaggctct tttcatccaa | 1001 |
| ttaatatatt ttggcaaatg ttcgatgttc ttatatcatc atatataaat tagcaggctc | 1061 |
| ctttcttctt ttgtaatttg ataagtttat ttgcttcaat atggagcaaa attgtaatat | 1121 |
| atttgaaggt cagagagaat gaacgtgaac ttaatagaaa aaaaaaaaaa aaaaaaaaa | 1181 |
| aaaaaaaaaa aaaaaaccc gacgtagctc gaggaattc | 1220 |

<210> SEQ ID NO 14
<211> LENGTH: 256
<212> TYPE: PRT
<213> ORGANISM: Arabidopsis thaliana
<220> FEATURE:
<223> OTHER INFORMATION: AP1

<400> SEQUENCE: 14

Met Gly Arg Gly Arg Val Gln Leu Lys Arg Ile Glu Asn Lys Ile Asn
 1               5                  10                  15

Arg Gln Val Thr Phe Ser Lys Arg Arg Ala Gly Leu Leu Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Ser Thr Asp Ser Cys Met Glu
    50                  55                  60

Lys Ile Leu Glu Arg Tyr Glu Arg Tyr Ser Tyr Ala Glu Arg Gln Leu
65                  70                  75                  80

```
Ile Ala Pro Glu Ser Asp Val Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Thr Arg Lys Asn
    130                 135                 140

Gln Leu Met Tyr Glu Ser Ile Asn Glu Leu Gln Lys Lys Glu Lys Ala
145                 150                 155                 160

Ile Gln Glu Gln Asn Ser Met Leu Ser Lys Gln Ile Lys Glu Arg Glu
                165                 170                 175

Lys Ile Leu Arg Ala Gln Gln Glu Gln Trp Asp Gln Gln Asn Gln Gly
            180                 185                 190

His Asn Met Pro Pro Pro Leu Pro Pro Gln Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Asp Asp Pro Met Ala Met Arg Arg Asn Asp Leu Glu
225                 230                 235                 240

Leu Thr Leu Glu Pro Val Tyr Asn Cys Asn Leu Gly Cys Phe Ala Ala
                245                 250                 255

<210> SEQ ID NO 15
<211> LENGTH: 1374
<212> TYPE: DNA
<213> ORGANISM: Arabidopsis thaliana
<220> FEATURE:
<223> OTHER INFORMATION: AGL4 cDNA
<220> FEATURE:
<221> NAME/KEY: CDS
<222> LOCATION: (347)..(1099)
<223> OTHER INFORMATION: AGL4

<400> SEQUENCE: 15
gaattccgga ttcacaaaaa cttttcttca gattcacaat ctcatcacaa cccttcaaaa      60
agagaaaaga tctaaagaat aaacaagagc cctaatatca aatcacaacc aaaaaaacca     120
aagaaagcta attaaagttt tctctctagc tattcctctt cttttcttgt tcttgaaaac     180
tagggtttac ttcaccaaaa gataagatct ttccccagaa aaagcaatac ccaagtcatg     240
tttctgtgtg tctgtatata gataaaacat tacatacct aataaggtta cacaaatagc      300 tataaagag ggaaaataag atagggattt tttggggtga ggaaagatgg gaagaggaag      360
agtagagctc aagaggatag agaacaaaat caacagacaa gtgacgtttg ctaaacgtag     420
aaatggtttg ctgaaaaaag cttatgagct ttctgttctc tgcgatgctg aagtctctct     480
catcgtcttc tccaaccgtg gcaagctcta cgagttctgc agcacctcca acatgctcaa     540
gacactggaa aggtatcaga agtgtagcta tggctccatt gaagtcaaca acaaacctgc     600
taaagagctt gagaacagct acagagagta cttgaagctg aaaggtagat atgaaaatct     660
gcaacgtcag cagagaaatc ttcttggaga ggatcttgga cctctgaatt caaaggagct     720
agagcagctt gagcgtcaac tagcggctc tctgaagcaa gttcgctgca tcagacaca      780 gtatatgctt gaccagctct ctgatcttca aggtaaggag catatcttgc ttgatgccaa     840
cagagctttg tcaatgaagc tggaagatat gatcggcgtg agacatcacc atataggagg     900
aggatgggaa ggtggtgatc aacagaatat tgcctatgga catcctcagg ctcattctca     960
```

```
gggactatac caatctcttg aatgtgatcc cactttgcaa attggatata gccatccagt    1020
gtgctcagag caaatggctg tgacggtgca aggtcagtcc caacaaggaa acggctacat    1080
ccctggctgg atgctgtgag cgatacttct tcccccaata agatcttaa gcaagtactg     1140 gtggggtctt cgtggtgtga tcttagatct tatgcatatg aataataatg ttattgcaca    1200
agacttttgc ttttgtagac acaagtggct atagctgtaa tagccttcaa catctctctt    1260
ctgtttcagg atttgtttgt gcctattgta attgcttata tatgtatggt ttgtataatg    1320
tgtgaaatgt taacatcgac catgtctcat ctggtgaaaa aaaaaaaaa aaaa            1374
```

<210> SEQ ID NO 16
<211> LENGTH: 1303
<212> TYPE: DNA
<213> ORGANISM: Arabidopsis thaliana
<220> FEATURE:
<223> OTHER INFORMATION: AGL2 cDNA
<220> FEATURE:
<221> NAME/KEY: CDS
<222> LOCATION: (396)..(1142)
<223> OTHER INFORMATION: AGL2

<400> SEQUENCE: 16

```
gaattccggc cctcacacat ttcttatctt ttgctctcaa tagattccat tgattcaaaa    60
caaaattttc attaagattt cacaacctcc acacacttcc aaacacaatt aaagagagga   120 aaagaatca ataaccctat aaataaaaaa tcagacaaac agaagtttcc tcttcttctt    180
ccttaagcta gtaccttttg ttcttgaaat tagggttaat ttcttttttc caaataccat   240
caattctcca gaccataaaa actcaaaaag atcagatctt tcctctgaaa aagagatacc   300
caacttatgt ttttgtgtgt ctgtatatag ataaacatta catacccata tttgtgtata   360
gacataaaaa gtgaaaatta agtaacaaa agaaatggg aagaggaaga gtagagctga    420
agaggataga gaacaaaatc aacagacaag taacgtttgc aaagcgtagg aacggtttgt    480
tgaagaaagc ttatgaattg tctgttctct gtgatgctga agttgctctc atcatcttct    540
ccaaccgtgg aaagctctat gagttttgca gctcctcaaa catgctcaag acacttgatc    600
ggtaccagaa atgcagctat ggatccattg aagtcaacaa caaacctgcc aaagaacttg    660
agaacagcta cagagaatat ctgaagctta agggtagata tgagaaccctt caacgtcaac    720 agagaaatct tcttggggag gatttaggac ctttgaattc aaaggagtta gagcagcttg    780
agcgtcaact ggacggctct ctcaagcaag ttcggtccat caagacacag tacatgcttg    840
accagctctc ggatcttcaa aataaagagc aaatgttgct tgaaaccaat agagctttgg    900
caatgaagct ggatgatatg attggtgtga gaagtcatca tatgggagga tgggaaggcg    960
gtgaacagaa tgttacctac gcgcatcatc aagctcagtc tcaggacta taccagcctc   1020 ttgaatgcaa tccaactctg caaatggggt atgataatcc agtatgctct gagcaaatca   1080
ctgcgacaac acaagctcag gcgcagccgg gaaacgttta cattccagga tggatgctct   1140
gagaatcatg tactgtgatg aagctcaccc acaaaagacc ttatatatat ataaagtata   1200
gatacaagac ttggatttgt agacataagt ggctaatata atggtcctga ggatcttcta   1260
gacatttgta tcttttggga atccttgctt atattaagaa ttc                    1303
```

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:forward

```
                                     -continued primer AP1HIN

<400> SEQUENCE: 17
caagcttgta cacatttaca ctcatcacat                                              30

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:reverse
      primer AP1BAM

<400> SEQUENCE: 18
cggatcctgc gcgaagcagc caaggttg                                                28
```

What is claimed is:

1. A transgenic plant characterized by suppressed flowering, comprising a nucleic acid molecule comprising a floral organ selective regulatory element from an *Arabidopsis* AP1 gene, operatively linked to a nucleotide sequence encoding a cytotoxic gene product, wherein said nucleic acid molecule is heritable by progeny thereof.

2. The transgenic plant of claim 1, wherein said cytotoxic gene product is selected from the group consisting of diphtheria toxic A chain, RNase T1, Barnase Rnase, ricin toxin A chain, and herpes simplex virus thymidine kinase (tk).

3. The transgenic plant of claim 1, wherein said nucleic acid molecule comprises a fragment of at least 100 contiguous nucleotides of SEQ ID NO:12.

4. A tissue derived from the transgenic plant of any of claim 1, 2, or 3.

5. The tissue of claim 4, which is capable of non-vegetative propagation.

6. The tissue of claim 4, which is capable of vegetative propagation.

7. The plant of claim 1, wherein said plant is a woody plant.

8. The plant of claim 7, wherein said plant is a tree.

9. A method of producing a transgenic plant characterized by suppressed flowering, comprising introducing into a plant an exogenous nucleic acid molecule comprising a floral organ selective regulatory element from an *Arabidopsis* AP1 gene, wherein said regulatory element is operatively linked to a nucleotide sequence encoding a cytotoxic gene product, whereby flowering is suppressed due to selective expression of said exogenous nucleic acid molecule in said floral organ, and wherein said nucleic acid molecule is heritable by progeny thereof.

10. The method of claim 9, wherein said nucleic acid molecule comprises a fragment of at least 100 contiguous nucleotides of SEQ ID NO:12.

11. The method of claim 9, wherein said cytotoxic gene product is selected from the group consisting of diphtheria toxic A chain, RNase T1, Barnase Rnase, ricin toxin A chain, and herpes simplex virus thymidine kinase (tk).

12. The method of claim 9, wherein the nucleic acid molecule is introduced into the plant by *Agrobacterium*-mediated transformation.

13. The method of claim 12, wherein *Agrobacterium tumefaciens* is used to introduce the nucleic acid molecule into the plant.

14. The method of claim 12, wherein *Agrobacterium rhizogenes* is used to introduce the nucleic acid molecule into the plant.

15. The transgenic plant of claim 1, wherein said plant is obtainable by a process comprising the steps of (i) introducing into a plant an exogenous nucleic acid molecule comprising a floral organ selective regulatory element, wherein said regulatory element is operatively linked to a nucleotide sequence encoding a cytotoxic gene product; (ii) identifying or selecting a population of plants whose flowering is suppressed; (iii) generating a progeny transgenic plant therefrom.

16. An isolated nucleic acid molecule, comprising a floral organ selective regulatory element from an *Arabidopsis* AP1 gene, operatively linked to a nucleotide sequence encoding a cytotoxic gene product.

17. The isolated nucleic acid molecule of claim 16, comprising at least 100 contiguous nucleotides of SEQ ID NO:12.

18. The isolated nucleic acid molecule of claim 16, wherein said cytotoxic gene product is selected from the group consisting of diphtheria toxic A chain, RNase T1, Barnase Rnase, ricin toxin A chain, and herpes simplex virus thymidine kinase (tk).

19. A kit for producing a transgenic plant characterized by suppressed flowering, comprising packaging containing a plant expression vector comprising a floral organ selective regulatory element from an *Arabidopsis* AP1 gene, wherein the regulatory element is operatively linked to a nucleotide sequence encoding a cytotoxic gene product, and instructions for transforming a susceptible plant with said vector.

20. The kit of claim 19, wherein said cytotoxic gene product is selected from the group consisting of diphtheria toxic A chain, RNase T1, Barnase Rnase, ricin toxin A chain, and herpes simplex virus thymidine kinase (tk).

* * * * *